US008563689B1

(12) United States Patent
Takashi et al.

(10) Patent No.: US 8,563,689 B1
(45) Date of Patent: *Oct. 22, 2013

(54) METHODS FOR REGULATING INFLAMMATORY MEDIATORS AND PEPTIDES FOR USEFUL THEREIN

(75) Inventors: Shuji Takashi, Nagano (JP); Indu Parikh, Chapel Hill, NC (US); Kenneth B. Adler, Raleigh, NC (US); Linda D. Martin, Apex, NC (US); Yuehua Li, Pearland, TX (US)

(73) Assignees: North Carolina State University, Raleigh, NC (US); Biomarck Pharmaceuticals, Ltd., Raleigh, NC (US)

( * ) Notice: Subject to any disclaimer, the term of this patent is extended or adjusted under 35 U.S.C. 154(b) by 638 days.

This patent is subject to a terminal disclaimer.

(21) Appl. No.: 12/478,491

(22) Filed: Jun. 4, 2009

Related U.S. Application Data

(63) Continuation of application No. 11/367,449, filed on Mar. 6, 2006, now Pat. No. 7,544,772, which is a continuation-in-part of application No. 10/802,644, filed on Mar. 17, 2004, now abandoned, which is a continuation of application No. 10/180,753, filed on Jun. 26, 2002, now abandoned.

(60) Provisional application No. 60/300,933, filed on Jun. 26, 2001.

(51) Int. Cl.
*C07K 14/00* (2006.01)
(52) U.S. Cl.
USPC ........... 530/326; 530/325; 530/327; 530/328; 530/329
(58) Field of Classification Search
USPC .......................... 530/326, 325, 327, 328, 329
See application file for complete search history.

(56) References Cited

U.S. PATENT DOCUMENTS

| | | | |
|---|---|---|---|
| 4,753,945 A | 6/1988 | Gilbard et al. | |
| 4,873,346 A | 10/1989 | Anderson | |
| 5,292,498 A | 3/1994 | Boucher | |
| 5,298,506 A | 3/1994 | Stamler et al. | |
| 5,436,243 A | 7/1995 | Sachs et al. | |
| 5,849,706 A | 12/1998 | Molina y Vedia et al. | |
| 5,849,719 A | 12/1998 | Carson et al. | |
| 5,858,784 A | 1/1999 | Debs et al. | |
| 5,858,981 A | 1/1999 | Schreiber et al. | |
| 5,861,502 A | 1/1999 | Prockop et al. | |
| 6,245,320 B1 | 6/2001 | Kim | |
| 6,407,058 B1 | 6/2002 | Staddon et al. | |
| 6,506,779 B1 | 1/2003 | Cheng et al. | |
| 7,265,088 B1 | 9/2007 | Li et al. | |
| 7,544,772 B2 | 6/2009 | Takashi et al. | |
| 2001/0033827 A1 | 10/2001 | Kim | |
| 2003/0013652 A1 | 1/2003 | Martin et al. | |
| 2003/0125249 A1* | 7/2003 | Blecha et al. | 514/12 |
| 2004/0180836 A1 | 9/2004 | Martin et al. | |
| 2006/0040301 A1 | 2/2006 | Deirmengian | |
| 2006/0205664 A1 | 9/2006 | Parikh | |
| 2006/0217307 A1 | 9/2006 | Takashi et al. | |
| 2008/0020031 A1 | 1/2008 | Li et al. | |

FOREIGN PATENT DOCUMENTS

| | | |
|---|---|---|
| AU | 766800 | 10/2003 |
| CA | 2287501 A1 | 10/1998 |
| EP | 0 551 200 A1 | 7/1993 |
| EP | 1 154 786 | 8/2000 |
| EP | 1 538 162 A2 | 6/2005 |
| EP | 1 538 162 A3 | 6/2005 |
| JP | 2002-538783 A | 11/2002 |
| JP | 2005-519850 A | 7/2005 |
| WO | WO 93/00353 A1 | 1/1993 |
| WO | WO 95/27496 A1 | 10/1995 |
| WO | WO 96/18103 A1 | 6/1996 |
| WO | WO 00/50062 A2 | 8/2000 |
| WO | WO 01/20998 A1 | 3/2001 |
| WO | WO 03/000027 A2 | 1/2003 |
| WO | WO 03/000027 A3 | 5/2003 |
| WO | WO 2006/078899 A2 | 7/2006 |
| WO | WO 2006/078899 A3 | 12/2006 |
| WO | WO 2007/103368 A2 | 9/2007 |

OTHER PUBLICATIONS

Theron, C. N. (South African Medical Journal 56(17), 670-5, 1979).*
Koelsch, Maud (Biomedical Pharmacology 79(8), 1156-1164, 2010).*
Case, John (Archives of Internal Medicine 163(2), pp. 169-178, 2003).*
Millecamps, Magali (European Journal of Pharmacology 583(1), 97-102, 2008).*
Akbiyik, F. (European Journal of Clinical Pharmacology 57(9), 631-636, 2001).*
Ansfield, JAMA 190, 686-688, 1964.*
Sitzia J (Cancer Practice 6(1), 13-21, 1998).*
Abdullah et al., "P2u purinoceptor regulation of mucin secretion in SPOC1 cells, a goblet cell line from the airways," Biochem. J. vol. 316, 1996, pp. 943-951.
Abdullah et al., "Protein kinase C and Ca2+ activation of mucin secretion in airway goblet cells," Am. Physiol. Soc. 273:L201-L210 (1997).

(Continued)

*Primary Examiner* — David Lukton
(74) *Attorney, Agent, or Firm* — Cooley LLP

(57) ABSTRACT

The present invention includes methods of modulating cellular secretory processes. More specifically the present invention relates to modulating or reducing the release of inflammatory mediators from inflammatory cells by inhibiting the mechanism associated with the release of inflammatory mediators from the vesicles or granules in the inflammatory cells in a subject with a chronic inflammatory disease. In this regard, the present invention discloses an intracellular signaling mechanism that illustrates several novel intracellular targets for pharmacological intervention in disorders involving secretion of inflammatory mediators from vesicles in inflammatory cells. MANS peptide and active fragments thereof are useful in such methods.

28 Claims, 18 Drawing Sheets

(56) References Cited

OTHER PUBLICATIONS

Aderem, "The MARCKS family of protein kinase-C substrates," Biochem. Soc. Trans. 23:587-591 (1995).

Adler et al., "Effects of inflammatory mediators and drugs on mucus secretion and mucociliary function," Res. Immunol. 149(3):245-248 (1998).

Adler et al., "Hypersecretion of Mucin in Response to inflammatory Mediators by Guinea Piog Tracheal Epithelial Cells in Vitro is Blocked by Inhibition of Nitric Oxide Synthase," Am. J. Respir. Cell Mol. Biol. 13:526-530 (1995).

Adler et al., "Myristoylated alanine-rich C-kinase substrate protein: A major intracellular regulatory molecule controlling secretion of mucin by human airway goblet cells," Chest 117(5 suppl. 1):266S-267S (2000).

Aigner et al., "Depletion of 43-kD growth associated protein in primary sensory neurons leads to diminished formation and spreading of growth cones," J. Cell Biol. 123(2):417-429 (1993).

Aragona et al., "Effects of a stable analogue pf PGE2 (11-deoxy-13, 14-didehydro-16 (S)-Methylester Methyl PGE2: FCE20700) on the secretory processes of conjunctival goblet cells of rabbit," Exp. Eye Res. 45(5):647-654 (1987).

Barnes, P.J., "Current and future therapies for airway mucus hypersecretion," Novartis Found Symp. 248:237-253 (2002).

Blackshear et al., "The MARCKS family of cellular protein kinase C substrates," J. Biol. Chem. 268(3):1501-1504 (1993).

Bouffard et al., National Center for Biotechnology Information Database, Accession No. G20124. Sep. 28, 1998.

Calle et al., "Glucose-induced phosphorylation of myristoylated alanine-rich C kinase substrate (MARCKS) in isolated rat pancreatic islets," J. Biol. Chem. 267(26):18723-18727 (1992).

Coffey et al., "Glutamate exocytosis and MARCKS phosphorylation are enhanced by a metabotopic glutamate receptor coupled to a protein kinase C synergistically activated by diacylglycerol and arachidonic acid," J. Neurochem. 63(4):1303-1310 (1994).

Cross et al., "Antioxidant Protection: A Function of Tracheobronchial and Gastrointestinal Mucus," The Lancet, Jun. 16, 1984, pp. 1328-1329.

Dizier et al., "Genome screen for asthma and related phenotypes in the French EGEA study," American Journal Respiratory and Critical Care Medicine 162:1812-1818 (2000).

Dray-Charier et al., "Regulation of mucin secretion in human gallbladder epithelial cells: Predominant role of calcium and protein kinase C," Gastroenterology 112(3):978-990 (1997).

Driot et al., "Beneficial effects of a retinoic acid analog, CBS-211 A, on an experimental model of keraoconjunctivitis Sicca.," Invest. Opthalmol. Vis. Sci. 33(1):190-195 (1992).

Elzagallaai, A., et al. "Platelet Secretion Induced by Phorbol Esters Stimulation is Mediated Though Phosphorylation of MARCKS: a MARCKS-Derived Peptide Blocks MARCKS Phosphorylation and Serotonin Release without Affecting Pleckstrin Phosphorylation," Hemostatis, Thrombosis, and Vascular Biology. 95(3):894-902. (Feb. 1, 2000).

European Search Report for application No. 02756467.3 dated Sep. 3, 2004.

Fischer et al., "Tumor Necrosis Factor-α Stimulates Mucin Secretion and Cyclic GMP Production by Guinea Pig Tracheal Epithelial Cells In Vitro," Am. J. Respir. Cell Mol. Biol.. vol. 20. 1999, pp. 413-422.

Garcher et al., "CA 19-9 ELISA test: A new method for studying mucus changes in tears," Br. J. Ophthalmol. 82(1):88-90 (1998).

Gipson et al., "Cellular origin of mucins of the ocular surface tear film," Adv. Exp. Med. Biol. 438:221-227 (1998).

Graff et al., "Protein Kinase C Substrate and Inhibitor Characteristics of Peptides Derived from the Myristoylated Alanine-rich C Kinase Substrate (MARCKS) Protein Phosphorylation Site Domain," J. Biol. Chem. 266(22):14390-14398 (1991).

Harlan et al., "The human myristoylated alanine-rich C kinase substrate (MARCKS) gene (MACS)," J. Biol. Chem. 266(22):14399-14405 (1991).

Huse, "Partial European Search Report," 4 pages, from European Patent application No. 04024019.4, European Patent Office, The Hague, The Netherlands (mailed May 3, 2005).

International Search Report corresponding to PCT/US02/22270 mailed on Jan. 22, 2003.

International Search Report corresponding to PCT/US07/05688 mailed on Feb. 24, 2009.

International Search Report for PCT/US03/21963; mailed Sep. 9, 2004.

Kessler et al., "Stimulation of goblet cell mucous secretion by activation of nerves in rat conjunctiva," Curr. Eye Res. 14(11):985-992 (1995).

Kim et al., "Airway goblet cell mucin: its structure and regulation of secretion," Eur. Resp. J. 10(11):2644-2649 (1997).

Kim et al., "Airway Mucus," Eur. Respir. J. vol. 10, 1997, p. 1438.

King et al., "Alteration of Airway Reactivity by Mucus, Respiration Physiology," vol. 62, 1985, pp. 47-59.

Ko et al., "ATP-induced mucin release from cultured airway goblet cells involves, in part, activation of protein kinase C," Am. J. Resp. Cell Mol. Biol. 16:194-198 (1997).

Krunkosky et al., "Effects of TNFα on Expression of ICAM-1 in Human Airway Epithelial Cells In Vitro," Am. J. Respir. Cell Mol. Biol., vol. 22, 2000, pp. 685-692.

Larivee et al., "Platelet-Activating Factor Induces Airway Mucin Release via Activation of Protein Kinase C: Evidence of Translocation of Protein Kinase C to Membranes," Am. J. Respir. Cell Mol. Biol., vol. 11 ,1994, pp. 194-205.

Lethem et al., "Nucleotide Regulation of Goblet Cells in Human Airway Epithelial Explants: Normal Exocytosis in Cystic Fibrosis," Am. J. Respir. Cell Mol. Biol., vol. 9, 1993, pp. 315-322.

Li,Y., et al., "MARCKS Protein is a Key Molecule Regulation Mucin Secretion by Human Airway Epithelial Cells in Vitro," The Journal of Biological Chemistry. 276(44):40982-40990. (Nov. 2, 2001).

Linen et al., "Physiology of the lacrimal system," Bull. Soc. Beige. Ophtalmol. 238:35-44 (1990).

Liu et al., "Arginine vasopressin (AVP) causes the reversible phosphorylation of the myristoylated alanine-rich C kinase substrate (MARCKS) protein in the ovine anterior pituitary: evidence that MARCKS phosphorylation is associated with adrenocorticotropin (ACTH) secretion," Mol. Cell. Endocrinol. 105:217-226 (1994).

Liu et al., "Arginine vasopressin (AVP) causes the reversible phosphorylation of the myristoylated alanine-rich C kinase substrate (MARCKS) protein in the ovine anterior pituitary: evidence that MARCKS phosphorylation is associated with adrenocorticotropin (ACTH) secretion," Mol. Cell. Endocrinol. 101:247-256 (1994).

Lu et al., "Regulation of angiotensin II-induced neuromodulation by MARCKS in brain neurons," J. Cell Biol. 142(1):217-227 (1998).

Mastropasqua et al., "Tear deficiency in Fuchs' intermediate uveitis," Can. J. Ophthalmol. 31(1):18-20 (1996).

Murray et al., National Center for Biotechnology Information Database, Accession No. G08525. Feb. 5, 1997.

Murray et al., National Center for Biotechnology Information Database, Accession No. G08539. Feb. 5, 1997.

Myat et al., "Identification of the basolateral targeting determinant of a peripheral membrane protein, MacMARCKS, in polarized cells," Current Biology 8(12):677-683 (1998).

Nakamura et al., "Mucin-like glycoprotein secretion is mediated by cyclic-AMP and protein kinase C signal transduction pathways in rat corneal epithelium," Exp. Eye Res. 66(5):513-519 (1998).

Nichols et al., "Demonstration of the mucous layer of the tear film by electron microscopy," Invest. Ophthalmol. Vis. Sci. 26(4):464-473 (1985).

Prescott et al, "Chronic Mucus Hypersecretion in COPD and Death From Pulmonary Infection," Eur. Respir. J., vol. 8, 1995, pp. 1333-1338.

Ralph, "Conjunctival goblet cell density in normal subjects and in dry eye syndromes," Invest. Ophthalmol. Vis. Sci. 14(4):299-302 (1975).

Raufman et al., "Expression and phosphorylation of a MARCKS-Like Protein in Gastric Chief Cells: Further evidence for modulation of pepsinogen secretion by interaction of $Ca^{2+}$/Calmodulin with protein kinase C," J. Cell. Biochem. 64:514-523 (1997).

(56) References Cited

OTHER PUBLICATIONS

Rogers, "Mucus hypersecretion in chronic obstructive pulmonary disease. Chronic Obstructive Pulmonary Disease: Pathogenesis to Treatment," Novartis Foundation. Symposium 234. vol. 234. (2001).
Rogers, D.F. "Airway Goblet Cell Hyperplasia in Asthma: Hypersecretory and Anti-Inflammatory?" Clinical and Experimental Allergy. Editorial 32: 1124-1127 (2002).
Rogers, D.F., "Pulmonary mucus: Pediatric Perspective," Pediatric Pulmonology 36:178-188 (2003).
Shellans et al., "Conjunctival goblet cell response to vasoconstrictor use," J. Ocul. Pharmacol. 5(3):217-220 (1989).
Singer et al., "A MARCKS-related peptide blocks mucus hypersecretion in a moue model of asthma," Nat. Med. 10:193-196 (2004).
Steiger et al., "Concurrent Increases in the Storage and Release of Mucin-like Molecules by Rat Airway Epithelial Cells in Response to Bacterial Endotoxin," Am. J. Respir. Cell Mol. Biol., vol. 12, 1995, pp. 307-314.
Stein, "International Search Report," 5 pages, from intenational patent application PCT/US00/05050, European Patent Office, Rijswijk, The Netherlands (mailed Sep. 9, 2000).
Stormshak et al., "Dynamics of molecular mechanisms underlying ovarian oxytocin secretion," J. Reprod. Fertil. Suppl. 49:379-390 (1995).
Stumpo et al., "Molecular cloning, characterization, and expression of a cDNA encoding the '80-87-kDA' myristoylated alanine-rich C kinase substrate: A major cellular substrate for protein kinase C," Proc. Natl. Acad. Sci. USA 86:4012-4016 (1989).
Thelen et al., "Regulation by phosphorylation of the reversible association of a myristoylated protein kinase C substrate with the plasma membrane," Nature 351:320-322 (1991).
Thelen et al., "Tumor necrosis factor alpha modifies agonist-dependent responses in human neutrophils by inducing the synthesis and myristoylation of a specific protein kinase C substrate," Proc. Natl. Acad. Sci. USA 87(15):5603-5607 (1990).
Thornton et al., "Identification of Two Glycoforms of the MUC5B Mucin in Human Respiratory Mucus," The Journal of Biological Chemistry, vol. 272, No. 14, Apr. 4, 1997, pp. 9561-9566.
Tseng "Topical tretinoin treatment for severe dry-eye disorders," J. Am. Acad. Dermatol. 15(4 part 2):860-866 (1986).
Vergeres et al., "The myristoyl moiety of myristoylated alanine-rich C kinase substrate (MARCKS) and MARCKS-related protein is embedded in the membrane," J. Biol. Chem. 270(34):19879-19887 (1995).
Vishwanath et al., "Adherence of *Pseudomonas aeruginosa* to Human Tracheobronchial Mucin," Infection and Immunity, vol. 45, No. 1, Jul. 1984, pp. 197-202.
Ward, P.A. and Mulligan M.S., "Blocking of adhesion molecules in vivo as anti-inflammatory therapy." Ther. Immunol. 1(3):165-171 (1994).
Wjst et al., "A genome-wide search for linkage to asthma," Genomics 58:1-8, 1999.
Wright et al., "Oxidant stress stimulates mucin secretion and PLC in airway epithelium via a nitric oxide-dependent mechanism," American J. Physiol., vol. 271, pp. L854-L861.
Xu et al., "Genome-wide screen and identification of gene-gene interactions for asthma-susceptibility in three U.S. populations: Collaborative study on the genetics of asthma," American Journal of Human Genetics. 68:1437-1446 (2001).
Zhao, Y., et al. "Role of MARCKS in regulating endothelial cell proliferation." Am J Physiol Cell Physiol. 279:C1611-C1620. (2000).
Pellegrini, "Supplementary European Search Report," 5 pages, European patent appl. No. 07752392.6, European Patent Office (Jun. 6, 2012).
"Official Action," 9 pages, from RU patent appl. No. 2008139414/14, Russian Patent Office (mailed Jun. 3, 2010) with translation attached.
Gleich, "Mechanism of eosinophil-associated inflammation," J. Allergy Clin. Immunol. 105(4):651-663 (2000).
Hoff et al., "Effects of glucocorticoids on the TPA-induced monocytic differentiation," J. Leukoc. Biol. 52:173-182 (1992).
Haddad, "Office Action Summary," 10 pages, U.S. Appl. No. 10/180,753, United States Patent and Trademark Office (mailed Nov. 19, 2003).
Haddad, "Office Action Summary," 14 pages, U.S. Appl. No. 10/180,753, United States Patent and Trademark Office (mailed Jul. 1, 2003).
Haddad, "Office Action Summary," 12 pages, U.S. Appl. No. 10/802,644, United States Patent and Trademark Office (mailed Oct. 6, 2006).
Haddad, "Office Action Summary," 15 pages, U.S. Appl. No. 10/802,644, United States Patent and Trademark Office (mailed Jan. 11, 2006).
Haddad, "Office Action Summary," 8 pages, U.S. Appl. No. 10/802,644, United States Patent and Trademark Office (mailed Jun. 29, 2005).
Haddad, "Office Action Summary," 12 pages, U.S. Appl. No. 10/802,644, United States Patent and Trademark Office (mailed Nov. 30, 2004).
Haddad, "Office Action Summary," 12 pages, U.S. Appl. No. 10/802,644, United States Patent and Trademark Office (mailed Oct. 21, 2004).
Lukton, "Office Action Summary," 4 pages, U.S. Appl. No. 11/367,449, United States Patent and Trademark Office (mailed Aug. 6, 2008).
Grosskopf, "Supplementary Partial European Search Report," 5 pages, European patent appl. No. 02756467.3, European Patent Office (Jul. 30, 2004).
Grosskopf, "Supplementary Partial European Search Report," 4 pages, European patent appl. No. 02756467.3, European Patent Office (Sep. 3, 2004).
Grosskopf, "Supplementary European Search Report," 4 pages, European patent appl. No. 02756467.3, European Patent Office (Nov. 2, 2004).
Grosskopf, "Communication pursuant to Article 96(2) EPC," 3 pages, European patent appl. No. 02756467.3, European Patent Office (Oct. 20, 2006).
Grosskopf, "Communication pursuant to Artcle 94(3) EPC," 2 pages. European patent appl. No. 02756467.3, European Patent Office (Nov. 24, 2009).
Fujimoto, Official Action, 4 pages, Canada patent appl. No. 2,452,123, Canadian Intellectual Property Office (Sep. 22, 2009).
Matsuura, "Office Action," 2 pages, Japan patent appl. No. 2003-506483, Japan Patent Office (Apr. 3, 2009) with translation attached.
Matsuura, "Office Action," 3 pages, Japan patent appl. No. 2003-506483, Japan Patent Office (Aug. 19, 2008) with translation attached.
Haddad, "Written Opinion," 5 pages, PCT appl. No. PCT/US02/22270, IPEA/US United States Patent and Trademark Office (Jun. 16, 2004).
Haddad, "International Preliminary Examination Report," 4 pages, PCT appl. No. PCT/US02/22270, IPEA/US United States Patent and Trademark Office (Apr. 22, 2005).
Sutherland, "Examiner's first report on patent application No. 2008200379," 2 pages, Australia patent appl. No. 2008200379, IP Australia (Jul. 31, 2009).
Desai, "Examiner's first report on patent application No. 2007223983," 3 pages, Australia patent appl. No. 2007223983, IP Australia (Aug. 24, 2009).
Brownlee, "Examiner's report No. 2 on patent application No. 2007223983," 2 pages, Australia patent appl. No. 2007223983, IP Australia (Feb. 4, 2011).
Kuby, "Granulocytic Cells," $3^{rd}$ ed. Immunology, p. 67, WH Freeman & Co., New York (1997).
Abbas et al., "Granulocytes," $3^{rd}$ ed. Cellular and Molecular Immunology, pp. 26-27, WB Saunders Co., Philadelphia (1997).
Pubmed MeSH Tree for Granulocyte:(http://www.ncbi.nlm.nih.gov/mesh/68006098?ordinalpos 1&itool EntrezSystem2.PEntrez.Mesh.Mesh_ResultsPanel.Mesh_RVDocSum) 3 pages.
Lindner, "International Preliminary Report on Patentability," 6 pages, PCT appl. No. PCT/US2007/005688, The International Bureau of WIPO (Mar. 10, 2009).

(56) References Cited

OTHER PUBLICATIONS

"Decision on Grant," 8 pages, from RU patent appl. No. 2008139414/14, Russian Patent Office (mailed May 11, 2011) with translation attached.

Grosskopf, "Communication pursuant to Article 94(3) EPC," 2 pages, European patent appl. No. 02756467.3, European Patent Office (May 5, 2009).

Grosskopf, "Communication pursuant to Article 94(3) EPC," 3 pages, European patent appl. No. 02756467.3, European Patent Office (Jun. 1, 2010).

Grosskopf, "Communication pursuant to Article 94(3) EPC," 3 pages, European patent appl. No. 02756467.3, European Patent Office (Jul. 9, 2010).

Reuhman, "Examination Report," 2 pages, New Zealand patent appl. No. 570938, Intellectual Property Office of New Zealand (May 17, 2010).

* cited by examiner

1: Calphostin C (500nM), PKC inhibitor
2: Rp-8-Br-PET-cGMP (10μM), PKG inhibitor
3: LY83583 (50μM), GC-S inhibitor
4: KT5720 (500nM), PKA inhibitor FIG. 4A
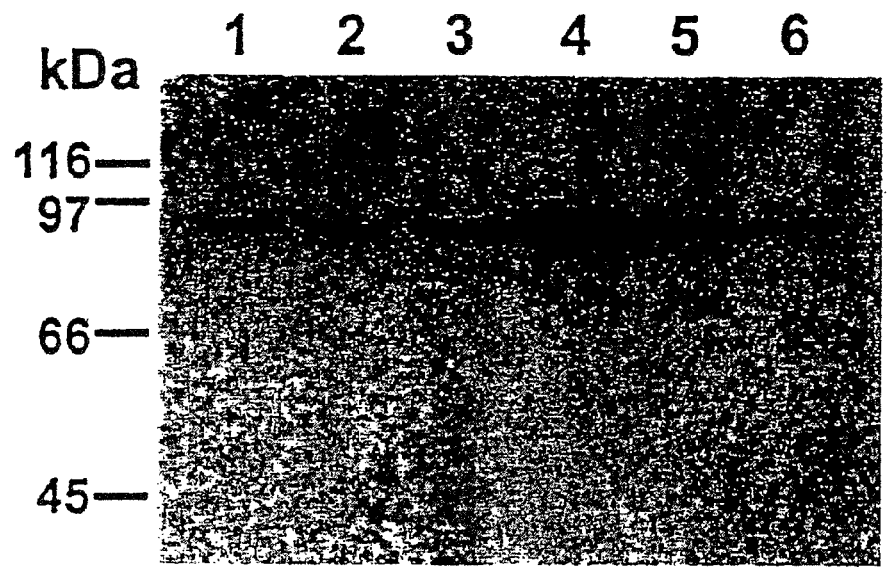
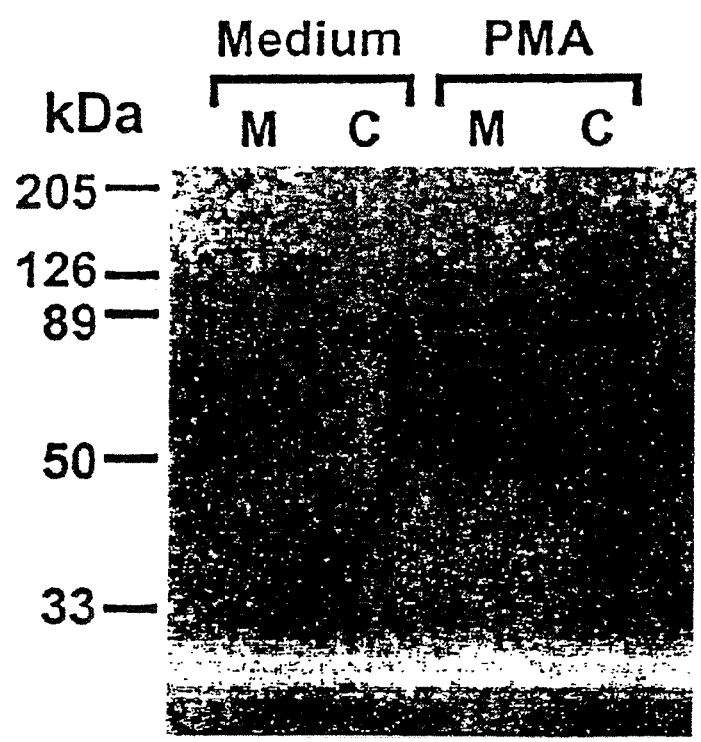
FIG. 4B

SEQUENCE LISTING

<160> NUMBER OF SEQ ID NOS: 20

<210> SEQ ID NO 1
<211> LENGTH: 24
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: Peptide may have an N-terminal myristate moiety

<400> SEQUENCE: 1

Gly Ala Gln Phe Ser Lys Thr Ala Ala Lys Gly Glu Ala Ala Ala Glu
1               5                   10                  15

Arg Pro Gly Glu Ala Ala Val Ala

-continued

```
                    20

<210> SEQ ID NO 2
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may have an N-terminal myristate moiety

<400> SEQUENCE: 2

Gly Thr Ala Pro Ala Ala Glu Gly Ala Gly Ala Glu Val Lys Arg Ala
1               5                   10                  15

Ser Ala Glu Ala Lys Gln Ala Phe
            20

<210> SEQ ID NO 3
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may have an N-terminal myristate moiety

<400> SEQUENCE: 3

Gly Ala Gln Phe Ser Lys Thr Ala Ala Lys Gly Glu Ala Ala Ala Glu
1               5                   10                  15

Arg Pro Gly Glu Ala Ala
            20

<210> SEQ ID NO 4
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may have an N-terminal myristate moiety

<400> SEQUENCE: 4

Gly Ala Gln Phe Ser Lys Thr Ala Ala Lys Gly Glu Ala Ala Ala Glu
1               5                   10                  15

Arg Pro Gly Glu Ala
            20

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may have an N-terminal myristate moiety

<400> SEQUENCE: 5

Gly Ala Gln Phe Ser Lys Thr Ala Ala Lys Gly Glu Ala Ala Ala Glu
1               5                   10                  15

Arg Pro Gly Glu
            20

<210> SEQ ID NO 6
```

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may have an N-terminal myristate moiety

<400> SEQUENCE: 6

Gly Ala Gln Phe Ser Lys Thr Ala Ala Lys Gly Glu Ala Ala Ala Glu
 1               5                  10                  15

Arg Pro Gly

<210> SEQ ID NO 7
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may have an N-terminal myristate moiety

<400> SEQUENCE: 7

Gly Ala Gln Phe Ser Lys Thr Ala Ala Lys Gly Glu Ala Ala Ala Glu
 1               5                  10                  15

Arg Pro

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may have an N-terminal myristate moiety

<400> SEQUENCE: 8

Gly Ala Gln Phe Ser Lys Thr Ala Ala Lys Gly Glu Ala Ala Ala Glu
 1               5                  10                  15

Arg

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may have an N-terminal myristate moiety

<400> SEQUENCE: 9

Gly Ala Gln Phe Ser Lys Thr Ala Ala Lys Gly Glu Ala Ala Ala Glu
 1               5                  10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may have an N-terminal myristate moiety

<400> SEQUENCE: 10
```

```
Gly Ala Gln Phe Ser Lys Thr Ala Ala Lys Gly Glu Ala Ala Ala
 1               5                  10                  15
```

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may have an N-terminal myristate moiety

<400> SEQUENCE: 11

```
Gly Ala Gln Phe Ser Lys Thr Ala Ala Lys Gly Glu Ala Ala
 1               5                  10
```

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may have an N-terminal myristate moiety

<400> SEQUENCE: 12

```
Gly Ala Gln Phe Ser Lys Thr Ala Ala Lys Gly Glu Ala
 1               5                  10
```

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may have an N-terminal myristate moiety

<400> SEQUENCE: 13

```
Gly Ala Gln Phe Ser Lys Thr Ala Ala Lys Gly Glu
 1               5                  10
```

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may have an N-terminal myristate moiety

<400> SEQUENCE: 14

```
Gly Ala Gln Phe Ser Lys Thr Ala Ala Lys Gly
 1               5                  10
```

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may have an N-terminal myristate moiety

<400> SEQUENCE: 15

```
Gly Ala Gln Phe Ser Lys Thr Ala Ala Lys
 1               5                  10
```

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may have an N-terminal myristate moiety

<400> SEQUENCE: 16

```
Gly Ala Gln Phe Ser Lys Thr Ala Ala
 1               5
```

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may have an N-terminal myristate moiety

<400> SEQUENCE: 17

```
Gly Ala Gln Phe Ser Lys Thr Ala
 1               5
```

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may have an N-terminal myristate moiety

<400> SEQUENCE: 18

```
Gly Ala Gln Phe Ser Lys Thr
 1               5
```

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may have an N-terminal myristate moiety

<400> SEQUENCE: 19

```
Gly Ala Gln Phe Ser Lys
 1               5
```

<210> SEQ ID NO 20
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may have an N-terminal myristate moiety

<400> SEQUENCE: 20

```
Gly Ala Gln Phe Ser Lys Thr Ala Ala Lys Gly Glu Ala Ala Glu
 1               5                  10                  15

Arg Pro Gly Glu Ala Ala Val
                20
```

METHODS FOR REGULATING INFLAMMATORY MEDIATORS AND PEPTIDES FOR USEFUL THEREIN

CROSS-REFERENCE TO RELATED APPLICATIONS

This application is a continuation application of U.S. patent application Ser. No. 11/367,449, filed on Mar. 6, 2006, now U.S. Pat. No. 7,544,772, which is a continuation-in-part application of U.S. patent application Ser. No. 10/802,644, filed on Mar. 17, 2004, now abandoned, which is a continuation application of U.S. patent application Ser. No. 10/180,753; filed Jun. 26, 2002, now abandoned, which claims priority to U.S. Provisional Application No. 60/300,933, filed Jun. 26, 2001, the disclosures of which are all incorporated herein by reference in their entirety.

STATEMENT OF FEDERAL SUPPORT

This invention was made with support from the United States Federal government under grant number R01 HL36982 from the National Institutes of Health. The United States government may have certain rights in this invention.

FIELD OF INVENTION

The present invention relates to methods of modulating cellular secretory processes. More specifically the present invention relates to modulating the release of inflammatory mediators. The present invention also relates to the intracellular signaling mechanism regulating the secretion of inflammatory mediators from membrane-bound vesicles or granules in inflammatory cells.

BACKGROUND OF THE INVENTION

Hypersecretion of mucus contributes to the pathogenesis of a large number of airway inflammatory diseases in both human and non-human animals. Increased mucus secretion is seen in chronic disease states such as asthma, COPD and chronic bronchitis; in genetic diseases such as cystic fibrosis; in allergic conditions (atopy, allergic inflammation); in bronchiectasis; and in a number of acute, infectious respiratory illnesses such as pneumonia, rhinitis, influenza or the common cold.

Accompanying hypersecretion of mucus in many of these respiratory diseases is the constant presence of inflammatory cells in the airways. These cells contribute greatly to the pathology of these diseases via the tissue damage done by the inflammatory mediators released from these cells. One example of such destruction via this chronic inflammation occurs in cystic fibrosis patients where mediators released from neutrophils (e.g., myeloperoxidase) induce the desquamation of the airway epithelial tissue.

Under-secretion of mucus also has harmful effects. Airway mucus acts as a physical barrier against biologically active inhaled particles, and may help prevent bacterial colonization of the airways and inactivate cytotoxic products released from leukocytes. King et al., *Respir. Physiol.* 62:47-59 (1985); Vishwanath and Ramphal, *Infect. Immun.* 45:197 (1984); Cross et al., *Lancet* 1:1328 (1984). In the eye, mucus maintains the tear film, and is important for eye health and comfort. Mucus secretion in the gastrointestinal tract also has a cytoprotective function. The role of mucus as a chemical, biological and mechanical barrier means that abnormally low mucus secretion by mucous membranes is undesirable.

Mammalian airways are lined by a thin layer of mucus produced and secreted by airway epithelial (goblet) cells and submucosal glands. In airway diseases such as asthma, chronic bronchitis, and cystic fibrosis, hypersecretion of mucus is a common symptom. Excess mucus can contribute to obstruction and susceptibility to infection. The major components of mucus are mucin glycoproteins synthesized by secretory cells and stored within cytoplasmic granules. Mucins are a family of glycoproteins secreted by the epithelial cells including those at the respiratory, gastrointestinal and female reproductive tracts. Mucins are responsible for the viscoelastic properties of mucus and at least eight mucin genes are known. Thornton, et al., *J. Biol. Chem.* 272, 9561-9566 (1997). Mucociliary impairment caused by mucin hypersecretion and/or mucus cell hyperplasia leads to airway mucus plugging that promotes chronic infection, airflow obstruction and sometimes death. Many airway diseases, such as chronic bronchitis, chronic obstructive pulmonary disease, bronchiectacis, asthma, cystic fibrosis and bacterial infections are characterized by mucin overproduction. E. Prescott, et al., *Eur. Respir. J.*, 8:1333-1338 (1995); K. C. Kim, et al., *Eur. Respir. J.*, 10:1438 (1997); D. Steiger, et al. *Am. J. Respir. Cell Mol. Biol.*, 12:307-314 (1995). Upon appropriate stimulation, mucin granules are released via an exocytotic process in which the granules translocate to the cell periphery where the granule membranes fuse with the plasma membrane, allowing for luminal secretion of the contents.

Despite the obvious pathophysiological importance of this process, intracellular signaling mechanisms linking stimulation at the cell surface to mucin granule release has only recently been elucidated. See, Li et al., *Journal of Biological Chemistry*, 276: 40982-40990 (2001). It is known that a wide variety of agents and inflammatory/humoral mediators provoke mucin secretion. These include cholinergic agonists, lipid mediators, oxidants, cytokines, neuropeptides, ATP and UTP, bacterial products, neutrophil elastase, and inhaled pollutants. See, Adler et al., *Res. Immunol.* 149, 245-248 (1998). Interestingly, many of these mucin secretagogues are also known to activate several protein kinases, and studies examining the regulation of excess secretion of mucin by airway epithelial cells from various species have consistently implicated involvement of either protein kinase C (PKC) or cGMP-dependent protein kinase (PKG) in the secretory process. See, e.g., Ko et al., *Am. J. Respir. Cell Mol. Biol.* 16, 194-198 (1997); Abdullah et al., *Am. J. Physiol.* 273, L201-L210 (1997); Abdullah et al., *Biochem. J.* 316, 943-954 (1996); Larivee et al. *Am. J. Respir. Cell Mol. Biol.* 11, 199-205 (1994); and Fischer et al., *Am. J. Respir. Cell Mol. Biol.* 20, 413-422 (1999). Coordinated interactions or "cross-talk" between these two protein kinases in regulation of mucin secretion has only recently been demonstrated to involve the MARCKS proteins. See, Li et al., *Journal of Biological Chemistry*, 276: 40982-40990 (2001). However, signaling events downstream of the coordinated action of these protein kinases that ultimately leads to the exocytotic release of mucin granules have not been fully elucidated.

MARCKS, a protein of approximately 82 kD, has three evolutionarily-conserved regions (Aderem et al., Nature 1988; 332:362-364; Thelen et al., Nature 1991; 351:320-322; Hartwig et al., Nature 1992; 356:618-622; Seykora et al., J Biol Chem 1996; 271:18797-18802): an N-terminus, a phosphorylation site domain (PSD), and a multiple homology 2 (MH2) domain. The N-terminus, a 24 amino acid sequence with a myristic acid moiety attached to a terminal glycine residue is involved in binding of MARCKS to membranes (Seykora et al., J Biol Chem 1996; 271:18797-18802) and possibly to calmodulin (Matsubara et al., J Biol Chem 2003; 278:48898-48902). This 24 amino acid sequence is known as the MANS peptide. The MANS peptide and active fragments thereof, can compete with native MARCKS in cells for membrane binding. Involvement of MARCKS protein in release of inflammatory mediators from the granules of infiltrating leukocytes is relevant to inflammation in diseases in all tissues and organs, including lung diseases characterized by airway inflammation, such as asthma, COPD and cystic fibrosis. However, inflammation and mucus secretion in the airways are two separate and independent processes (Li et al., J Biol Chem 2001; 276:40982-40990; Singer et al., Nat Med 2004; 10:193-196). While mucus production and secretion can be provoked by a number of factors, including mediators released by inflammatory cells, there is no known direct link between excess mucus and inflammation.

SUMMARY OF THE INVENTION

The invention relates to a new use for the 24 amino acid, myristoylated polypeptide, also known as the MANS peptide. The invention also relates to a new method for blocking any cellular secretory process, especially those that involve the release of inflammatory mediators from inflammatory cells, whose stimulatory pathways involve the protein kinase C (PKC) substrate MARCKS protein and release of contents from intracellular vesicles or granules.

The present invention is directed to a method of inhibiting the exocytotic release of at least one inflammatory mediator from at least one inflammatory cell comprising contacting the at least one inflammatory cell, which cell comprises at least one inflammatory mediator contained within a vesicle inside the cell, with at least one peptide selected from the group consisting of a MANS peptide and an active fragment thereof in an effective amount to reduce the release of the inflammatory mediator from the inflammatory cell as compared to the release of the inflammatory mediator from the same type of inflammatory cell that would occur in the absence of the at least one peptide.

The present invention is further directed to a method of inhibiting the release of at least one inflammatory mediator from at least one inflammatory cell in a tissue or fluid of a subject comprising the administration to the subject's tissue and/or fluid, which comprises at least one inflammatory cell comprising at least one inflammatory mediator contained within a vesicle inside the cell, a therapeutically effective amount of a pharmaceutical composition comprising at least one peptide selected from the group consisting of a MANS peptide and an active fragment thereof in a therapeutically effective amount to reduce the release of the inflammatory mediator from at least one inflammatory cell as compared to release of the inflammatory mediator from at least one of the same type of inflammatory cell that would occur in the absence of the at least one peptide. More specifically, inhibiting the release of an inflammatory mediator comprises blocking or reducing the release of an inflammatory mediator from the inflammatory cell.

More particularly, the present invention includes a method of reducing inflammation in a subject comprising the administration of a therapeutically effective amount of a pharmaceutical composition comprising a MANS peptide (i.e., N-myristoyl-GAQFSKTAAKGEAAAERPGEAAV (SEQ ID NO: 1)) or an active fragment thereof. The active fragment is at least six amino acids in length. As used herein, an "active fragment" of a MARCKS protein is one that affects (inhibits or enhances) the MARCKS protein-mediated release. An active fragment can be selected from the group consisting of N-myristoyl-GAQFSKTAAKGEAAAERPGEAA (SEQ ID NO: 3); N-myristoyl-GAQFSKTAAKGEAAAERPGEA (SEQ ID NO: 4); N-myristoyl-GAQFSKTAAKGEAAAER-PGE (SEQ ID NO: 5); N-myristoyl-GAQFSK-TAAKGEAAAERPG (SEQ ID NO: 6); N-myristoyl-GAQF-SKTAAKGEAAAERP (SEQ ID NO: 7); N-myristoyl-GAQFSKTAAKGEAAAER (SEQ ID NO: 8); N-myristoyl-GAQFSKTAAKGEAAAE (SEQ ID NO: 9); N-myristoyl-GAQFSKTAAKGEAAA (SEQ ID NO: 10); N-myristoyl-GAQFSKTAAKGEAA (SEQ ID NO: 11); N-myristoyl-GAQFSKTAAKGEA (SEQ ID NO: 12); N-myristoyl-GAQFSKTAAKGE (SEQ ID NO: 13); N-myristoyl-GAQFSKTAAKG (SEQ ID NO: 14); N-myristoyl-GAQFSKTAAK (SEQ ID NO: 15); N-myristoyl-GAQFSKTAA (SEQ ID NO: 16); N-myristoyl-GAQFSKTA (SEQ ID NO: 17); N-myristoyl-GAQFSKT (SEQ ID NO: 18); and N-myristoyl-GAQFSK (SEQ ID NO: 19). The presence of the hydrophobic N-terminal myristate moiety in these peptides can enhance their compatibility with and presumably their permeability to plasma membranes, and potentially enable the peptides to be taken up by cells. The hydrophobic insertion of myristate into a bilayer can provide a partition coefficient or apparent association constant with lipids of up to $10^4$ $M^{-1}$ or a unitary Gibbs free binding energy of about 8 kcal/mol (see, for example, Peitzsch, R. M., and McLaughlin, S. 1993, Binding of acylated peptides and fatty acids to phospholipid vesicles: pertinence to myristoylated proteins. Biochemistry. 32: 10436-10443) which is sufficient, at least in part, to permit a partitioning of the MANS peptide and of myristoylated MANS peptide fragments as described herein into the plasma membrane of a cell while additional functional groups and their interactions within the MANS peptide (which is myristoylated) and within myristoylated MANS peptide fragments can potentiate their relative membrane permeabilities. The fragments can each exhibit partition coefficients and membrane affinities that are representative of their respective structure. The fragments can be prepared by methods of peptide synthesis known in the art, such as by solid phase peptide synthesis (see, for example, the methods described in Chan, Weng C. and White, Peter D. Eds., Fmoc Solid Phase Peptide Synthesis: A Practical Approach, Oxford University Press, New York, N.Y. (2000); and Lloyd-Williams, P. et al. Chemical Approaches to the Synthesis of Peptides and Proteins (1997)) and purified by methods known in the art, such as by high pressure liquid chromatography. Molecular weight of each peptide can be confirmed by mass spectroscopy with each showing a peak with an appropriate molecular mass. Efficacy of the individual peptides and of combinations of individual peptides (for example, combinations of 2 of the peptides, combinations of 3 of the peptides, combinations of 4 of the peptides) in the methods of this disclosure can be readily determined without undue experimentation using the procedures described in the examples disclosed herein. A preferred combination will comprise two of the peptides; a preferred molar ratio of the peptides can be from 50:50 to 99.99 to 0.01, which ratio can be readily determined using the procedures described in the examples disclosed herein.

Preferably the MANS peptide or active fragment thereof is contained in a pharmaceutical composition which is useful to block inflammation. The present invention also includes methods for regulating a cellular secretory process in a subject comprising the administration of a therapeutically effective amount of a compound comprising a MANS peptide or an active fragment thereof, that regulates an inflammatory mediator in a subject. The administration is generally selected from the group consisting of topical administration, parenteral administration, rectal administration, pulmonary administration, inhalation and nasal or oral administration, wherein pulmonary administration generally includes either an aerosol, a dry powder inhaler, a metered dose inhaler, or a nebulizer.

Administration of a composition comprising a degranulation-inhibiting amount of the MANS peptide or a degranulation-inhibiting amount of an active fragment thereof, such as a pharmaceutical composition of the MANS peptide or an active fragment thereof, for human or animal use provides the MANS peptide or active fragment thereof at least to the site in or on a tissue or to a fluid-containing or mucus-containing layer in contact with the surface of a tissue where an inflammatory granulocytic cell resides or into which an inflammatory granulocytic cell will invade, thus enabling the MANS peptide or an active fragment thereof to contact the inflammatory granulocytic cell. In one aspect, administration of such a composition can be made at the first onset or first detection of inflammation or first perception of inflammation by the human or animal or at the first perceptible change in the level of inflammation in a human or animal to reduce the amount of inflammation that would otherwise occur in the absence of the MANS peptide or active fragment thereof. In another aspect, administration can be made during an ongoing inflammation of a tissue in the human or animal to reduce the amount of additional inflammation that would otherwise occur in the absence of the MANS peptide or active fragment thereof. While the amount and frequency of dose can be determined by clinical evaluation and be a function of the disease or source of inflammation and the extent of tissue involved and the age and size of the patient, it is anticipated that dosing of a pharmaceutical composition can be repeated after 3 to 8 hours, preferably after 6 to 8 hours after the first administration of the pharmaceutical composition.

The present invention also includes methods of reducing inflammation in a subject comprising the administration of a therapeutically effective amount of a compound that inhibits the MARCKS-related release of inflammatory mediators, whereby the release of at least one inflammatory mediator in the subject is reduced compared to that which would occur in the absence of said treatment. As used herein "reducing" generally means a lessening of the effects of inflammation. Preferably, inflammatory mediators are inhibited or blocked by the methods disclosed.

Another embodiment of the present invention includes methods of reducing inflammation in a subject comprising administering a therapeutically effective amount of a compound that inhibits the MARCKS-related release of inflammatory mediators, whereby the inflammation in the subject is reduced compared to that which would occur in the absence of said treatment. The present invention also discloses methods of reducing or inhibiting inflammation in a subject comprising the administration of a therapeutically effective amount of a MANS peptide or an active fragment thereof effective to modulate an inflammatory mediator at the inflammation site. The term "inhibiting" means a reduction in the amount of inflammatory mediator secretion. The term "completely inhibiting" means a reduction to zero in the amount of inflammatory mediator secretion. Again, as stated above, the active fragment is at least six amino acids in length. The term "exocytotic process" means exocytosis, i.e., a process of cellular secretion or excretion in which substances contained in a vesicle, which vesicle resides inside a cell, are discharged from the cell by fusion of the vesicular membrane of the vesicle with the outer cell membrane. "Degranulation" means the release of cellular granule contents. The term "degranulation-inhibiting" means a reduction in the release of the inflammatory mediators contained within the granules of the inflammatory cell. Thus, a degranulation-inhibiting amount of the MANS peptide and/or an active fragment thereof is the amount of these peptides that is sufficient to reduce the release of the inflammatory mediators contained in the granules as compared to release in the absence of the same peptide.

MANS peptide and active fragments thereof can be useful in the prevention or reduction in amount of inflammation in a tissue in an animal caused by inflammatory mediators. MANS peptide and active fragments thereof can be useful in the prevention or reduction in amount of tissue damage in an animal produced or caused by inflammatory mediators.

BRIEF DESCRIPTION OF THE DRAWINGS

FIGS. 4A-4B illustrate that PKC-dependent phosphorylation releases MARCKS from the plasma membrane to the cytoplasm.

DETAILED DESCRIPTION OF THE INVENTION

Figure 1A:
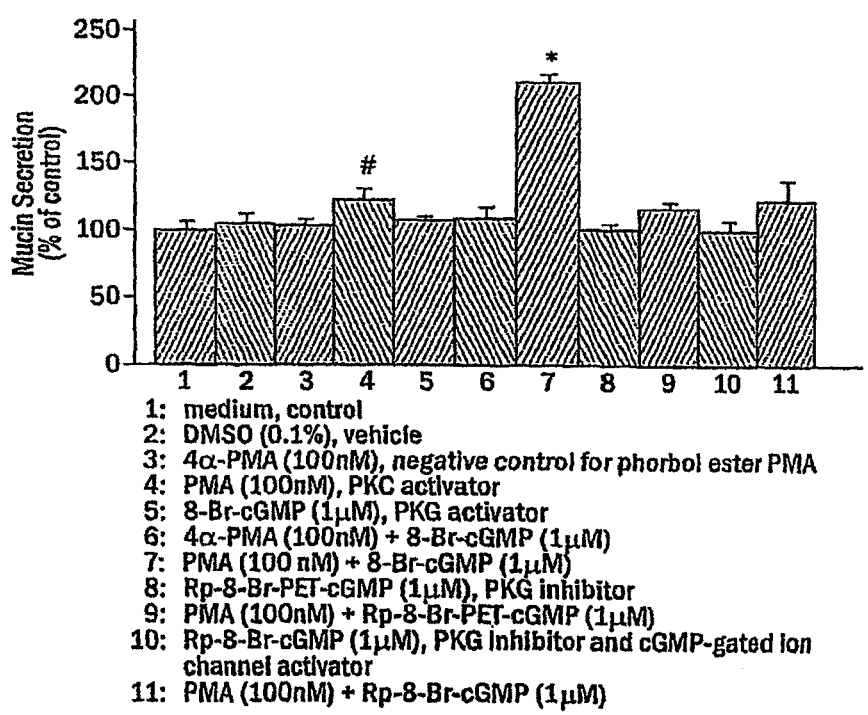
FIGS. 1A-1D are bar graphs illustrating mucin hypersecretion by NHBE cells is maximized by activation of both PKC and PKG.

The present invention will now be described more fully hereinafter with reference to the accompanying figures, in which preferred embodiments of the invention are illustrated. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. The use of the words "a" or "an" herein to describe any aspect of the present invention is to be interpreted as indicating one or more.

The present invention is directed to a method of inhibiting the exocytotic release of at least one inflammatory mediator from at least one inflammatory cell comprising contacting the at least one inflammatory cell, which cell comprises at least one inflammatory mediator contained within a vesicle inside the cell, with at least one peptide selected from the group consisting of a MANS peptide and an active fragment thereof in an effective amount to reduce the release of the inflammatory mediator from the inflammatory cell as compared to the release of the inflammatory mediator from the same type of inflammatory cell that would occur in the absence of the at least one peptide.

The present invention is further directed to a method of inhibiting the release of at least one inflammatory mediator from at least one inflammatory cell in a tissue or fluid of a subject comprising the administration to the subject's tissue and/or fluid, which comprises at least one inflammatory cell comprising at least one inflammatory mediator contained within a vesicle inside the cell, a therapeutically effective amount of a pharmaceutical composition comprising at least one peptide selected from the group consisting of a MANS peptide and an active fragment thereof in a therapeutically effective amount to reduce the release of the inflammatory mediator from at least one inflammatory cell as compared to release of the inflammatory mediator from at least one of the same type of inflammatory cell that would occur in the absence of the at least one peptide. More specifically, reducing the release of an inflammatory mediator comprises blocking or inhibiting the mechanism that releases an inflammatory mediator from the inflammatory cell.

The MANS peptide used in the present methods described above comprises SEQ ID NO:1. The active fragment useful in the present invention comprises at least one myristoylated N-terminal fragment of SEQ ID NO:1 which comprises at least six amino acids, wherein the first amino acid of said fragment begins at the N-terminal glycine of SEQ ID NO:1. More specifically, the active fragment can be selected from the group consisting of N-myristoyl-GAQFSK-TAAKGEAAAERPGEAA (SEQ ID NO: 3); N-myristoyl-GAQFSKTAAKGEAAAERPGEA (SEQ ID NO: 4); N-myristoyl-GAQFSKTAAKGEAAAERPGE (SEQ ID NO: 5); N-myristoyl-GAQFSKTAAKGEAAAERPG (SEQ ID NO: 6); N-myristoyl-GAQFSKTAAKGEAAAERP (SEQ ID NO: 7); N-myristoyl-GAQFSKTAAKGEAAAER (SEQ ID NO: 8); N-myristoyl-GAQFSKTAAKGEAAAE (SEQ ID NO: 9); N-myristoyl-GAQFSKTAAKGEAAA (SEQ ID NO: 10); N-myristoyl-GAQFSKTAAKGEAA (SEQ ID NO: 11); N-myristoyl-GAQFSKTAAKGEA (SEQ ID NO: 12); N-myristoyl-GAQFSKTAAKGE (SEQ ID NO: 13); N-myristoyl-GAQFSKTAAKG (SEQ ID NO: 14); N-myristoyl-GAQFSKTAAK (SEQ ID NO: 15); N-myristoyl-GAQFSKTAA (SEQ ID NO: 16); N-myristoyl-GAQFSKTA (SEQ ID NO: 17); N-myristoyl-GAQFSKT (SEQ ID NO: 18); and N-myristoyl-GAQFSK (SEQ ID NO: 19).

The present invention is directed to the contact and/or administration of the peptide described above and throughout the specification with any known inflammatory cell that may be contained in the tissue or fluid of a subject which contains at least one inflammatory mediator contained within a vesicle inside the cell. The inflammatory cell is preferably a leukocyte, more preferably a granulocyte, which can be further classified as a neutrophil, a basophil, an eosinophil or a combination thereof. The inflammatory cells contacted in the present method may also be a monocyte/macrophage.

The present invention is directed to reducing the release of inflammatory mediators contained within the vesicles of inflammatory cells and these inflammatory mediators are selected from the group consisting of myeloperoxidase (MPO), eosinophil peroxidase (EPO), major basic protein (MBP), lysozyme, granzyme, histamine, proteoglycan, protease, a chemotactic factor, cytokine, a metabolite of arachidonic acid, defensin, bactericidal permeability-increasing protein (BPI), elastase, cathepsin G, cathepsin B, cathepsin D, beta-D-glucuronidase, alpha-mannosidase, phospholipase $A_2$, chondroitin-4-sulphate, proteinase 3, lactoferrin, collagenase, complement activator, complement receptor, N-formylmethionyl-leucyl-phenylalanine (FMLP) receptor, laminin receptor, cytochrome $b_{558}$, monocyte-chemotactic factor, histaminase, vitamin B12 binding protein, gelatinase, plasminogen activator, beta-D-glucuronidase, and a combination thereof. Preferably, these inflammatory mediators are selected from the group consisting of myeloperoxidase (MPO), eosinophil peroxidase (EPO), major basic protein (MBP), lysozyme, granzyme and a combination thereof.

The present invention contacts an effective amount of the peptide with an inflammatory cell, wherein the effective amount is defined as a degranulation-inhibiting amount of MANS peptide or an active fragment thereof that reduces the amount of an inflammatory mediator released from at least one inflammatory cell from about 1% to about 99% as compared to the amount released from at least one inflammatory cell in the absence of MANS peptide or an active fragment thereof. More preferably, this effective amount of the contacted peptide comprises a degranulation-inhibiting amount of MANS peptide or an active fragment thereof that reduces the amount of an inflammatory mediator released from at least one inflammatory cell from between about 5-50% to about 99% as compared to the amount released from at least one inflammatory cell in the absence of MANS peptide or an active fragment thereof.

The present invention in one embodiment is directed to the administration of at least one peptide comprising a MANS peptide and an active fragment thereof in a therapeutically effective amount into tissue or fluid of a subject where the subject is afflicted by a respiratory disease, which is preferably asthma, chronic bronchitis or COPD. In a further embodiment, the subject may be afflicted by a bowel disease, a skin disease, an autoimmune disease, a pain syndrome, and combinations thereof. The bowel disease may be ulcerative colitis, Crohn's disease or irritable bowel syndrome. The subject may be afflicted with a skin disease, such as rosacea, eczema, psoriasis or severe acne. The subject may also be afflicted with arthritis, such as rheumatoid arthritis, psoriatic arthritis, systemic lupus erythematosus. Subjects afflicted by cystic fibrosis may also be treated by the present method and peptides. The present method is preferably useful for the treatment of subjects, such as mammals, and preferably humans, canines, equines and felines.

The present method of treatment of subjects is by the administration of one or more peptides including the MANS peptide or an active fragment described herein to include topical administration, parenteral administration, rectal administration, pulmonary administration, nasal administration, or oral administration. More specifically, pulmonary administration is selected from the group of aerosol, dry powder inhaler, metered dose inhaler, and nebulizer. Additionally, the disclosed method may further comprise the administration to the subject of a second molecule selected from the group consisting of an antibiotic, an antiviral compound, an antiparasitic compound, an anti-inflammatory compound, and an immunosuppressant.

In one aspect, the invention relates to a method of administering a pharmaceutical composition. The pharmaceutical composition comprises a therapeutically effective amount of a known compound and a pharmaceutically acceptable carrier. A "therapeutically effective" amount as used herein is an amount of a compound that is sufficient to ameliorate symptoms exhibited by a subject. The therapeutically effective amount will vary with the age and physical condition of the patient, the severity of the condition of the patient being treated, the duration of the treatment, the nature of any concurrent treatment, the pharmaceutically acceptable carrier used and like factors within the knowledge and expertise of those skilled in the art. Pharmaceutically acceptable carriers are preferably solid dosage forms such as tablets or capsules. Liquid preparations for oral administration also may be used and may be prepared in the form of syrups or suspensions, e.g., solutions containing an active ingredient, sugar, and a mixture of ethanol, water, glycerol, and propylene glycol. If desired, such liquid preparations may include one or more of following: coloring agents, flavoring agents, and saccharin. Additionally, thickening agents such as carboxymethylcellulose also may be used as well as other acceptable carriers, the selection of which are known in the art.

As stated above, the present invention relates to methods for regulating cellular secretory processes, especially those releasing inflammatory mediators from inflammatory cells. As used herein, the term "regulating" means blocking, inhibiting, decreasing, reducing, increasing, enhancing or stimulating. A number of cellular secretory processes involve the release of contents from membrane-bound vesicles or granules within cells A membrane-bound vesicle or granule is defined as an intracellular particle, which is primarily vesicular (or a vesicle inside a cell) and which contains stored material that can be secreted. Some of the contents of these vesicles, such as those contained in inflammatory cells, have been found to be responsible for a variety of pathologies in numerous mammalian tissues. Some of the effects of these secretions appear to include damage of previously healthy tissue during inflammation. This invention provides a means of blocking secretion from any membrane-bound vesicle, including those found in inflammatory cells, by targeting a specific molecule important in the intracellular secretory pathway with a synthetic peptide. This approach may be of therapeutic importance for the treatment of a wide variety of hypersecretory and inflammatory conditions in humans and animals.

More specifically, the present invention targets inflammatory cells that contain the inflammatory mediators in one or more granules or vesicles within the cells' cytoplasm. The cells are contacted with one or more peptides that are selected from the MANS peptide or an active fragment thereof, all of which are described in detail herein. Preferably the contact of the peptide with the inflammatory cell is via administration to a subject afflicted by or suffering from a disease in which these inflammatory cells are present in specific tissue or fluid within the tissue. Upon administration or contact of the peptide with the cell, the peptide competitively competes for and competitively inhibits the binding of the native MARCKS protein to the membrane of the intracellular granules or vesicles which contain the inflammatory mediators. As a result of blocking the binding of the MARCKS protein to the vesicles in the inflammatory cells, these vesicles in these cells do not move to the plasma membrane of the cells as they would normally do when stimulated to exocytotically release their contents of inflammatory mediators out of the cells. Thus, the method of the present invention inhibits the movement of the vesicles to the cells' plasma membrane, which in turn, reduces the release of the inflammatory mediators from the inflammatory cells. The amount of inflammatory mediators released from the cells over time is reduced because both the rate of release and the amount of release of the mediators from the inflammatory cells is dependent upon the concentration of the peptide administered and contacted with the inflammatory cells.

One benefit of the present invention is that it may combine a therapy that includes the direct blocking of mucus secretion with a unique anti-inflammatory therapy. A benefit of the present invention over current anti-inflammation therapies that affect a general suppression of the immune system is that the peptide is thought to block secretion of only intracellular components secreted from inflammatory cells. Thus, many aspects of the immune system should still function even with the inhibition of the inflammatory mediators.

The compounds of the invention may regulate, i.e. block, inflammatory mediator release from cells. This inhibition of release of inflammatory mediators is an attractive means for preventing and treating a variety of disorders, e.g., diseases and pathological conditions involving inflammation. Thus, the compounds of the invention may be useful for the treatment of such conditions. These encompass airway diseases and chronic inflammatory diseases including, but not limited to, osteoarthritis, multiple sclerosis, Guillain-Barre syndrome, Crohn's disease, ulcerative colitis, psoriasis, graft versus host disease, systemic lupus erythematosus and insulin-dependent diabetes mellitus. The compounds of the invention can also be used to treat other disorders associated with the activity of elevated levels of proinflammatory mediators and enzymes such as responses to various infectious agents and a number of diseases of autoimmunity such as rheumatoid arthritis, toxic shock syndrome, diabetes and inflammatory bowel diseases.

Uses of the peptide and methods of the invention include therapies to combat inflammation along with therapies that will combine the anti-inflammatory activity of the peptide with its ability to block mucus secretion. Diseases that may be treated by the peptide's ability to block both inflammation and mucus secretion include but are not limited to inflammatory bowel diseases, digestive disorders (i.e., inflamed gall bladder, Menetier's disease) and inflammatory airway diseases. The peptide may also be used to block release of excess insulin from pancreatic islet cells.

Other proinflammatory mediators have been correlated with a variety of disease states that correlate with influx of neutrophils into sites of inflammation or injury. Blocking antibodies have been demonstrated as useful therapies against the neutrophil-associated tissue injury in acute inflammation (Harada et al., 1996, *Molecular Medicine Today* 2, 482). Cells other than neutrophils that may release inflammatory mediators include other leukocytes, such as basophils, eosinophils, monocytes and lymphocytes, and therapies may be directed against secretion from these cells. Neutrophils, eosinophils, and basophils are each a type of granulocyte, i.e., a leukocyte that has granules in its cytoplasm. Leukocytes synthesize a number of inflammatory mediators that are packaged and stored in cytoplasmic granules. Among these mediators are, for example, myeloperoxidase [MPO] in neutrophils (Borregaard N, Cowland J B. Granules of the human neutrophilic polymorphonuclear leukocyte. Blood 1997; 89:3503-3521), eosinophil peroxidase [EPO] and major basic protein [MBP] in eosinophils (Gleich G J. Mechanisms of eosinophil-associated inflammation. J Allergy Clin Immunol 2000; 105:651-663), lysozyme in monocytes/macrophages (Hoff T, Spencker T, Emmendoerffer A., Goppelt-Struebe M. Effects of glucocorticoids on the TPA-induced monocytic differentiation. J Leukoc Biol 1992; 52:173-182; Balboa M A, Saez Y, Balsinde J. Calcium-independent phospholipase A2 is required for lysozyme secretion in U937 promonocytes. J Immunol 2003; 170:5276-5280), and granzyme in natural killer (NK) cells and cytotoxic lymphocytes (Bochan M R, Goebel W S, Brahmi Z. Stably transfected antisense granzyme B and perforin constructs inhibit human granule-mediated lytic ability. Cell Immunol 1995; 164:234-239; Gong J H., Maki G, Klingemann H G. Characterization of a human cell line (NK-92) with phenotypical and functional characteristics of activated natural killer cells. Leukemia 1994; 8:652-658; Maki G, Klingemann H G, Martinson J A, Tam Y K. Factors regulating the cytotoxic activity of the human natural killer cell line, NK-92. J Hematother Stem Cell Res 2001; 10:369-383; and Takayama H, Trenn G, Sitkovsky M V. A novel cytotoxic T lymphocyte activation assay. J Immunol Methods 1987; 104:183-1907-10). These mediators can be released at sites of injury and can contribute to inflammation and repair, such as in the lung and elsewhere, as a result of the infiltration of these cells to the tissue site of injury or disease. Leukocytes release these granules via an exocytotic mechanism (Burgoyne R D, Morgan A. Secretory granule exocytosis. Physiol Rev 2003; 83:581-632; Logan M R, Odemuyiwa S O, Moqbel R. Understanding exocytosis in immune and inflammatory cells: the molecular basis of mediator secretion. J Allergy Clin Immunol 2003; 111: 923-932), Mast cells, which usually do not circulate in the blood stream, and basophils contain secretory cytoplasmic granules which store and can release, upon cell activation, preformed inflammatory (anaphylactic) mediators, such as histamine; proteoglycans, such as heparin and chondroitin sulphate; proteases such as tyrptase, chymase, carboxypeptidase, and cathepsin G-like protease; chemotactic factors, cytokines and metabolites of arachidonic acid that act on the vasculature, smooth muscle, connective tissue, mucous glands and inflammatory cells.

Neutrophils, also known as polymorphonuclear leukocytes (PMN), comprise 50 to 60% of the total circulating leukocytes. Neutrophils act against infectious agents, such as bacteria, fungi, protozoa, viruses, virally infected cells, as well as tumor cells, that penetrate the body's physical barriers at sites of infection or injury. Neutrophils mature through six morphological stages: myeloblast, promyeloblast, myelocyte, metamyelocyte, non-segmented (band) neutrophil, and segmented (functionally active) neutrophil.

In neutrophils, inflammatory mediators are stored in primary (azurophil), secondary (specific), and tertiary (gelatinase) granules, as well as in secretory vesicles. Among numerous mediators of inflammation, primary (azurophil) granules contain myeloperoxidase (MPO), lysozyme, defensins, bactericidal permeability-increasing protein (BPI), elastase, cathepsin G, cathepsin B, cathepsin D, beta-D-glucuronidase, alpha-mannosidase, phospholipase $A_2$, chondroitin-4-sulphate, and proteinase 3 (see, for example, Hartwig J H, Thelen M, Rosen A, Janmey P A, Nairn A C, Aderem A. MARCKS is an actin filament crosslinking protein regulated by protein kinase C and calcium-calmodulin. Nature 1992; 356:618-622); secondary (specific) granules contain lysozyme, lactoferrin, collagenase, complement activator, phospholipase $A_2$, complement receptors, e.g., CR3, CR4, N-formylmethionyl-leucyl-phenylalanine (FMLP) receptors, laminin receptors, cytochrome $b_{558}$, monocyte-chemotactic factor, histaminase, and vitamin B12 binding protein; and small storage granules contain gelatinase, plasminogen activator, cathepsin B, cathepsin D, beta-D-glucuronidase, alpha-mannosidase, and cytochrome $b_{558}$.

Neutrophil granules contain antimicrobial or cytotoxic substances, neutral proteinases, acid hydrolases and a pool of cytoplasmic membrane receptors. Among azurophil granule constituents myeloperoxidase (MPO) is a critical enzyme in the conversion of hydrogen peroxide to hypochlorous acid. Together with hydrogen peroxide and a halide cofactor it forms an effective microbicidal and cytotoxic mechanism of leukocytes—the myeloperoxidase system.

Defensins, which constitute 30 to 50% of azurophilic granule protein, are small (molecule weight<4000) potent antimicrobial peptides that are cytotoxic to a broad range of bacteria, fungi and some viruses. Their toxicity may be due to membrane permeabilization of the target cell which is similar to other channel-forming proteins (perforins).

Bacterial permeability-increasing (BPI) protein is a member of perforins. It is highly toxic to gram-negative bacteria but not to gram-positive bacteria or fungi and can also neutralize endotoxin, the toxic lipopolysaccharide component of gram-negative bacterial cell envelope.

Lactoferrin sequesters free iron, thereby preventing the growth of ingested microorganisms that survive the killing process and increases bacterial permeability to lysozyme.

Serine proteases such as elastase and cathepsin G hydrolyze proteins in bacterial cell envelopes. Substrates of granulocyte elastase include collagen cross-linkages and proteoglycans, as well as elastin components of blood vessels, ligaments, and cartilage. Cathepsin D cleaves cartilage proteoglycans, whereas granulocyte collagenases are active in cleaving type I and, to a lesser degree, type III collagen from bone, cartilage, and tendon. Collagen breakdown products have chemotactic activity for neutrophils, monocytes, and fibroblasts.

Regulation of tissue destructive potential of lysosomal proteases is mediated by protease inhibitors such as alpha2-macroglobulin and alpha1-antiprotease. These antiproteases are present in serum and synovial fluids. They may function by binding to and covering the active sites of proteases. Protease-antiprotease imbalance can be important in the pathogenesis of emphysema.

Azurophil granules function predominantly in the intracellular milieu (in the phagolysosomal vacuole), where they are involved in the killing and degradation of microorganisms. Neutrophil specific granules are susceptible to release their contents extracellularly and have an important role in initiating inflammation. Specific granules represent an intracellular reservoir of various plasma membrane components including cytochrome b (component of NADPH oxidase, an enzyme responsible for the production of superoxide), receptors for complement fragment iC3b (CR3, CR4), for laminin, and formylmethionyl-peptide chemoattractants. In addition to others, there is histaminase which is relevant for the degradation of histamine, vitamin binding protein, and plasminogen activator which is responsible for plasmin formation and cleavage of C5a from C5.

The importance of neutrophil granules in inflammation is apparent from studies of several patients with congenital abnormalities of the granules. Patients with Chédiak-Higashi syndrome have a profound abnormality in the rate of establishment of an inflammatory response and have abnormally large lysosomal granules. The congenital syndrome of specific granule deficiency is an exceedingly rare disorder characterized by diminished inflammatory responses and severe bacterial infections of skin and deep tissues.

Although mechanisms regulating exocytotic secretion of these granules are only partially understood, several key molecules in the process have been identified, including intracellular Ca2+ transients (Richter et al. Proc Natl Acad Sci USA 1990; 87:9472-9476; Blackwood et al., Biochem J 1990; 266:195-200), G proteins, tyrosine and protein kinases (PK, especially PKC) (Smolen et al., Biochim Biophys Acta 1990; 1052:133-142; Niessen et al., Biochim. Biophys. Acta 1994; 1223:267-273; Naucler et al., Pettersen et al., Chest 2002; 121; 142-150), Rac2 (Abdel-Latif et al., Blood 2004; 104: 832-839; Lacy et al., J Immunol 2003; 170:2670-2679) and various SNARE's, SNAP's and VAMP's (Sollner et al., Nature 1993; 362: 318-324; Lacy, Pharmacol Ther 2005; 107:358-376).

SNARE (Soluble N-ethylmaleimide attachment protein receptor) proteins are a family of membrane-associated proteins characterized by an alpha-helical coiled-coil domain called the SNARE motif (Li et al., Cell. Mol. Life. Sci. 60: 942-960 (2003)). These proteins are classified as v-SNAREs and t-SNAREs based on their localization on vesicle or target membrane; another classification scheme defines R-SNAREs and Q-SNAREs, as based on the conserved arginine or glutamine residue in the centre of the SNARE motif. SNAREs are localized to distinct membrane compartments of the secretory and endocytic trafficking pathways, and contribute to the specificity of intracellular membrane fusion processes. The t-SNARE domain consists of a 4-helical bundle with a coiled-coil twist. The SNARE motif contributes to the fusion of two membranes. SNARE motifs fall into four classes: homologues of syntaxin 1a (t-SNARE), VAMP-2 (v-SNARE), and the N- and C-terminal SNARE motifs of SNAP-25. One member from each class may interact to form a SNARE complex. The SNARE motif is found in the N-terminal domains of certain syntaxin family members such as syntaxin 1a, which is required for neurotransmitter release (Lerman et al., Biochemistry 39: 8470-8479 (2000)), and syntaxin 6, which is found in endosomal transport vesicles (Misura et al., Proc. Natl. Acad. Sci. U.S.A. 99: 9184-9189 (2002)).

SNAP-25 (synaptosome-associated protein 25 kDa) proteins are components of SNARE complexes, which may account for the specificity of membrane fusion and to directly execute fusion by forming a tight complex (the SNARE or core complex) that brings the synaptic vesicle and plasma membranes together. The SNAREs constitute a large family of proteins that are characterized by 60-residue sequences known as SNARE motifs, which have a high propensity to form coiled coils and often precede carboxy-terminal transmembrane regions. The synaptic core complex is formed by four SNARE motifs (two from SNAP-25 and one each from synaptobrevin and syntaxin 1) that are unstructured in isolation but form a parallel four-helix bundle on assembly. The crystal structure of the core complex has revealed that the helix bundle is highly twisted and contains several salt bridges on the surface, as well as layers of interior hydrophobic residues. A polar layer in the centre of the complex is formed by three glutamines (two from SNAP-25 and one from syntaxin 1) and one arginine (from synaptobrevin) (Rizo et al., Nat Rev Neurosci 3: 641-653 (2002)). Members of the SNAP-25 family contain a cluster of cysteine residues that can be palmitoylated for membrane attachment (Risinger et al., J. Biol. Chem. 268: 24408-24414 (1993)).

The major role of neutrophils is to phagocytose and destroy infectious agents. They also limit the growth of some microbes, prior to onset of adaptive (specific) immunological responses. Although neutrophils are essential to host defense, they have also been implicated in the pathology of many chronic inflammatory conditions and in ischemia-reperfusion injury. Hydrolytic enzymes of neutrophil origin and oxidatively inactivated protease inhibitors can be detected in fluid isolated from inflammatory sites. Under normal conditions, neutrophils can migrate to sites of infection without damage to host tissues. However, undesirable damage to a host tissue can sometimes occur. This damage may occur through several independent mechanisms. These include premature activation during migration, extracellular release of toxic products during the killing of some microbes, removal of infected or damage host cells and debris as a first step in tissue remodeling, or failure to terminate acute inflammatory responses. Ischemia-reperfusion injury is associated with an influx of neutrophils into the affected tissue and subsequent activation. This may be triggered by substances released from damaged host cells or as a consequence of superoxide generation through xantine oxidase.

Under normal conditions, blood may contain a mixture of normal, primed, activated and spent neutrophils. In an inflammatory site, mainly activated and spent neutrophils are present. Activated neutrophils have enhanced production of reactive oxygen intermediates (ROI). A subpopulation of neutrophils with the enhanced respiratory burst has been detected in the blood of people with an acute bacterial infection and patients with the adult respiratory distress syndrome (ARDS). This is an example of a neutrophil paradox. Neutrophils have been implicated in the pathology of this condition because of the large influx of these cells into the lung and the associated tissue damage caused by oxidants and hydrolytic enzymes released from activated neutrophils. The impairment of neutrophil microbicidal activity that occurs as the ARDS worsens may be a protective response on the part of the host, which is induced locally by inflammatory products.

The acute phase of thermal injury is also associated with neutrophil activation, and this is followed by a general impairment in various neutrophil functions. Activation of neutrophils by immune complexes in synovial fluid contributes to the pathology of rheumatoid arthritis. Chronic activation of neutrophils may also initiate tumor development because some ROI generated by neutrophils damage DNA and proteases promote tumor cell migration. In patients suffering from severe burns, a correlation has been established between the onset of bacterial infection and reduction in the proportion and absolute numbers of neutrophils positive for antibody and complement receptors. Oxidants of neutrophil origin have also been shown to oxidize low-density lipoproteins (LDL), which are then more effectively bound to the plasma membrane of macrophages through specific scavenger receptors. Uptake of these oxidized LDL by macrophages may initiate atherosclerosis. In addition, primed neutrophils have been found in people with essential hypertension, Hodgkin's disease, inflammatory bowel disease, psoriasis, sarcoidosis, and septicemia, where priming correlates with high concentrations of circulating TNF-alpha (cachectin).

Hydrolytic damage to host tissue and therefore chronic inflammatory conditions may occur when antioxidant and antiprotease screens are overwhelmed. Antiprotease deficiency is thought to be responsible for the pathology of emphysema. Many antiproteases are members of the serine protease inhibitor (SERPIN) family. Although the circulation is rich in antiproteases, these large proteins may be selectively excluded at sites of inflammation because neutrophils adhere to their targets. Oxidative stress may initiate tissue damage by reducing the concentration of extracellular antiproteases to below the level required to inhibit released proteases. Chlorinated oxidants and hydrogen peroxide can inactivate antiproteases such as alpha1-protease inhibitor and alpha2-macroglobulin, which are endogenous inhibitors of elastase, but simultaneously activate latent metalloproteases such as collagenases and gelatinase, which contribute to the further inactivation of antiproteases.

Cytoplasmic constituents of neutrophils may also be a cause of formation of specific anti-neutrophil cytoplasmic antibodies (ANCA), which are closely related to the development of systemic vasculitis and glomerulonephritis. ANCA are antibodies directed against enzymes that are found mainly within the azurophil or primary granules of neutrophils. There are three types of ANCA that can be distinguished by the patterns they produce by indirect immunofluorescence on normal ethanol-fixed neutrophils. Diffuse fine granular cytoplasmic fluorescence (cANCA) is typically found in Wegener's granulomatosis, in some cases of microscopic polyarteritis and Churg Strauss syndrome, and in some cases of crescentic and segmental necrotizing glomerulonephritis. The target antigen is usually proteinase 3. Perinuclear fluorescence (pANCA) is found in many cases of microscopic polyarteritis and glomerulonephritis. These antibodies are often directed against myeloperoxidase but other targets include elastase, cathepsin G, lactoferrin, lysozyme and beta-D-glucuronidase. The third group designated "atypical" ANCA includes neutrophil nuclear fluorescence and some unusual cytoplasmic patterns and while a few of the target antigens are shared with pANCA, the others have not been identified yet. pANCA are also found in a third of patients with Crohn's disease. The reported incidence of ANCA in rheumatoid arthritis and SLE varies considerably but the patterns are predominantly pANCA and atypical ANCA.

The eosinophil is a terminally differentiated, end-stage leukocyte that resides predominantly in submucosal tissue and is recruited to sites of specific immune reactions, including allergic diseases. The eosinophil cytoplasm contains large ellipsoid granules with an electron-dense crystalline nucleus and partially permeable matrix. In addition to these large primary crystalloid granules, there is another granule type that is smaller (small granule) and lacks the crystalline nucleus. The large specific granules of eosinophils contain at least four distinct cationic proteins, which exert a range of biological effects on host cells and microbial targets: major basic protein (MBP), eosinophil cationic protein (ECP), eosinophil derived neurotoxin (EDN), and eosinophil peroxidase (EPO). Basophils contain about one fourth as much major basic protein as eosinophils together with detectable amounts of EDN, ECP and EPO. Small amounts of EDN and ECP are also found in neutrophils (Gleich G J. Mechanisms of eosinophil-associated inflammation. J Allergy Clin Immunol 2000; 105:651-663). MBP appears to lack enzymatic activity but is a highly cationic polypeptide which may exert its toxic activities by interactions with lipid membranes leading to their derangement. Both MBP and EPO can act as selective allosteric inhibitors of agonist binding to M2 muscarinic receptors. These proteins may contribute to M2 receptor dysfunction and enhance vagally mediated bronchoconstriction in asthma. EDN can specifically damage the myelin coat of neurons. Histaminase and a variety of hydrolytic lysosomal enzymes are also present in the large specific granules of eosinophils. Among the enzymes in small granules of eosinophils are aryl sulphatase, acid phosphatase, and a 92 kDa metalloproteinase, a gelatinase. Eosinophils can elaborate cytokines which include those with potential autocrine growth-factor activities for eosinophils and those with potential roles in acute and chronic inflammatory responses. Three cytokines have growth-factor activities for eosinophils: granulocyte-macrophage colony-stimulating factor (GM-CSF), IL-3 and IL-5. Other cytokines produced by human eosinophils that may have activities in acute and chronic inflammatory responses include IL-1-alpha, IL-6, IL-8, TNF-alpha and both transforming growth factors, TGF-alpha and TGF-beta.

Eosinophils contain crystalloid granules that contain MBP, eosinophil cationic protein, EPO, and eosinophil-derived neurotoxin (Gleich, J Allergy Clin Immunol 2000; 105:651-663). The human promyelocytic cell line HL-60 clone 15 can be used to examine secretion of EPO. This cell line was established from a clone of HL-60 that had been grown at an elevated pH for two months (Fischkoff, Leuk Res 1988; 12:679-686) and then treated with butyric acid to allow the cells to differentiate so as to exhibit many of the characteristics of peripheral blood eosinophils, including expression of eosinophil-specific granule proteins (Rosenberg et al., J Exp Med 1989; 170:163-176; Tiffany et al., J Leukoc Biol 1995; 58:49-54; Badewa et al., Exp Biol Med 2002; 227:645-651).

Eosinophils can participate in hypersensitivity reactions, especially through two lipid inflammatory mediators, leukotriene $C^4$ ($LTC^4$) and platelet activating factor (PAF). Both mediators contract airway smooth muscle, promote the secretion of mucus, alter vascular permeability and elicit eosinophil and neutrophil infiltration. In addition to the direct activities of these eosinophil-derived mediators, MBP can stimulate the release of histamine from basophils and mast cells, and MBP can stimulate the release of EPO from mast cells. Eosinophils can serve as a local source of specific lipid mediators as well as induce the release of mediators from mast cells and basophils. Eosinophil granule content is released following similar stimuli to neutrophil granules, e.g. during phagocytosis of opsonized particles and by chemotactic factors. Neutrophil lysosomal enzymes act primarily on material engulfed in phagolysosomes, while the eosinophil granule contents act mainly on extracellular target structure such as parasites and inflammatory mediators.

Monocyte and macrophage development takes place in the bone marrow and passes through the following steps: stem cell; committed stem cell; monoblast; promonocyte; monocyte in bone marrow; monocyte in peripheral blood; and macrophage in tissues. Monocyte differentiation in the bone marrow proceeds rapidly (1.5 to 3 days). During differentiation, granules are formed in monocyte cytoplasm and these can be divided as in neutrophils into at least two types. However, they are fewer and smaller than their neutrophil counterparts (azurophil and specific granules). Their enzyme content is similar.

Granule-bound enzymes of monocytes/macrophages include lysozyme, acid phosphatase, and beta-glucuronidase. As a model for in vivo studies, lysozyme secretion from U937 cells was used. This cell line is derived from a human histiocytic lymphoma and has been used as a monocytic cell line that can be activated by a variety of agonists, such as PMA (Hoff et al., J Leukoc Biol 1992; 52:173-182; Balboa et al., J Immunol 2003; 170:5276-5280; Sundstrom et al., Int J Cancer 1976; 17:565-577).

Natural killer (NK) cells and cytotoxic lymphocytes contain potent cytotoxic granules including perform, a pore-forming protein, and granzymes, lymphocyte-specific serine proteases. For example, the NK-92 cell line is an IL-2-dependent human line established from a patient with rapidly progressive non-Hodgkin's lymphoma (Gong J H., Maki G, Klingemann H G. Characterization of a human cell line (NK-92) with phenotypical and functional characteristics of activated natural killer cells. Leukemia 1994; 8:652-658). NK-92 cells express high levels of molecules involved in the perforin-granzyme cytolytic pathway that targets a wide range of malignant cells (Gong et al, vide infra, and Maki G, Klingemann H G, Martinson J A, Tam Y K. Factors regulating the cytotoxic activity of the human natural killer cell line, NK-92. J Hematother Stem Cell Res 2001; 10:369-383).

Granzymes are exogenous serine proteases that are released by cytoplasmic granules within cytotoxic T cells and natural killer cells. Granzymes can induce apoptosis within virus-infected cells, thus destroying them.

Extracellular release of a mediator of inflammation (inflammatory mediator) from a granulocyte (or leukocyte), and extracellular release of more than one mediator of inflammation (inflammatory mediator) from a granulocyte (or leukocyte) is sometimes referred to herein as degranulation. In a preferred embodiment, the release of a mediator of inflammation comprises release of said mediator from a granule located in the interior of a granulocyte or leukocyte. The release of inflammatory mediator is preferably the release of an inflammatory mediator from these granules.

Neutrophils and macrophages, upon priming by pro-inflammatory agents (inflammatory stimulants) such as TNFα, dramatically increase their synthesis of MARCKS protein: as much as 90% of the new protein formed by neutrophils in response to either TNFα or lipopolysaccharide (LPS) is MARCKS (Thelen M, Rosen A, Nairn A C, Aderem A. Tumor necrosis factor alpha modifies agonist-dependent responses in human neutrophils by inducing the synthesis and myristoylation of a specific protein kinase C substrate. Proc Natl Acad Sci USA 1990; 87:5603-5607). MARCKS can thus have an important role in subsequent release of inflammatory mediators when granule-containing cells, such as neutrophils and macrophages, are stimulated by agonists, especially those that work by activating PKC (Burgoyne et al., Physiol Rev 2003; 83:581-632; Logan et al. J Allergy Clin Immunol 2003; 111: 923-932; Smolen et al., Biochim Biophys Acta 1990; 1052:133-142; Niessen et al., Biochim. Biophys. Acta 1994; 1223:267-273; Naucler et al., J Leukoc Biol 2002; 71:701-710).

In one aspect of this invention, administration of a degranulation-inhibiting amount of MANS peptide or an active fragment thereof as described herein to a site of inflammation in a subject, which site of inflammation has resulted from the onset of entry of a disease, a condition, a trauma, a foreign body, or a combination thereof at the site of inflammation in the subject, can reduce the amount of a mediator of inflammation released from infiltrating leukocytes at the site of inflammation, where the leukocytes are preferably granulocytes. The administration of the MANS peptide and/or at least one active fragment thereof can reduce the amount of a mediator of inflammation released from leukocytes such as granulocytes infiltrating into the site of inflammation. The degranulation-inhibiting amount of MANS peptide, or the degranulation-inhibiting amount of an active fragment thereof, is sufficient to reduce or inhibit the exocytotic release of inflammatory mediators from granules contained within the inflammatory cells infiltrating into the site. Degranulation-inhibiting efficacy is measured at a time after administration of the MANS peptide or the fragment thereof by comparison of the percent of inhibition (i.e., percent of reduction) of the release of mediators of inflammation from said cells (leukocytes or granulocytes or other inflammatory cells) relative to the level or amount or concentration of said mediators of inflammation released or produced at approximately the same time in the absence of MANS peptide and/or in the absence of the active fragment thereof. Additionally, a skilled clinician can determine whether inflammation at the tissue site has been reduced by measuring symptoms and parameters of inflammation known as indicators of the disease to determine whether a sufficient or therapeutically effective amount MANS peptide and/or an active fragment thereof has been administered. A sufficient degranulation-inhibiting amount is the percentage of reduction of a mediator of inflammation released from a granulocyte, at the site of inflammation, which is from about 1% to about 99%, preferably from 5% to about 99%, more preferably from about 10% to about 99%, even more preferably from about 25% to 99%, and even more preferably from about 50% to about 99% of the amount of said mediator of inflammation released from said granulocyte in the absence of MANS peptide or an active fragment thereof tested under the same conditions.

In one aspect of this invention, administration of a degranulation-inhibiting amount of MANS peptide to a site of inflammatory stimulation in an animal, which site of inflammatory stimulation has been created by administration of an inflammation-stimulating amount of an inflammatory stimulant to said site, can reduce the amount of a mediator of inflammation released from a granulocyte, which granulocyte is stimulated by said inflammatory stimulant at said site of inflammatory stimulation, from about 1% to about 99%, preferably from 5% to about 99%, more preferably from about 10% to about 99%, even more preferably from about 25% to 99%, and even more preferably from about 50% to about 99% of the amount of said mediator of inflammation released from said granulocyte in the absence of MANS peptide in the presence of the identical inflammation-stimulating amount of said inflammatory stimulant.

In another aspect of this invention, administration of a degranulation-inhibiting amount of MANS peptide to a site of inflammatory stimulation in an animal, which site of inflammatory stimulation has been created by administration of an inflammation-stimulating amount of an inflammatory stimulant to said site, can reduce the amount of a mediator of inflammation released from a granulocyte, which granulocyte is stimulated by said inflammatory stimulant at said site of inflammatory stimulation, by 100% of the amount of said mediator of inflammation released from said granulocyte in the absence of MANS peptide in the presence of the identical inflammation-stimulating amount of said inflammatory stimulant.

An example of an inflammatory stimulant used in in vitro examples herein is phorbol 12-myristate 13-acetate (PMA). Monocyte chemoattractant protein (MCP-1) is nearly as effective as C5a, and much more potent than IL-8, in the degranulation of basophils, resulting in histamine release. Histamine release can occur after stimulation with chemokines (i.e., chemoattractant cytokines), RANTES and MIP-1.

In a preferred embodiment, relative to the basal concentration of MARCKS peptide present at the site of inflammatory stimulation, the degranulation-inhibiting amount of MANS peptide administered to a site of inflammatory stimulation in an animal comprises from about 1 time to about 1,000,000 times the concentration of the MARCKS peptide at said site of inflammatory stimulation, preferably from about 1 time to about 100,000 times the concentration of the MARCKS peptide at said site of inflammatory stimulation, more preferably from about 1 time to about 10,000 times the concentration of the MARCKS peptide at said site of inflammatory stimulation, even more preferably from about 1 time to about 1,000 times the concentration of the MARCKS peptide at said site of inflammatory stimulation, even more preferably from about 1 time to about 100 times the concentration of the MARCKS peptide at said site of inflammatory stimulation, and even more preferably from about 1 time to about 10 times the concentration of the MARCKS peptide at said site of inflammatory stimulation.

In a preferred embodiment, the granulocyte resides on or in the airway of an animal, preferably a human, and the MANS peptide is administered by inhalation, such as by inhalation of a pharmaceutical composition comprising the MANS peptide, for example a pharmaceutical composition comprising the MANS peptide and an aqueous solution, which composition is administered in the form of an aerosol, or a pharmaceutical composition comprising the MANS peptide in the form of a dry powder, which composition is administered using a dry powder inhaler. Other methods and devices known in the art for administration of a solution or powder by inhalation such as, for example, droplets, sprays, and nebulizers, can be useful.

In some embodiments, it is possible that the peptide of the present invention may block secretory processes that are physiologically important, including basal secretory functions. Although inventors do not wish to be bound to any particular theory of the invention, it is thought that the mechanisms regulating such basal secretion are different than those regulating stimulated secretion. Alternatively, basal secretory mechanisms may require less MARCKS protein than stimulated secretion. Basal secretion may be preserved since all therapies to block MARCKS-mediated secretion may not eliminate all MARCKS function.

As used herein, the term "MARCKS nucleotide sequence" refers to any nucleotide sequence derived from a gene encoding a MARCKS protein, including, for example, DNA or RNA sequence, DNA sequence of the gene, any transcribed RNA sequence, RNA sequence of the pre-mRNA or mRNA transcript, and DNA or RNA bound to protein.

Precise delivery of the MARCKS-blocking peptide may also overcome any potential limitations of blocking important secretory processes. Delivering such agents to the respiratory tract should be readily accomplished with inhaled formulations. Since these agents may be useful in treating inflammatory bowel disease, one can envision delivery of the blocking agents into the rectum/colon/intestinal tract via enema or suppositories. Injections or transdermal delivery into inflamed joints may yield relief to patients with arthritic or autoimmune diseases by limiting the secretion from localized inflammatory cells. Injection into areas surrounding nerve endings may inhibit secretion of some types of neurotransmitters, blocking transmission of severe pain or uncontrolled muscle spasms. Delivery of the peptide for the treatment of inflammatory skin diseases should be readily accomplished using various topical formulations known in the art.

It has been shown that the myristoylated alanine-rich C kinase substrate (MARCKS), a widely distributed PKC substrate may be a key regulatory molecule mediating mucin granule release by normal human bronchial epithelial (NHBE) cells. Secretion of mucin from these cells may be maximized by activation of both PKC and PKG. It is believed that MARCKS serves as the point of convergence for coordinating the actions of these two protein kinases to control mucin granule release. The mechanism appears to involve PKC-dependent phosphorylation of MARCKS, which releases MARCKS from the plasma membrane into the cytoplasm, where it is in turn dephosphorylated by a protein phosphatase 2A (PP2A) that is activated by PKG. This dephosphorylation may allow MARCKS to regain its membrane-binding capability, enabling its attachment to membranes of cytoplasmic mucin granules. In addition, MARCKS interacts with actin and myosin in the cytoplasm and thus may be able to tether the granules to the cellular contractile apparatus, thus, mediating subsequent granule movement and exocytosis. Secretion of the inflammatory mediatory MPO from neutrophils may also be maximized by activation of both PKC and PKG (as illustrated in FIGS. 11-15). It is possible that MARCKS serves as the point of convergence for coordinating actions of these two protein kinases that control secretion from membrane-bound compartments in inflammatory cells (i.e. secretion of MPO from neutrophils).

The present invention demonstrates secretion of the inflammatory mediator MPO from canine or human neutrophils was enhanced by concurrent activation of both PKC and PKG, while activation of either kinase alone was insufficient to induce a maximal secretory response. An enhanced secretory response to PMA alone was documented in NHBE cells (FIG. 1, column 4) and in neutrophils (FIG. 11), although the magnitude of the response was much less than that observed by others in a rat goblet-like cell line. See, Abdullah et al, supra. In addition, although it was reported previously that a cGMP analogue could induce significant mucin secretion from cultured guinea pig tracheal epithelial cells (Fischer et al., supra), it should be noted that this response did not reach significant levels until 8 h of exposure. A secretory response with such a long lag period is unlikely to be a direct effect and probably involves de novo protein synthesis as opposed to release of preformed and stored cytoplasmic granules. Nevertheless, the apparent synergistic effect involving cooperative activation of both PKC and PKG may suggest a complex and stringent signaling mechanism mediating mucin secretion and/or inflammatory mediators. Applicants note that the pathway disclosed below was used to study inflammatory mediator release from neutrophils and is likely the same pathway as that used to study goblet cell secretions.

As stated above, the present invention may be used in a pharmaceutical formulation. In certain embodiments, the drug product is present in a solid pharmaceutical composition that may be suitable for oral administration. A solid composition of matter according to the present invention may be formed and may be mixed with and/or diluted by an excipient. The solid composition of matter also may be enclosed within a carrier, which may be, for example, in the form of a capsule, sachet, tablet, paper, or other container. When the excipient serves as a diluent, it may be a solid, semi-solid, or liquid material that acts as a vehicle, carrier, or medium for the composition of matter.

Various suitable excipients will be understood by those skilled in the art and may be found in the *National Formulary*, 19: 2404-2406 (2000), the disclosure of pages 2404 to 2406 being incorporated herein in their entirety. Examples of suitable excipients include, but are not limited to, starches, gum arabic, calcium silicate, microcrystalline cellulose, methacrylates, shellac, polyvinylpyrrolidone, cellulose, water, syrup, and methylcellulose. The drug product formulations additionally can include lubricating agents such as, for example, talc, magnesium stearate and mineral oil; wetting agents; emulsifying and suspending agents; preserving agents such as methyl- and propyl hydroxybenzoates; sweetening agents; or flavoring agents. Polyols, buffers, and inert fillers also may be used. Examples of polyols include, but are not limited to, mannitol, sorbitol, xylitol, sucrose, maltose, glucose, lactose, dextrose, and the like. Suitable buffers include, but are not limited to, phosphate, citrate, tartrate, succinate, and the like. Other inert fillers that may be used include those that are known in the art and are useful in the manufacture of various dosage forms. If desired, the solid formulations may include other components such as bulking agents and/or granulating agents, and the like. The drug products of the invention may be formulated so as to provide quick, sustained, or delayed release of the active ingredient after administration to the patient by employing procedures well known in the art.

To form tablets for oral administration, the composition of matter of the present invention may be made by a direct compression process. In this process, the active drug ingredients may be mixed with a solid, pulverant carrier such as, for example, lactose, saccharose, sorbitol, mannitol, starch, amylopectin, cellulose derivatives or gelatin, and mixtures thereof, as well as with an antifriction agent such as, for example, magnesium stearate, calcium stearate, and polyethylene glycol waxes. The mixture may then be pressed into tablets using a machine with the appropriate punches and dies to obtain the desired tablet size. The operating parameters of the machine may be selected by the skilled artisan. Alternatively, tablets for oral administration may be formed by a wet granulation process. Active drug ingredients may be mixed with excipients and/or diluents. The solid substances may be ground or sieved to a desired particle size. A binding agent may be added to the drug. The binding agent may be suspended and homogenized in a suitable solvent. The active ingredient and auxiliary agents also may be mixed with the binding agent solution. The resulting dry mixture is moistened with the solution uniformly. The moistening typically causes the particles to aggregate slightly, and the resulting mass is pressed through a stainless steel sieve having a desired size. The mixture is then dried in controlled drying units for the determined length of time necessary to achieve a desired particle size and consistency. The granules of the dried mixture are sieved to remove any powder. To this mixture, disintegrating, antifriction, and/or anti-adhesive agents may be added. Finally, the mixture is pressed into tablets using a machine with the appropriate punches and dies to obtain the desired tablet size. The operating parameters of the machine may be selected by the skilled artisan.

If coated tablets are desired, the above prepared core may be coated with a concentrated solution of sugar or cellulosic polymers, which may contain gum arabic, gelatin, talc, titanium dioxide, or with a lacquer dissolved in a volatile organic solvent or a mixture of solvents. To this coating various dyes may be added in order to distinguish among tablets with different active compounds or with different amounts of the active compound present. In a particular embodiment, the active ingredient may be present in a core surrounded by one or more layers including enteric coating layers.

Soft gelatin capsules may be prepared in which capsules contain a mixture of the active ingredient and vegetable oil. Hard gelatin capsules may contain granules of the active ingredient in combination with a solid, pulverulent carrier, such as, for example, lactose, saccharose, sorbitol, mannitol, potato starch, corn starch, amylopectin, cellulose derivatives, and/or gelatin.

Liquid preparations for oral administration may be prepared in the form of syrups or suspensions, e.g., solutions containing an active ingredient, sugar, and a mixture of ethanol, water, glycerol, and propylene glycol. If desired, such liquid preparations may comprise one or more of following: coloring agents, flavoring agents, and saccharin. Thickening agents such as carboxymethylcellulose also may be used.

In the event that the above pharmaceuticals are to be used for parenteral administration, such a formulation may comprise sterile aqueous injection solutions, non-aqueous injection solutions, or both, comprising the composition of matter of the present invention. When aqueous injection solutions are prepared, the composition of matter may be present as a water soluble pharmaceutically acceptable salt. Parenteral preparations may contain anti-oxidants, buffers, bacteriostats, and solutes which render the formulation isotonic with the blood of the intended recipient. Aqueous and non-aqueous sterile suspensions may comprise suspending agents and thickening agents. The formulations may be presented in unit-dose or multi-dose containers, for example sealed ampules and vials. Extemporaneous injection solutions and suspensions may be prepared from sterile powders, granules and tablets of the kind previously described.

The composition of matter also may be formulated such that it may be suitable for topical administration (e.g., skin cream). These formulations may contain various excipients known to those skilled in the art. Suitable excipients may include, but are not limited to, cetyl esters wax, cetyl alcohol, white wax, glyceryl monostearate, propylene glycol, monostearate, methyl stearate, benzyl alcohol, sodium lauryl sulfate, glycerin, mineral oil, water, carbomer, ethyl alcohol, acrylate adhesives, polyisobutylene adhesives, and silicone adhesives.

Having now described the invention, the same will be illustrated with reference to certain examples, which are included herein for illustration purposes only, and which are not intended to be limiting of the invention.

EXAMPLES

Figure 1B:
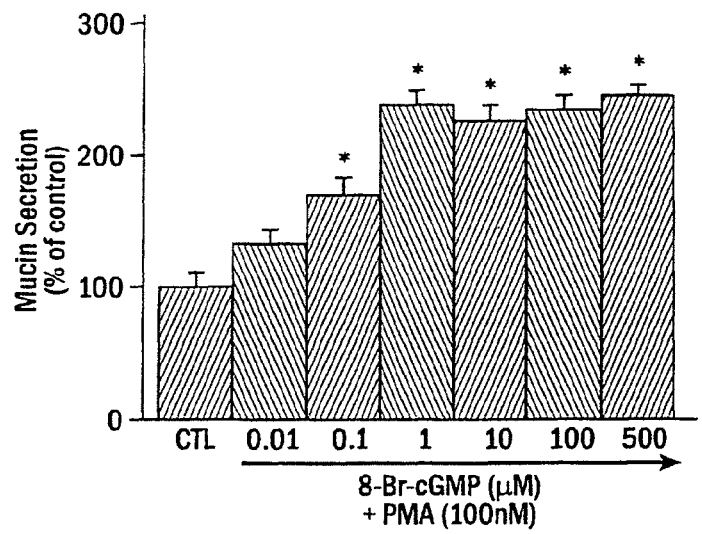
Figure 1C:
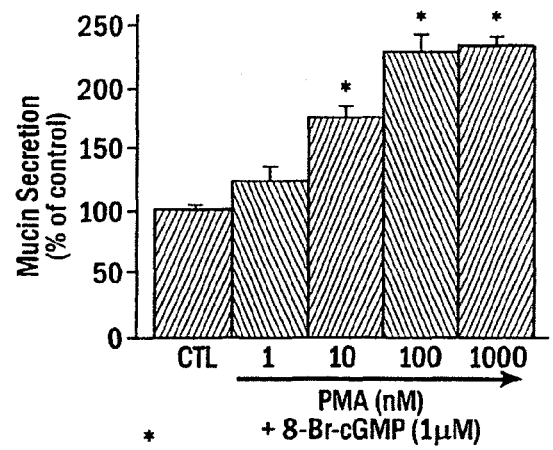
Figure 1D:
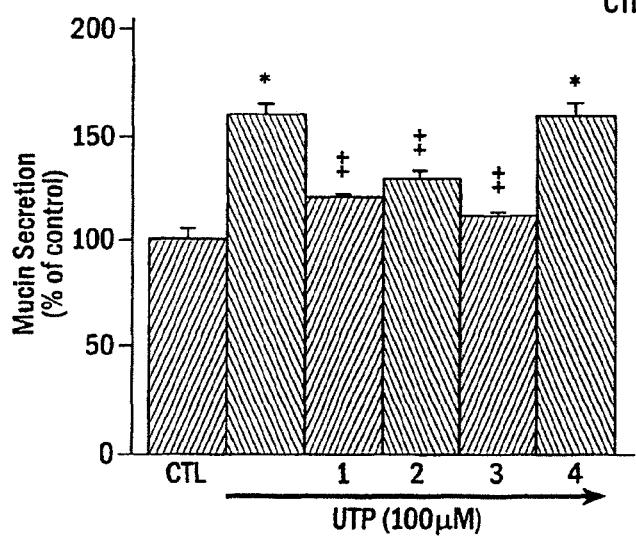

Mucin Hypersecretion from NHBE Cells Involves Activation of Both PKC and PKG To determine the potential role of PKC and/or PKG in the mucin secretory process, NHBE cells were exposed to the following two specific protein kinase activators: the phorbol ester, phorbol 12-myristate 13-acetate (PMA), for activation of PKC, and the nonhydrolyzable cGMP analogue, 8-Br-cGMP, for activation of PKG. Preliminary studies examining mucin secretion in response to PMA stimulation at various concentrations for different times (up to 1 µM for 2 h) indicated that activation of PKC alone did not induce significant mucin secretion from NHBE cells, although a moderate secretory response was repeatedly observed at PMA concentrations higher than 100 nM ($0.05<p<0.1$). Also, the cells did not respond to the cGMP analogues at concentrations as high as 500 µM for up to 2 h of exposure. However, a combination of PMA+8-Br-cGMP, affecting dual activation of PKC and PKG, provoked a rapid increase in secretion, approximately doubling it within 15 min of exposure (FIG. 1A). This secretory response induced by PMA+8-Br-cGMP was concentration-dependent, with maximal stimulation at 100 nM PMA+1 µM 8-Br-cGMP (FIGS. 1B and 1C). In FIGS. 1A, 1B and 1C, NHBE cells were exposed to indicated reagent(s) or medium alone (CTL) for 15 min. In FIG. 1D, NHBE cells were pre-incubated with the indicated inhibitor for 15 min and then stimulated with 100 .mu.M UTP for 2 h. Secreted mucin in response to the treatment was collected and assayed by ELISA. Data are presented as mean.+−.S.E. (n=6 at each point). The * stands for significantly different from medium control ($p<0.05$); # stands for different from medium control ($0.05<p<0.1$); and ‡ stands for significantly different from UTP stimulation CD<0.05).

UTP is a well defined pathophysiologically relevant mucin secretagogue. Lethem et al., *Am. J. Respir. Cell Mol. Biol.* 9, 315-322 (1993). The present invention further demonstrates that UTP, at various concentrations, preferably 40 to 140 µM, may induce a significant increase in mucin secretion from NHBE cells after a 2-h exposure. To determine whether PKC and PKG were involved in regulation of mucin secretion in response to a pathophysiological stimulus, effects of PKC/PKG inhibitors on UTP-induced mucin secretion were investigated. NHBE cells were preincubated with various inhibitors for 15 min and then exposed to UTP (100 µM) plus the inhibitor for 2 h. The secreted mucin was measured by ELISA. The results indicated that mucin secretion provoked by UTP may require both PKC and PKG activities, as the secretory response was attenuated independently by the PKC inhibitor calphostin C (500 nM), the PKG inhibitor $R_p$-8-Br-PET-cGMP (10 µM), or the soluble guanylyl cyclase (GC-S) inhibitor LY83583 (50 µM) but likely not by the protein kinase A (PKA) inhibitor KT5720 (500 nM) (FIG. 1D). Apparently, mucin secretion in NHBE cells may be regulated by a signaling mechanism involving both PKC and PKG.

To address involvement of PKG in the secretory process, 8-Br-cGMP was utilized in these studies. Although the primary physiological effect of 8-Br-cGMP is to activate PKG, it also has been reported to act as an agonist for cGMP-gated ion channels in some cells and, at high concentrations, to cross-activate PKA. To preclude the possibility that cGMP-gated ion channels and/or PKA may play a role in mucin secretion by NHBE cells, $R_p$-8-Br-cGMP, a unique cGMP analogue that can activate cGMP-gated ion channels similar to 8-Br-cGMP but inhibit PKG activity, was used as an agonist to distinguish the effects of PKG and cGMP-gated ion channels on mucin release. As illustrated in the figures, particularly, FIG. 1A (column 11), $R_p$-8-Br-cGMP did not enhance mucin secretion when added to the cells with PMA. Likewise, the specific PKA inhibitor, KT5720 (500 nM), did not affect mucin secretion induced by either PMA+8-Br-cGMP or UTP (FIG. 1D, column 4). These studies may negate the possibility that cGMP-gated ion channels or PKA are associated with mucin secretion, indicating that activation of PKG in NHBE cells is the mechanism whereby 8-Br-cGMP contributes to enhanced secretion. Furthermore, because UTP-induced mucin hypersecretion can be attenuated by the soluble guanylyl cyclase (GC-S) inhibitor LY83583, it is likely that activation of PKG occurs via the signaling pathway of nitric oxide (NO)→GC-S→cGMP→PKG, as illustrated previously in differentiated guinea pig tracheal epithelial cells in vitro.

Given the participation of both PKC and PKG in the mucin secretory process, the present invention examines potential intracellular substrates of these enzymes that could play a role in signaling events downstream of the kinase activation. Numerous intracellular substrates can be phosphorylated by PKC or PKG, and phosphorylation by PKC of one such substrate, MARCKS protein, seemed to be of particular interest. MARCKS phosphorylation has been observed to correlate with a number of cellular processes involving PKC signaling and cytoskeletal contraction, such as cell movement, mitogenesis, and neural transmitter release. Because the dynamic process of secretion requires both kinase activation and translocation of intracellular granules to the cell periphery, MARCKS appeared to be a candidate for a mediator molecule connecting PKC/PKG activation and mucin granule exocytosis.

Figure 2A:
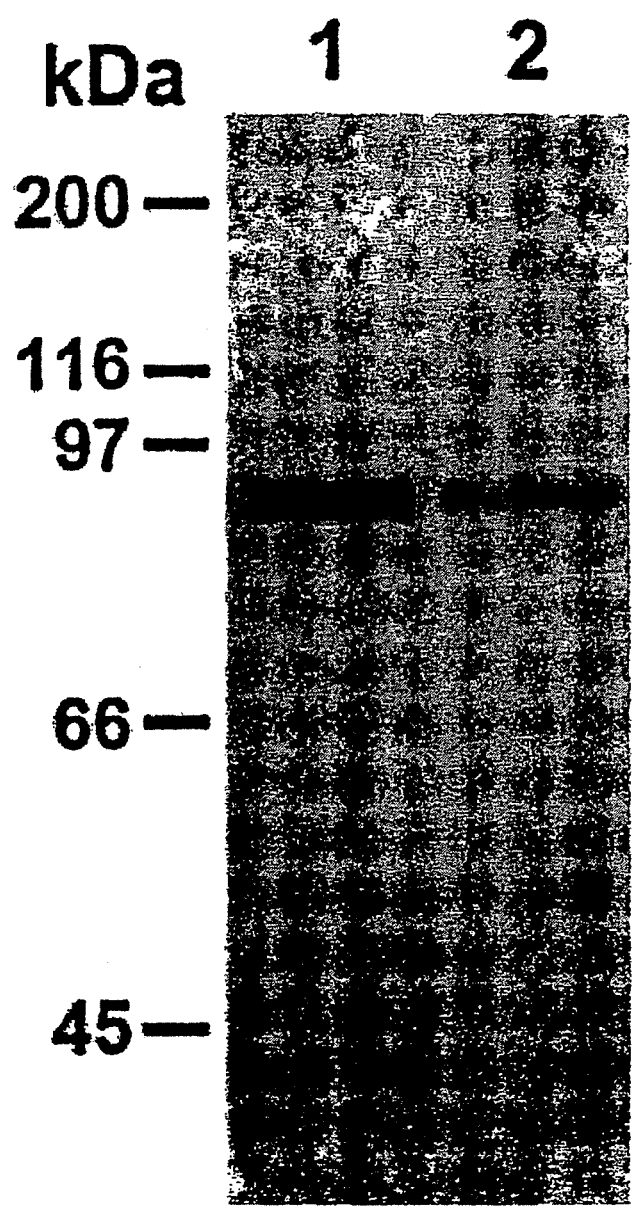
FIGS. 2A-2B demonstrate that the MARCKS protein is a key component of the mucin secretory pathway.

MARCKS is a Key Molecule Linking PKC/PKG Activation to Mucin Secretion in NHBE Cells To address the signaling mechanism downstream of protein kinase activation, MARCKS protein, a specific cellular substrate of PKC that might play a role in linking kinase activation to granule release was studied. First, the presence of MARCKS in NHBE cells by [³H] myristic acid-labeled immunoprecipitation assay was confirmed. As illustrated in FIG. 2A, MARCKS was expressed in NHBE cells, and the majority of this protein was membrane-associated under unstimulated conditions. In FIG. 2A, cells were labeled with [³H]myristic acid overnight and the membrane (lane 1) and the cytosol (lane 2) fractions were then isolated by differential centrifugation. A role for MARCKS as a key regulatory component of the mucin secretory pathway may be demonstrated in three different ways.

Figure 8:
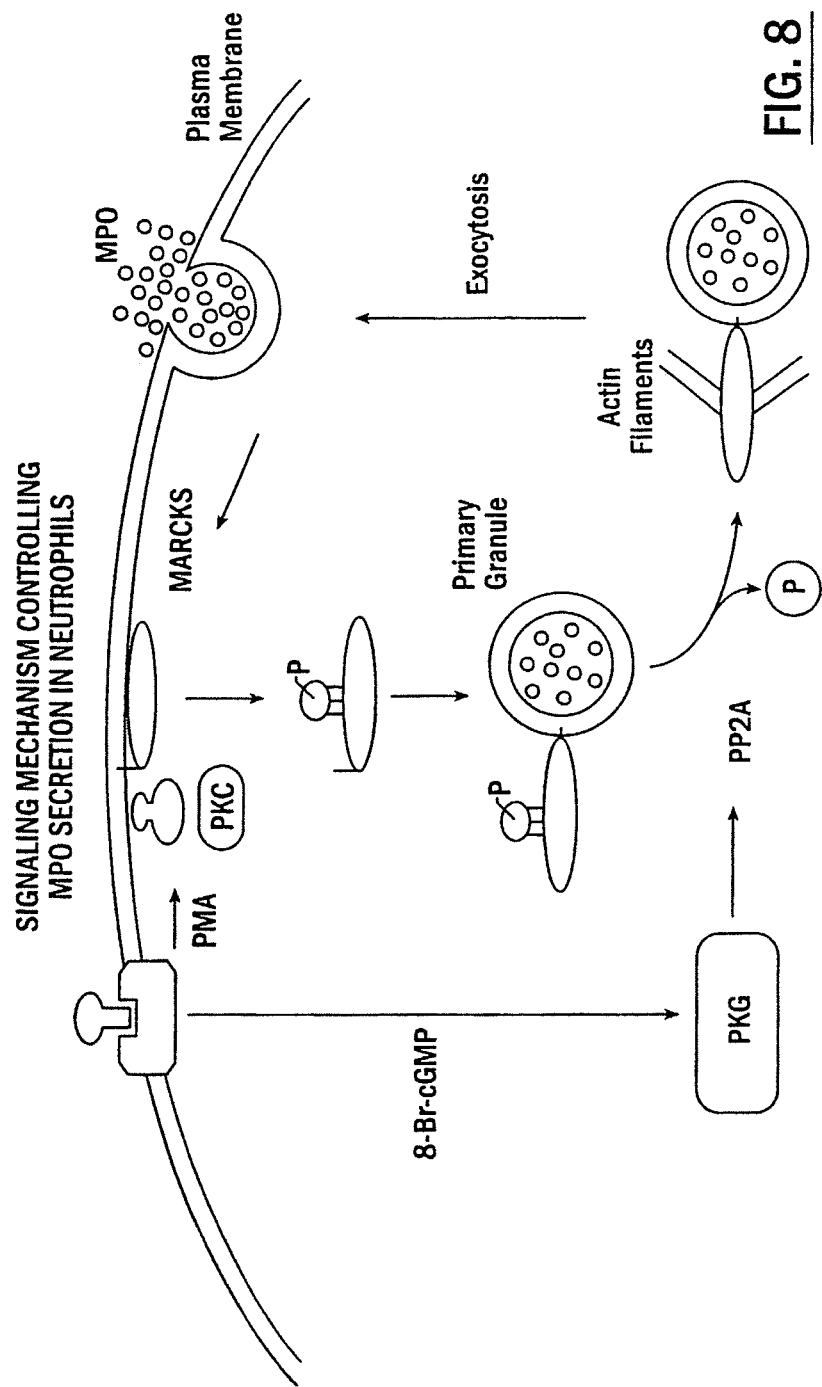
FIG. 8 depicts a signaling mechanism controlling mucin secretion by human airway epithelial cells.

As stated above, direct involvement of MARCKS in mucin secretion by NHBE cells may be demonstrated by three separate lines of evidence. First, mucin secretion in response to stimulation by PMA+8-Br-cGMP or UTP was inhibited in a concentration-dependent manner by the MANS peptide, which had the amino acid sequence identical to the N-terminal region of MARCKS, whereas the corresponding control peptide (RNS), containing the same amino acid composition but arranged in random order, did not affect secretion. The N-terminal myristoylated domain of MARCKS is known to mediate the MARCKS-membrane association. As indicated in FIG. 8, MARCKS may function as a molecular linker by interacting with granule membranes at its N-terminal domain and binding to actin filaments at its PSD site, thereby tethering granules to the contractile cytoskeleton for movement and exocytosis. FIG. 8 shows a possible mechanism depicting that mucin secretagogue interacts with airway epithelial (goblet) cells and activates two separate protein kinases, PKC and PKG. Activated PKC phosphorylates MARCKS, causing MARCKS translocation from the plasma membrane to the cytoplasm, whereas PKG, activated via the nitric oxide (NO)→GC-S→cGMP→PKG pathway, in turn activates a cytoplasmic PP2A, which dephosphorylates MARCKS. This dephosphorylation stabilizes MARCKS attachment to the granule membranes. In addition, MARCKS also interacts with actin and myosin, thereby linking granules to the cellular contractile machinery for subsequent movement and exocytotic release. The attachment of MARCKS to the granules after it is released into the cytoplasm may also be guided by specific targeting proteins or some other forms of protein-protein interactions in which the N-terminal domain of MARCKS is involved. In either case, the MANS peptide, or an active fragment thereof, comprising at least 6 amino acids, would act to inhibit competitively targeting of MARCKS to the membranes of mucin granules, thereby blocking secretion.

Figure 3A:
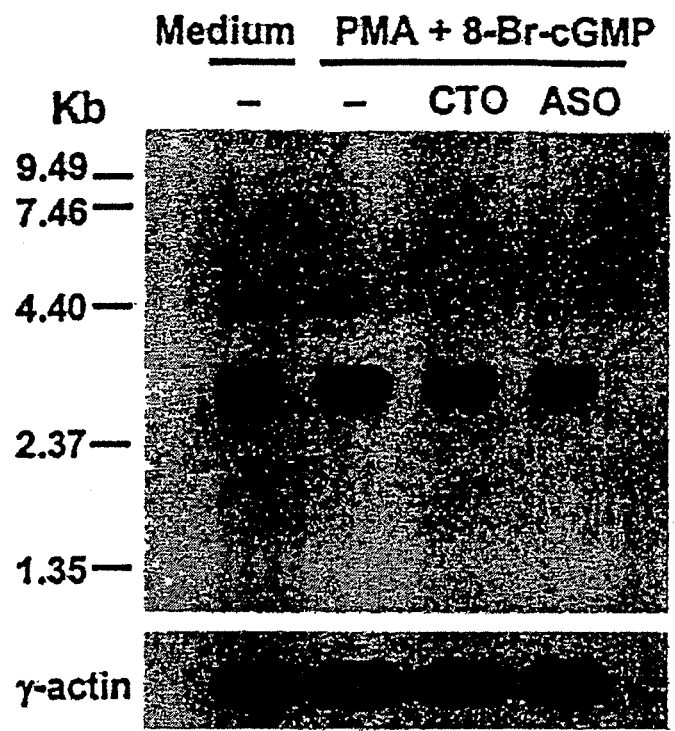
FIGS. 3A-3C depicts a gel illustrating that an antisense oligonucleotide directed against MARCKS down-regulates MARCKS expression and attenuates mucin hypersecretion.
Figure 3A:
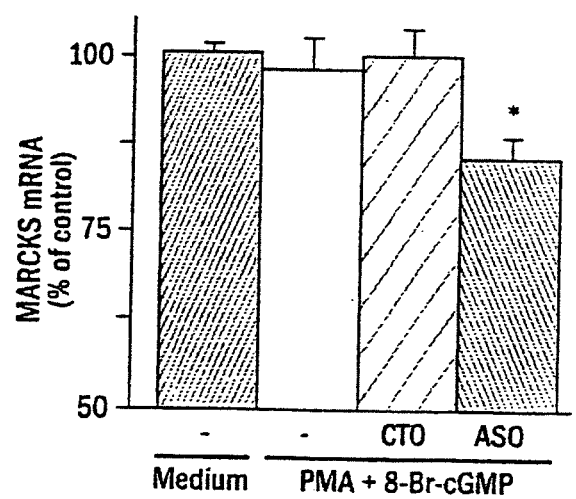
Figure 3B:
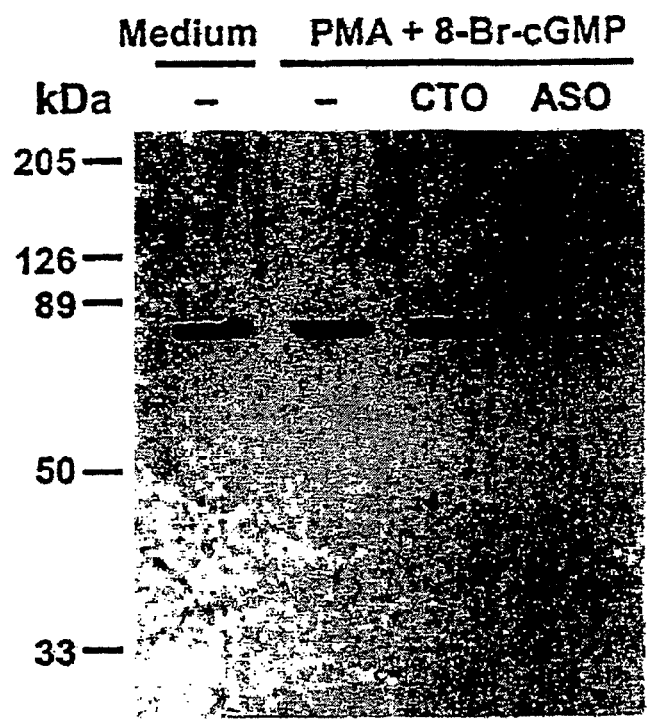
Figure 3B:
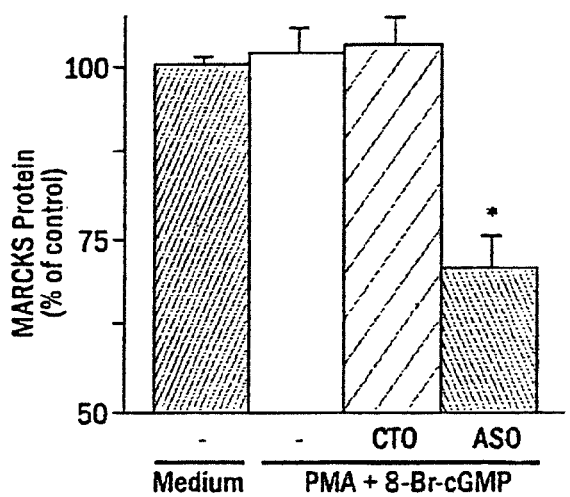
Figure 3C:
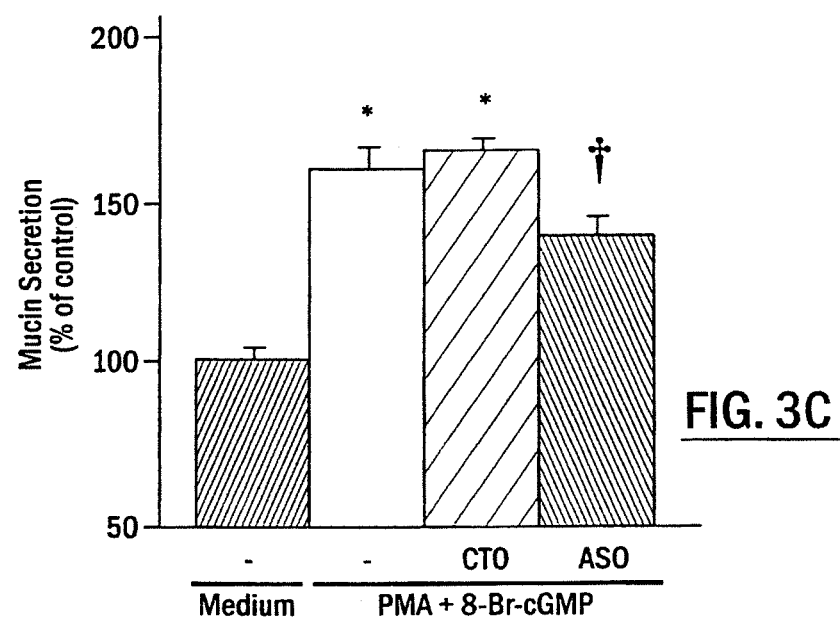

A second test demonstrated the inhibitory effect of a MARCKS-specific antisense oligonucleotide on mucin secretion. As shown in FIGS. 3A-3C, the antisense oligonucleotide down-regulated MARCKS mRNA and protein levels in NHBE cells and substantially attenuated mucin secretion induced by PKC/PKG activation. The inhibition was not as dramatic as that seen with the MANS peptide, which might be due to the high levels of endogenous MARCKS protein in NHBE cells and the relatively long half-life of MARCKS mRNA ($t_{1/2}$=4-6 h). In FIGS. 3A-3C, NHBE cells were treated with the antisense or the control oligonucleotide for 3 days and then stimulated with PMA (100 nM)+8-Br-cGMP (1 µM) for 15 min. Mucin secretion was analyzed by ELISA. Total RNA and protein were isolated from treated cells. MARCKS mRNA was assessed by Northern hybridization, and protein was assessed by Western blot. In the PMA (100 nM)+8-Br-cGMP (1 µM) FIG. 3A is a Northern blot that showed a decrease of .about.15% in MARCKS mRNA compared with controls in the attached chart; FIG. 3B is Western blot that showed a decrease of about 30% in MARCKS protein in the attached graph; and FIG. 3C shows mucin hypersecretion was attenuated significantly by the antisense oligonucleotide, whereas the control oligonucleotide had no effect. Data are presented as mean±S.E. (n=6 at each point) wherein the * is significantly different from medium control (p<0.05); and the † is significantly different from PMA+8-Br-cGMP stimulation (p<0.05). Additionally, it is noted that the term CTO is the control oligonucleotide, while the term ASO is an antisense oligonucleotide.

It has been demonstrated that antisense oligonucleotides that are complementary to specific RNAs can inhibit the expression of cellular genes as proteins. See Erickson and Izant, *Gene Regulation Biology Of Antisense RNA And DNA*, Vol. 1, Raven Press, N.Y., 1992. For example, selective inhibition of a p21 gene that differed from a normal gene by a single nucleotide has been reported. Chang et al., *Biochemistry* (1991), 30:8283-8286. Many hypotheses have been proposed to explain the mechanisms by which antisense oligonucleotides inhibit gene expression, however, the specific mechanism involved may depend on the cell type studied, the RNA targeted, the specific site on the RNA targeted, and the chemical nature of the oligonucleotide. Chiang et al., *J. Biol. Chem.* 1991, 266:18162-18171; Stein and Cohen, *Cancer Res.* 1988, 48:2659-2668.

A third experiment indicated that transfection of HBE1 cells with a PSD-deleted mutant MARCKS resulted in significant repression of mucin secretion induced by PKC/PKG activation. Deletion of the PSD would abolish the ability of MARCKS to bind to actin. As indicated in FIG. 8, by competing with native MARCKS for binding to granule membrane, the PSD-truncated MARCKS could thereby inhibit granule release as it is unable to interact with the actin filaments. Transfection of these cells with the wild-type MARCKS cDNA did not further enhance mucin secretion. Western blot assay showed that the expression level of endogenous MARCKS in HBE1 cells was quite high, comparable with that in NHBE cells, and transfection of wild-type MARCKS cDNA did not lead to notable increases in overall MARCKS protein level in these cells. This may explain why transfection with wild-type MARCKS did not further augment secretion and also why transfection with the PSD-deleted MARCKS only partially hindered mucin secretion.

Peptide Blocking Studies—

Figure 2B:
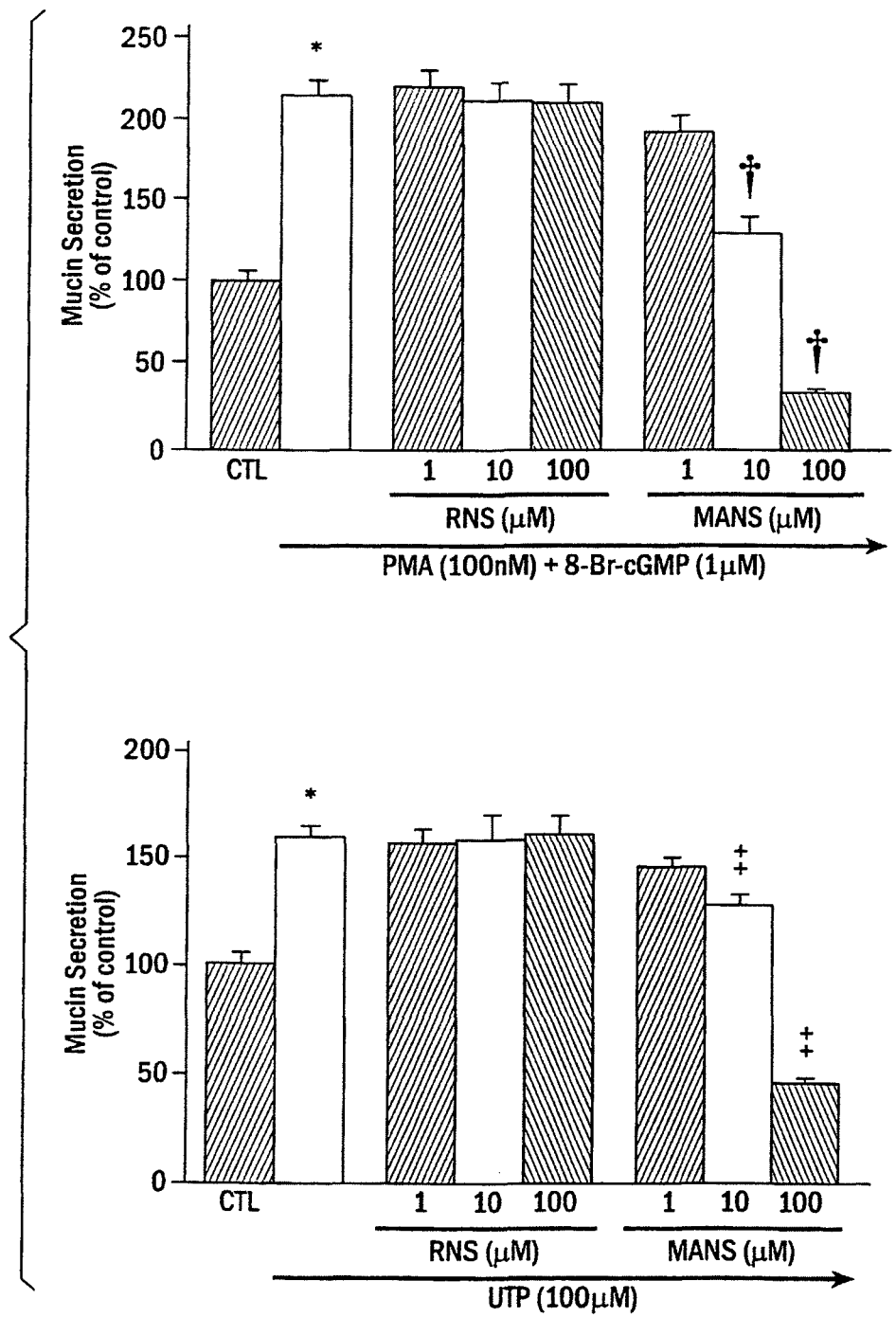

NHBE cells were preincubated with either the MANS or the RNS peptide (1-100 .mu.M) for 15 min, and then PMA (100 nM)+8-Br-cGMP (1 μM) or UTP (100 μM) was added, and cells were incubated for an additional 15 min or 2 h, respectively. Mucin secretion was measured by ELISA. As shown in FIG. 2B, incubation of NHBE cells with the MANS peptide resulted in a concentration-dependent suppression of mucin secretion in response to PKC/PKG activation or UTP stimulation, whereas the control peptide (RNS) may not have affected secretion at these same concentrations. In FIG. 2B, the MANS peptide blocks mucin hypersecretion induced by PMA+8-Br-cGMP or UTP in a concentration-dependent manner. NHBE cells were preincubated with the indicated peptide for 15 min and then exposed to PMA (100 nM)+8-Br-cGMP (1 .mu.M) for 15 min or UTP (100 μM) for 2 h. Mucin secretion was measured by ELISA. Data are presented as mean.+−.S.E. (n=6 at each point), wherein * is significantly different from medium control p<0.05); † is significantly different from PMA+8-Br-cGMP stimulation (p<0.05); and ‡ is significantly different from UTP stimulation (<0.05). Effects of the MANS peptide were likely not related to cytotoxicity or general repression of cellular metabolic activity, as neither the MANS nor the RNS peptide affected lactate dehydrogenase release or [$^3$H]deoxyglucose uptake by the cells.

Antisense Oligonucleotide Studies—

To demonstrate further MARCKS as a key signaling component of the mucin secretory pathway, the effect of an antisense oligonucleotide directed against MARCKS on mucin secretion was examined. As illustrated in FIG. 3, this antisense oligonucleotide down-regulated both mRNA and protein levels of MARCKS in NHBE cells and significantly attenuated mucin secretion induced by PMA+8-Br-cGMP, whereas a control oligonucleotide had no effect.

Figure 5A:
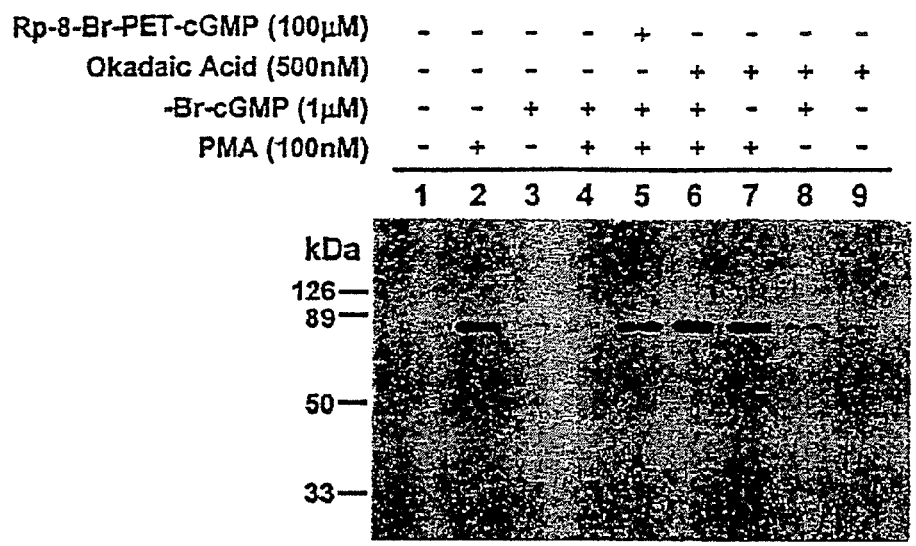
FIGS. 5A-5C show that PKG induces dephosphorylation of MARCKS by activating PP2A.
Figure 5B:
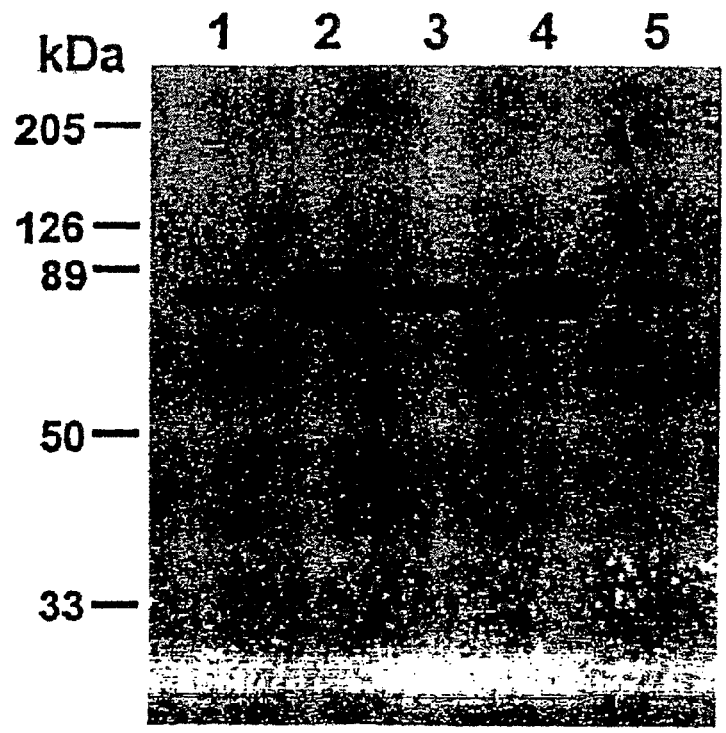
Figure 5C:
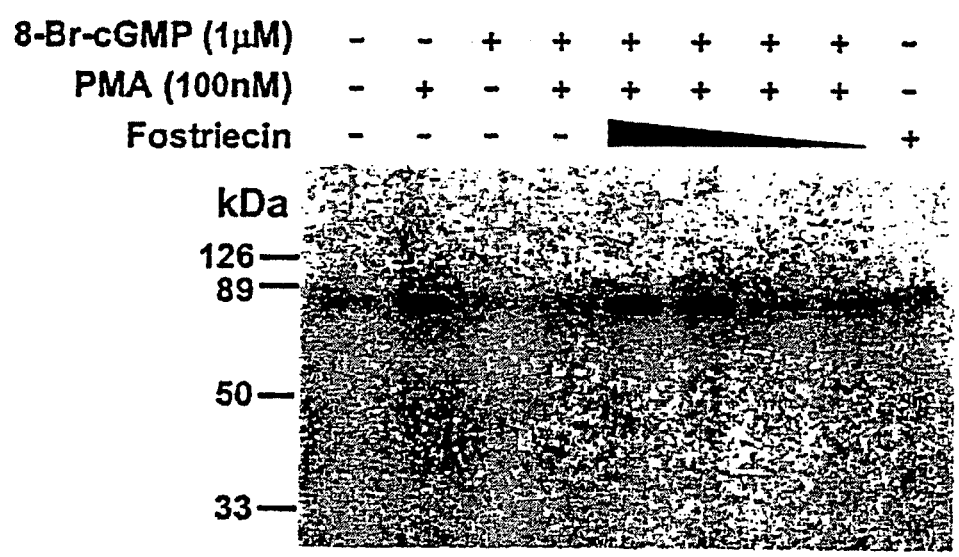

MARCKS Serves as a Convergent Signaling Molecule Mediating Cross-Talk of PKC and PKG Pathways Collectively, the above results demonstrated that MARCKS was involved integrally in the mucin secretory process. Next the present inventors addressed how MARCKS acts as a key regulatory molecule upon which PKC and PKG converge to regulate mucin secretion. As illustrated in FIG. 5, MARCKS was phosphorylated by PKC and consequently translocated from the membrane to the cytoplasm. Here, PKG appeared to induce dephosphorylation of MARCKS (FIG. 5A, lane 4, and FIG. 5B). This dephosphorylation was reversed by the PKG inhibitor $R_p$-8-Br-PET-cGMP (FIG. 5A, lane 5), indicating the dephosphorylation was specifically PKG-dependent. In FIG. 5, the NHBE cells were labeled with [$^{32}$P]orthophosphate and then exposed to the indicated reagents. MARCKS phosphorylation in response to the treatments was evaluated by immunoprecipitation assay. In FIG. 5A, 8-Br-cGMP reversed MARCKS phosphorylation induced by PMA, and this effect of 8-Br-cGMP could be blocked by $R_p$-8-Br-PET-cGMP (PKG inhibitor) or okadaic acid (PP1/2A inhibitor). For FIG. 5B, PMA-induced phosphorylation of MARCKS was reversed by subsequent exposure of cells to 8-Br-cGMP. Lane 1, medium alone for 8 min; lane 2, 100 nM PMA for 3 min; lane 3, 100 nM PMA for 3 min and then with 1 μM 8-Br-cGMP for 5 min; lane 4, 100 nM PMA for 8 min; lane 5, medium alone for 3 min and then 100 nM PMA+1 μM 8-Br-cGMP for 5 min. In FIG. 5C, 8-Br-cGMP-induced MARCKS dephosphorylation was attenuated by fostriecin in a concentration-dependent manner.

Figure 6:
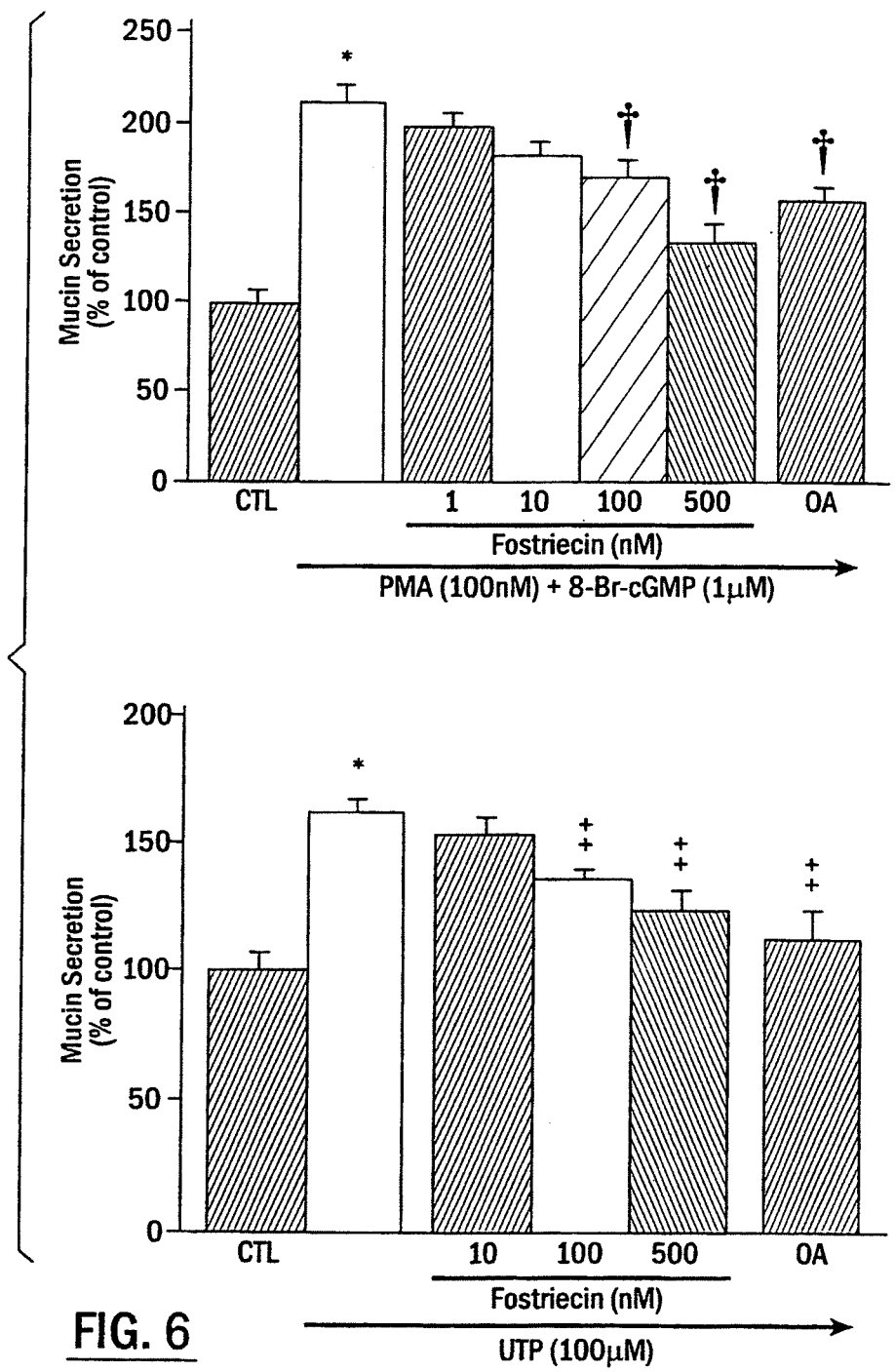
FIG. 6 depicts bar graphs that demonstrate that PP2A is an essential component of the mucin secretory pathway.

It is believed that PKG acts to dephosphorylate MARCKS via activation of a protein phosphatase. As illustrated in FIG. 5A (lane 6), okadaic acid at 500 nM, a concentration that could inhibit both PP1 and PP2A, blocked PKG-induced dephosphorylation of MARCKS, suggesting that PKG caused dephosphorylation by activating PP1 and/or PP2A. Further studies with fostriecin and direct assay of phosphatase activities indicated that only PP2A was activated by PKG and was responsible for removal of the phosphate groups from MARCKS (FIG. 5C). It is likely that either okadaic acid or fostriecin, at concentrations that inhibited PKG-induced dephosphorylation of MARCKS, attenuated mucin secretion induced by PMA+8-Br-cGMP or UTP as exhibited in FIG. 6. FIG. 6 helps to demonstrate that PP2A is an essential component of the mucin secretory pathway. NHBE cells were preincubated with the indicated concentration of fostriecin, okadaic acid (500 nM), or medium alone for 15 min and then stimulated with PMA (100 nM)+8-Br-cGMP (1 μM) for 15 min or with UTP (100 μM) for 2 h. Secreted mucin was measured by ELISA. Data are presented as mean.+−.S.E. (n=6 at each point) wherein * stands for significantly different from medium control (p<0.05); † stands for significantly different from PMA+8-Br-cGMP stimulation (p<0.05); and ‡ stands for significantly different from UTP stimulation p<0.05). Thus, dephosphorylation of MARCKS by a PKG-activated PP2A appears to be an essential component of the signaling pathway leading to mucin granule exocytosis.

To reveal molecular events by which MARCKS links kinase activation to mucin secretion, phosphorylation of MARCKS in response to PKC/PKG activation was investigated in depth. As illustrated in FIG. 4A, PMA (100 nM) likely induced a significant increase (3-4-fold) in MARCKS phosphorylation in NHBE cells, and this phosphorylation was attenuated by the PKC inhibitor calphostin C (500 nM). Once phosphorylated, MARCKS was translocated from the plasma membrane to the cytoplasm (FIG. 4B). More specifically, FIG. 4A shows the activation of PKC results in MARCKS phosphorylation in NHBE cells. Cells were labeled with [$^{32}$P]orthophosphate for 2 h and then exposed to the stimulatory and/or inhibitory reagents. MARCKS phosphorylation in response to the treatments was evaluated by immunoprecipitation as described. Lane 1, medium control; lane 2 the vehicle, 0.1% Me.sub.2SO; lane 3, 100 nM 4α-PMA; lane 4, 100 nM PMA; lane 5, 100 nM PMA+500 nM calphostin C; lane 6, 500 nM calphostin C. FIG. 4B demonstrates phosphorylated MARCKS is translocated from the plasma membrane to the cytoplasm. $^{32}$P-Labeled cells were exposed to PMA (100 nM) or medium alone for 5 min, and then the membrane and the cytosol fractions were isolated. Activation of PKG by 8-Br-cGMP (1 μM, another kinase activation event necessary for provoking mucin secretion, did not lead to MARCKS phosphorylation, but, in fact, the opposite effect was observed: MARCKS phosphorylation induced by PMA was reversed by 8-Br-cGMP (FIG. 5A). This effect of 8-Br-cGMP was not due to suppression of PKC activity, as the PMA-induced phosphorylation could be reversed by subsequent addition of 8-Br-cGMP to the cells (FIG. 5B). Therefore, PKG activation likely results in dephosphorylation of MARCKS.

Further investigation demonstrated that PKG-induced MARCKS dephosphorylation was blocked by 500 nM okadaic acid, a protein phosphatase (type 1 and/or 2A (PP1/2A)) inhibitor (FIG. 5A, lane 6). Thus, it appeared that the dephosphorylation was mediated by PP1 and/or PP2A. To define the subtype of protein phosphatase involved, a novel and more specific inhibitor of PP2A, fostriecin ($IC_{50}$=3.2 nM), was utilized in additional phosphorylation studies. As illustrated in FIG. 5C, fostriecin inhibited PKG-induced MARCKS dephosphorylation in a concentration-dependent manner (1-500 nM), suggesting that PKG induced the dephosphorylation via activation of PP2A. To confirm further activation of PP2A by PKG in NHBE cells, cytosolic PP1 and PP2A activities were determined after exposure of the cells to 8-Br-cGMP. PP2A activity was increased approximately 3-fold (from 0.1 to 0.3 nmol/min/mg proteins, $p<0.01$) at concentrations of 8-Br-cGMP as low as 0.1 .mu.M, whereas PP1 activity remained unchanged. This data indicates that PP2A may be activated by PKG and is responsible for the dephosphorylation of MARCKS. Accordingly, this PP2A activity appeared critical for mucin secretion to occur; when PKG-induced MARCKS dephosphorylation was blocked by okadaic acid or fostriecin, the secretory response to PKC/PKG activation or UTP stimulation was ameliorated (FIG. 6).

MARCKS Associates with Actin and Myosin in the Cytoplasm

Figure 7:
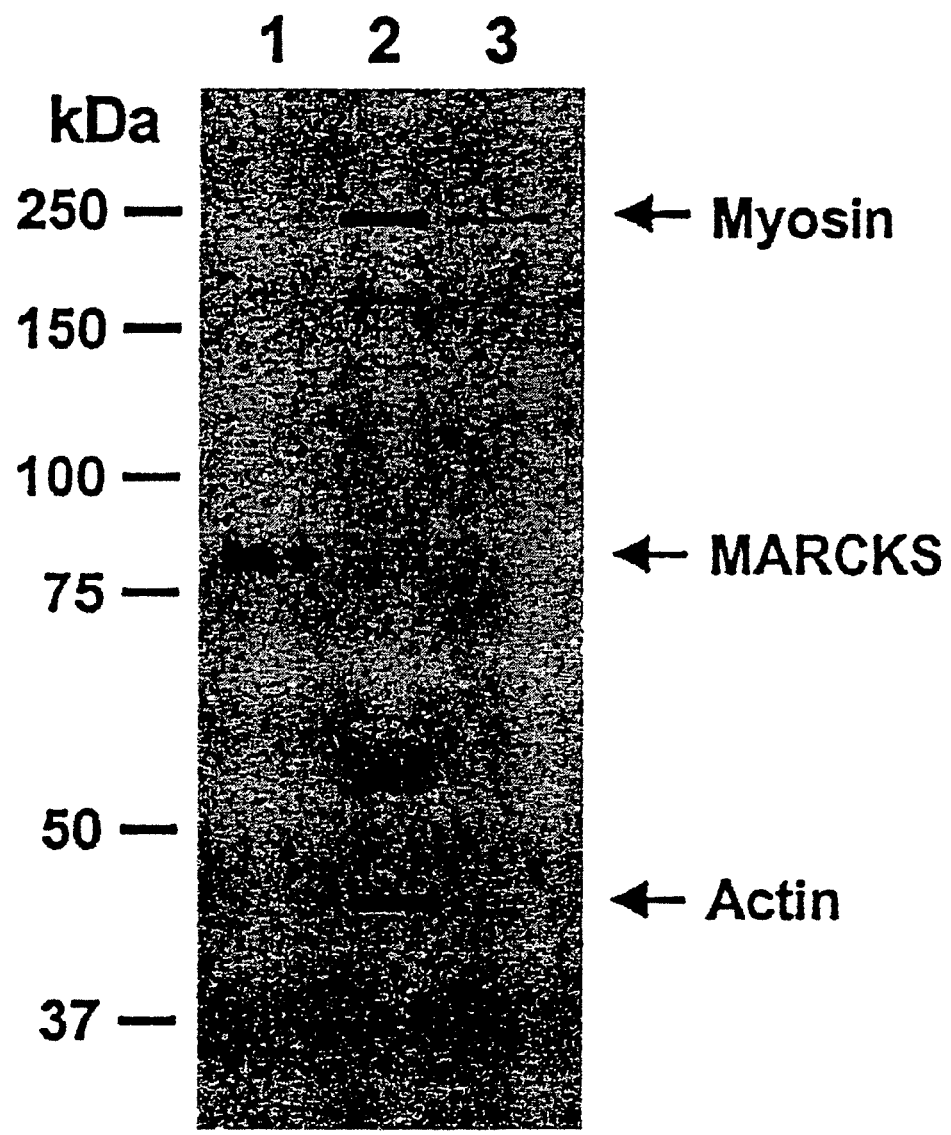
FIG. 7 is a gel that illustrates that MARCKS associates with actin and myosin in the cytoplasm.

FIG. 7 depicts a radiolabeled immunoprecipitation assay which reveals that MARCKS may associate with two other proteins (.about 0.200 and .about 0.40 kDa) in the cytoplasm. In FIG. 7 NHBE cells were labeled with [$^3$H]leucine and [$^3$H]proline overnight, and the membrane and the cytosol fractions were prepared as described under "Experimental Procedures." Isolated fractions were precleared with the non-immune control antibody (6F6). The cytosol was then divided equally into two fractions and used for immunoprecipitation carried out in the presence of 10 μM cytochalasin D (Biomol, Plymouth Meeting, Pa.) with the anti-MARCKS antibody 2F12 (lane 2) and the nonimmune control antibody 6F6 (lane 3), respectively. MARCKS protein in the membrane fraction was also assessed by immunoprecipitation using the antibody 2F12 (lane 1). The precipitated protein complex was resolved by 8% SDS-polyacrylamide gel electrophoresis and visualized by enhanced autoradiography. MARCKS appeared to associate with two cytoplasmic proteins with molecular masses of .about 200 and .about 40 kDa, respectively. These two MARCKS-associated proteins were excised from the gel and analyzed by matrix-assisted laser desorption ionization/time of flight mass spectrometry/internal sequencing (the Protein/DNA Technology Center of Rockefeller University, N.Y.). The obtained peptide mass and sequence data were used to search protein databases via Internet programs Pro-Found and MS-Fit. Results indicate that they are myosin (heavy chain, non-muscle type A) and actin, respectively. Matrix-assisted laser desorption ionization/time of flight mass spectrometry/internal sequence analysis indicates that these two MARCKS-associated proteins were myosin (heavy chain, non-muscle type A) and actin, respectively.

These studies suggest a new paradigm for the signaling mechanism controlling exocytotic secretion of airway mucin granules as well as providing what is believed to be the first direct evidence demonstrating a specific biological function of MARCKS in a physiological process. MARCKS serves as a key mediator molecule regulating mucin granule release in human airway epithelial cells. It is believed that elicitation of airway mucin secretion requires dual activation and synergistic actions of PKC and PKG. Activated PKC phosphorylates MARCKS, resulting in translocation of MARCKS from the inner face of the plasma membrane into the cytoplasm. Activation of PKG in turn activates PP2A, which dephosphorylates MARCKS in the cytoplasm. Because the membrane association ability of MARCKS is dependent on its phosphorylation state this dephosphorylation may allow MARCKS to regain its membrane-binding capability and may enable MARCKS to attach to membranes of cytoplasmic mucin granules. By also interacting with actin and myosin in the cytoplasm (FIG. 7), MARCKS may then be able to tether granules to the cellular contractile apparatus, mediating granule movement to the cell periphery and subsequent exocytotic release. The wide distribution of MARCKS suggests the possibility that this or a similar mechanism may regulate secretion of membrane-bound granules in various cell types under normal or pathological conditions.

Figure 9:
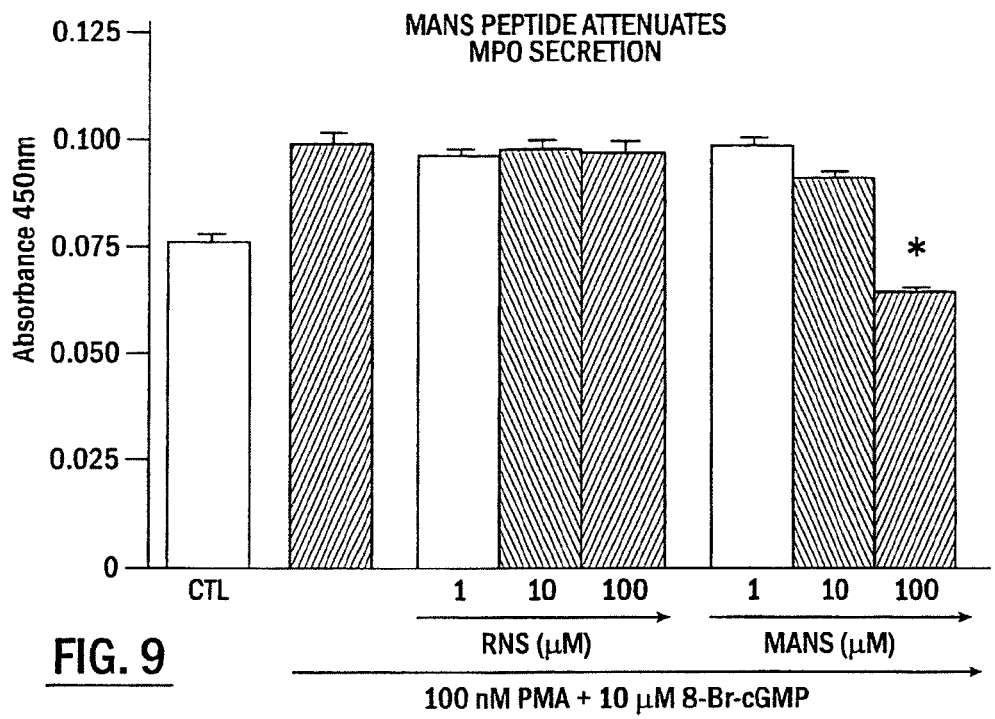
FIG. 9 is a bar graph depicting the ability of MANS peptide to block secretion of myloperoxidase from isolated canine neutrophils.
Figure 10:
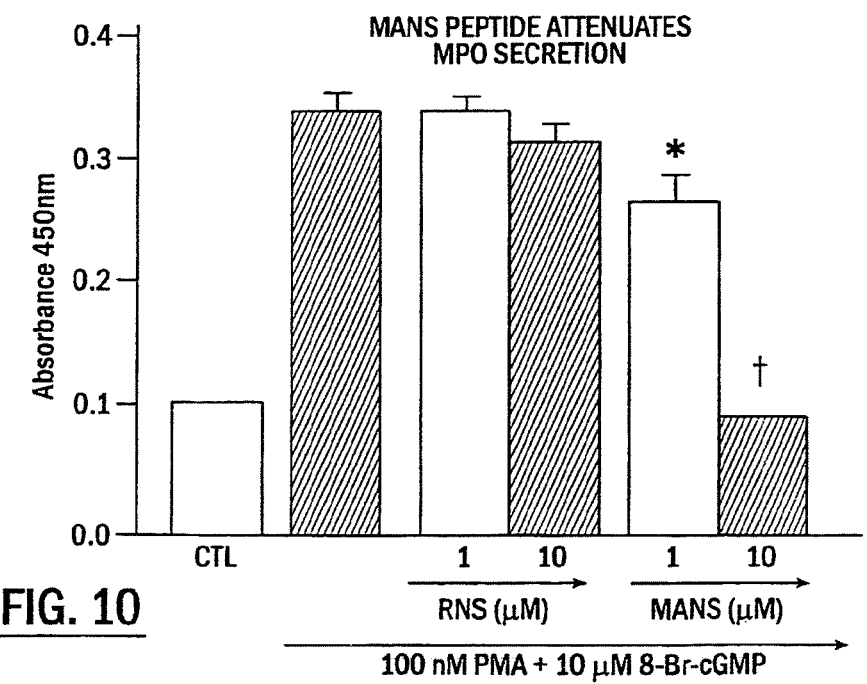
FIG. 10 is a bar graph depicting the ability of MANS peptide to block secretion of myloperoxidase from isolated human neutrophils.
Figure 11:
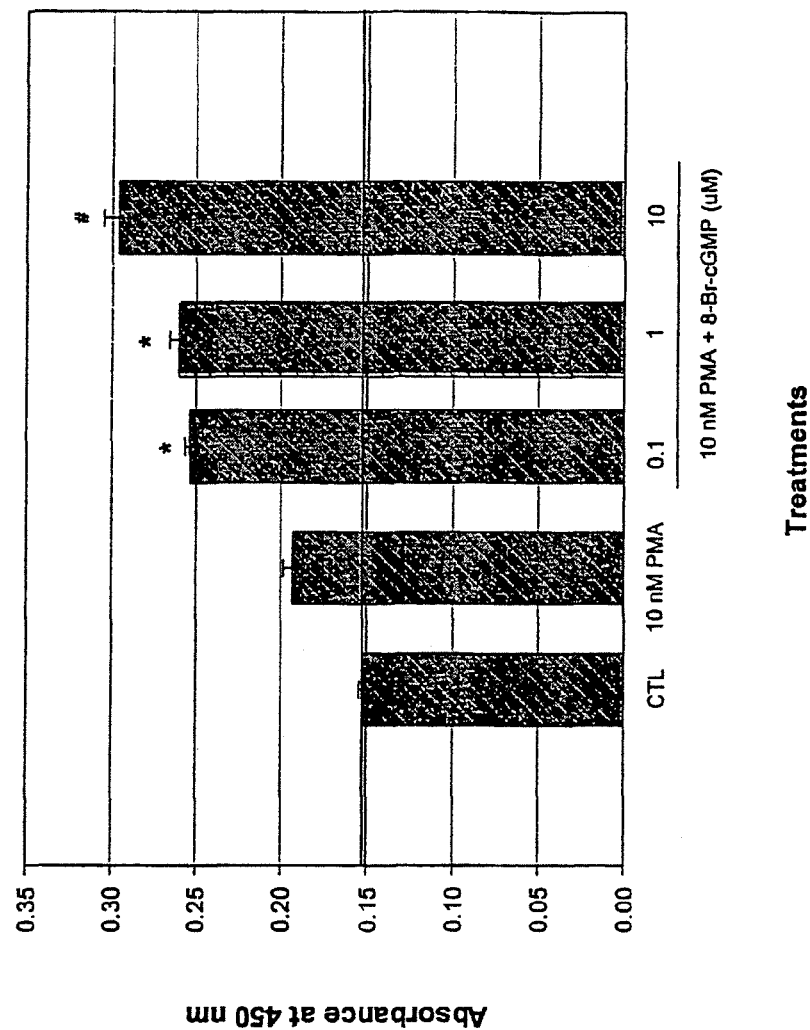
FIG. 11 is a bar graph showing that PMA stimulates a small increase in MPO secretion from LPS-stimulated human neutrophils which is enhanced in a concentration-dependent manner by co-stimulation with 8-Br-cGMP.
Figure 12:
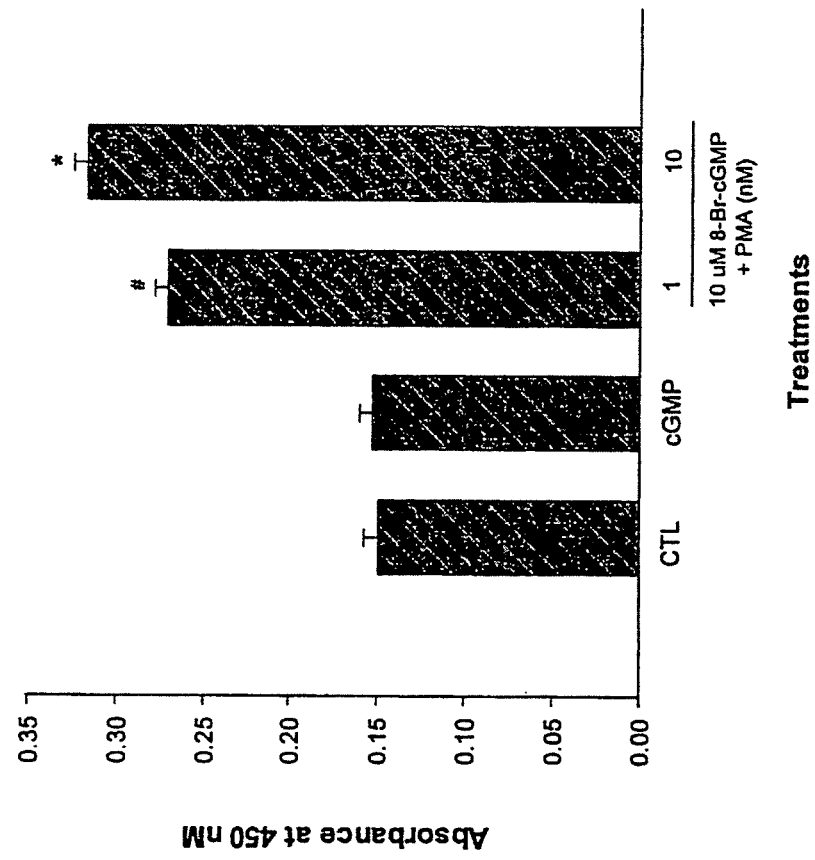
FIG. 12 is a bar graph showing that 8-Br-cGMP simulation has little effect on MPO secretion from LPS-stimulated human neutrophils until a co-stimulation with PMA occurs in a concentration-dependent manner.
Figure 13:
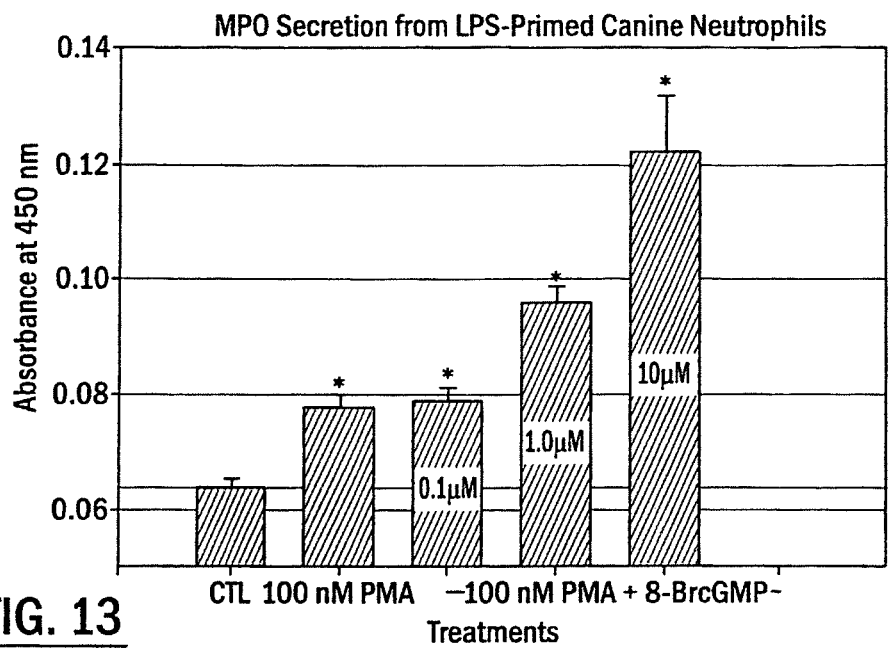
FIG. 13 is a bar graph showing that PMA stimulates a small increase in MPO secretion from LPS-stimulated canine neutrophils which is enhanced in a concentration-dependent manner by co-stimulation with 8-Br-cGMP.
Figure 14:
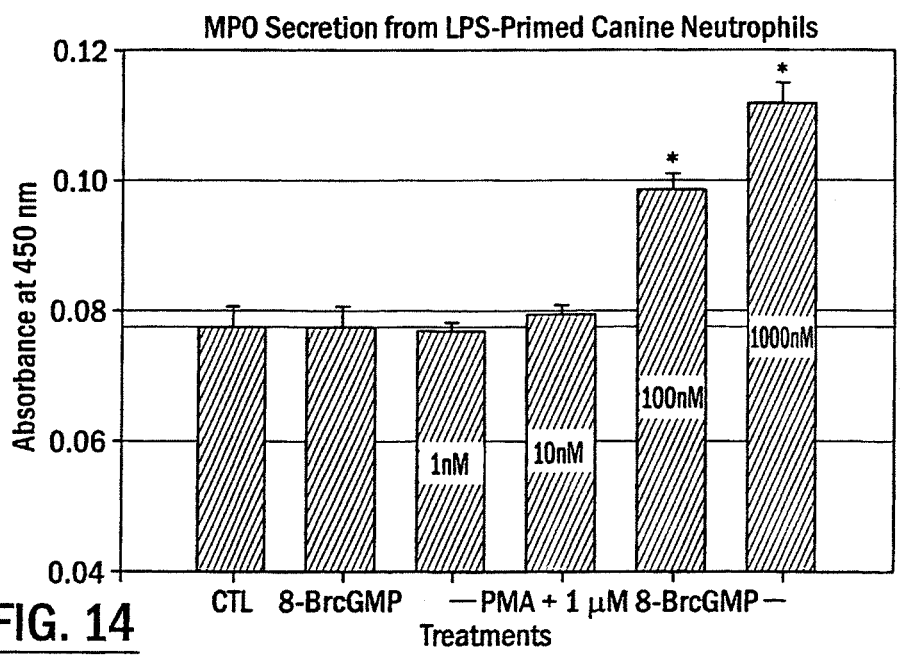
FIG. 14 is a bar graph showing that 8-Br-cGMP simulation has little effect on MPO secretion from LPS-stimulated canine neutrophils until a co-stimulation with PMA occurs in a concentration-dependent manner.
Figure 15:
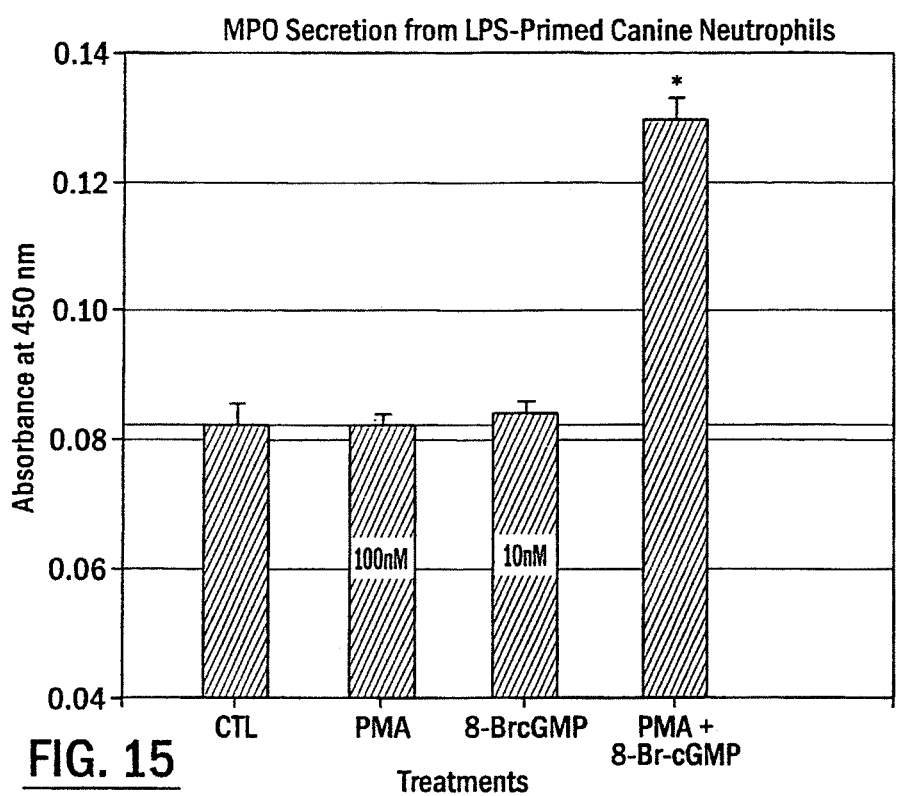
FIG. 15 is a bar graph showing that co-stimulation with PMA+8-Br-cGMP is required for maximal MPO secretion from LPS-stimulated canine neutrophils.

The invention also relates to a new method for blocking any cellular exocytotic secretory process, especially those releasing inflammatory mediators from granules contained within inflammatory cells, whose stimulatory pathways involve the protein kinase C (PKC) substrate MARCKS protein and release of contents from membrane-bound vesicles. Specifically, the inventors have shown that stimulated release of the inflammatory mediator myloperoxidase from human (FIG. 9) or canine (FIG. 10) neutrophils can be blocked in a concentration-dependent manner by the MANS peptide. Specifically, FIG. 9 shows isolated neutrophils that were stimulated to secrete myloperoxidase (MPO) with 100 nM PMA and 10 .mu.M 8-Br-cGMP. 100 μM MANS peptide decreased secretion of MPO to control levels (*=p<0.05). 10 μM MANS causes a slight decrease in MPO secretion. 10 or 100 μM of a control peptide (RNS) has no effect on MPO secretion. In FIG. 10, isolated neutrophils were stimulated to secrete myloperoxidase (MPO) with 100 nM PMA and 10 μM 8-Br-cGMP. 100 μM MANS peptide decreased secretion of MPO to control levels (*=p<0.05). 10 μM MANS causes a slight decrease in MPO secretion. 10 or 100 μM of a control peptide (RNS) has no effect on MPO secretion. Thus, the peptide may be used therapeutically to block the release of mediators of inflammation secreted from infiltrating inflammatory cells in any tissues. Many of these released mediators are responsible for the extensive tissue damage observed in a variety of chronic inflammatory diseases (i.e., respiratory diseases such as asthma, chronic bronchitis and COPD, inflammatory bowel diseases including ulcerative colitis and Crohn's disease, autoimmune diseases, skin diseases such as rosacea, eczema; and severe acne, arthritic and pain syndromes such as rheumatoid arthritis and fibromyalgia). This invention may be useful for treating diseases such as arthritis, chronic bronchitis, COPD and cystic fibrosis. This invention is accordingly useful for the treatment in both human and animal diseases, especially those affecting equines, canines, felines, and other household pets.

FIGS. 11-15 show MPO secretion for both humans and canines. In all of these experiments, isolated neutrophils were stimulated with LPS at a concentration of $1 \times 10^{-6}$ M for 10 minutes at 37° C. prior to adding the stimuli as indicated in the figures. The LPS primes the cells so they can respond to a secretagogue.

In one embodiment, this invention discloses a method of regulating an inflammation in a subject comprising administering a therapeutically effective amount of a pharmaceutical composition comprising a MANS peptide or an active fragment thereof. In one aspect of this embodiment, said active fragment of the MANS protein comprises at least six amino acids. In another aspect, said inflammation is caused by respiratory diseases, bowel diseases, skin diseases, autoimmune diseases and pain syndromes. In another aspect, said respiratory diseases are selected from the group consisting of asthma, chronic bronchitis, and COPD. In another aspect, said bowel diseases are selected from the group consisting of ulcerative colitis, Crohn's disease and irritable bowel syndrome. In another aspect, said skin diseases are selected from the group consisting of rosacea, eczema, psoriasis and severe acne. In another aspect, said inflammation is caused by arthritis or cystic fibrosis. In another aspect, said subject is a mammal. Additionally, in another aspect, said mammal is selected from the group consisting of humans, canines, equines and felines. In another aspect, said administering step is selected from the group consisting of topical administration, parenteral administration, rectal administration, pulmonary administration, nasal administration, inhalation and oral administration. In another aspect, said pulmonary administration is selected from the group of aerosol, dry powder inhaler, metered dose inhaler, and nebulizer.

In another embodiment, this invention discloses a method for regulating a cellular secretory process in a subject comprising administering a therapeutically effective amount of a pharmaceutical composition comprising at least one compound comprising a MANS peptide or an active fragment thereof, that regulates an inflammatory mediator in a subject. In one aspect of this embodiment, said active fragment of the MANS protein comprises at least six amino acids. In another aspect, said regulating a cellular secretory process is blocking or reducing a cellular secretory process. In another aspect, said inflammatory mediator is caused by respiratory diseases, bowel diseases, skin diseases, autoimmune diseases and pain syndromes. In another aspect, said respiratory diseases are selected from the group consisting of asthma, chronic bronchitis, and COPD. In another aspect, said bowel diseases are selected from the group consisting of ulcerative colitis, Crohn's disease and irritable bowel syndrome. In another aspect, said skin diseases are selected from the group consisting of rosacea, eczema, psoriasis and severe acne. In another aspect, said inflammatory mediator is caused by arthritis or cystic fibrosis. In another aspect, said subject is a mammal. In another aspect, said mammal is selected from the group consisting of humans, canines, equines and felines. In another aspect, said administering step is selected from the group consisting of topical administration, parenteral administration, rectal administration, pulmonary administration, nasal administration, inhalation and oral administration. In another aspect, said pulmonary administration is selected from the group of aerosol, dry powder inhaler, metered dose inhaler, and nebulizer.

In another embodiment, this invention discloses a method of reducing inflammation in a subject comprising administering a therapeutically effective amount of a compound that inhibits the MARCKS-related release of inflammatory mediators, whereby the release of inflammatory mediators in the subject is reduced compared to that which would occur in the absence of said treatment. In one aspect of this embodiment, said compound is at least one active fragment of a MARCKS protein. In another aspect, said active fragment is at least six amino acids in length. In another aspect, said compound is a MANS peptide or an active fragment thereof. In another aspect, said compound is an antisense oligonucleotide directed against the coding sequence of a MARCKS protein or an active fragment thereof. In another aspect, said active fragment is at least six amino acids in length.

In another embodiment, this invention discloses a method of reducing inflammation in a subject comprising administering a therapeutically effective amount of a pharmaceutically active composition comprising a compound that inhibits the MARCKS-related release of inflammatory mediators, whereby the inflammation in the subject is reduced compared to that which would occur in the absence of said treatment. In one aspect of this embodiment, said compound is an active fragment of a MARCKS protein. In another aspect, said active fragment is at least six amino acids in length. In another aspect, said compound is a MANS peptide or an active fragment thereof. In another aspect, said compound is an antisense oligonucleotide directed against the coding sequence of a MARCKS protein or an active fragment thereof. In another aspect, said active fragment is at least six amino acids in length. The present invention is intended to encompass a composition that contains one or more of the MANS peptide or its active fragments and use thereof in the treatment of inhibiting the release of inflammatory mediators from granules or vesicles of inflammatory cells.

In another embodiment, this invention discloses a method of regulating mucin granule release in a subject comprising administering a compound that regulates mucin granule release, whereby mucin granules are reduced as compared to that which would occur in the absence of said mucin granules. In one aspect of this embodiment, said compound is an active fragment of a MARCKS protein. In another aspect, said compound is a MANS peptide.

In another embodiment, this invention discloses a method of regulating exocytotic secretion of airway mucin granules in a subject comprising: administering a compound that regulates mucin granule release, whereby mucin granules are reduced as compared to that which would occur in the absence of said mucin granules. In one aspect of this embodiment, said compound is an active fragment of a MARCKS protein. In another aspect, said compound is a MANS peptide.

In another embodiment, this invention discloses a method of modulating mucus secretion in a subject comprising: administering a therapeutic amount of an antisense sequence that are complementary to sequences encoding a MARCKS protein or an active fragment thereof, wherein mucus secretion by said cell is inhibited compared to that which would occur in the absence of such administration. In one aspect of this embodiment, said sequence is at least eighteen nucleic acids in length. In another aspect, said compound is complementary to sequences encoding a MANS peptide or an active fragment thereof. In another aspect, said modulating mucus secretion is blocking or reducing mucus secretion.

In another embodiment, this invention discloses a method of reducing or inhibiting inflammation in a subject comprising administering a therapeutically effective amount of at least one peptide comprising MANS peptide or an active fragment thereof effective to modulate an inflammatory mediator at the inflammation site. In one aspect of this embodiment, said active fragment is at least six amino acids in length. In another aspect, said inflammatory mediators are produced by cells selected from the group consisting of neutrophils, basophils, eosinophils, monocytes and leukocytes. Preferably the cells are leukocytes, more preferably granulocytes, and even more preferably neutrophils, basophils, eosinophils or a combination thereof. In another aspect, the agent is administered orally, parenterally, cavitarily, rectally or through an air passage. In another aspect, said composition further comprises a second molecule selected from the group consisting of an antibiotic, an antiviral compound, an antiparasitic compound, an anti-inflammatory compound, and an immunosuppressant.

An active fragment of a MANS peptide can be selected from the group consisting of the myristoylated peptides of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO 19.

In another aspect of this invention, the methods disclosed in this invention can be accomplished by use of or administering of combinations of the peptides disclosed in the invention, i.e., by use of or administering of a peptide selected from the group consisting of SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO 19, and combinations thereof. Preferably a single peptide is used or administered in the methods disclosed herein.

In response to protein kinase C (PKC) activation by an inflammatory stimulant, degranulation in a cell selected from the group consisting of neutrophils, eosinophils, monocytes/macrophages and lymphocytes can be attenuated by pre-incubation and by co-incubation with a peptide identical to the N-terminal region of MARCKS protein, wherein the peptide is selected from the group consisting of the MANS peptide (SEQ ID NO: 1) and myristoylated N-terminal fragments thereof (SEQ ID NO: 3 to 19). Although time courses and concentrations can vary among cell types, in all cases the MANS peptide attenuates PKC-induced degranulation.

Methods and Materials

NHBE Cell Culture—

Expansion, cryopreservation, and culture of NHBE cells in the air/liquid interface were performed as described previously. See, Krunkosky et al. Briefly, NHBE cells (Clonetics, San Diego, Calif.) were seeded in vented T75 tissue culture flasks (500 cells/cm$^2$) and cultured until cells reached 75-80% confluence. Cells were then dissociated by trypsin/EDTA and frozen as passage-2. Air/liquid interface culture was initiated by seeding passage-2 cells ($2\times10^4$ cells/cm$^2$) in TRANSWELL® clear culture inserts (Costar, Cambridge, Mass.) that were thinly coated with rat tail collagen, type I (Collaborative Biomedical, Bedford, Mass.). Cells were cultured submerged in medium in a humidified 95% air, 5% $CO_2$ environment for 5-7 days until nearly confluent. At that time, the air/liquid interface was created by removing the apical medium and feeding cells basalaterally. Medium was renewed daily thereafter. Cells were cultured for an additional 14 days to allow for full differentiation.

Measurement of Mucin Secretion by ELISA—

Before collection of "base line" and "test" mucin samples, the accumulated mucus at the apical surface of the cells was removed by washing with phosphate-buffered saline, pH 7.2. To collect the base-line secretion, cells were incubated with medium alone, and secreted mucin in the apical medium was collected and reserved. Cells were rested for 24 h and then exposed to medium containing the selected stimulatory and/or inhibitory reagents (or appropriate controls), after which secreted mucin was collected and reserved as the test sample. Incubation times for the base line and the test were the same but varied depending on the test reagent utilized. Both base line and test secretions were analyzed by ELISA using an antibody capture method as known in the art. See, e.g., Harlow et al., Antibodies: *A Laboratory Manual*, pp. 570-573, Cold Spring Harbor Laboratory, Cold Spring Harbor, N.Y. (1988). The primary antibody for this assay was 17Q2 (Babco, Richmond, Calif.), a monoclonal antibody that reacts specifically with a carbohydrate epitope on human airway mucins. The ratio of test/base-line mucin, is similar to a "secretory index", was used to quantify mucin secretion, allowing each culture dish to serve as its own control and thus, minimizing deviation caused by variability among culture wells. Wright et al., *Am. J. Physiol.* 271, L854-L861 (1996). Levels of mucin secretion were reported as percentage of the medium control.

Radiolabeled Immunoprecipitation Assay—

When labeling with [$^{32}$P]phosphate, cells were preincubated for 2 h in phosphate-free Dulbecco's modified Eagle's medium containing 0.2% bovine serum albumin and then labeled with 0.1 mCi/ml [$^{32}$P]orthophosphate (9000 Ci/mmol, PerkinElmer Life Sciences) for 2 h. For labeling with [$^3$H]myristic acid or $^3$H-amino acids, cells were incubated overnight in medium containing 50 µCi/ml [$^3$H]myristic acid (49 Ci/mmol, PerkinElmer Life Sciences) or 0.2 mCi/ml [$^3$H]leucine (159 Ci/mmol, PerkinElmer Life Sciences) plus 0.4 mCi/ml [$^3$H]proline (100 Ci/mmol, PerkinElmer Life Sciences). Following labeling, cells were exposed to stimulatory reagents for 5 mM. When an inhibitor was used, cells were preincubated with the inhibitor for 15 min prior to stimulation. At the end of the treatments, cells were lysed in a buffer containing 50 mM Tris-HCl (pH 7.5), 150 mM NaCl, 1 mM EDTA, 10% glycerol, 1% Nonidet P-40, 1 mM phenylmethylsulfonyl fluoride, 1 mM benzamidine, 10 µg/ml pepstatin A, and 10 µg/ml leupeptin. Trichloroacetic acid precipitation and scintillation counting may determine the radiolabeling efficiency in each culture. Immunoprecipitation of MARCKS protein was carried out according to the method of Spizz and Blackshear using cell lysates containing equal counts/min. Spizz et al., *J. Biol. Chem.* 271, 553-562 (1996). Precipitated proteins were resolved by 8% SDS-polyacrylamide gel electrophoresis and visualized by autoradiography. Anti-human MARCKS antibody (2F12) and nonimmune control antibody (6F6) were used in this assay.

To assess MARCKS or MARCKS-associated protein complexes in different subcellular fractions, radiolabeled and treated cells were scraped into a homogenization buffer (50 mM Tris-HCl (pH 7.5), 10 mM NaCl, 1 mM EDTA, 1 mM phenylmethylsulfonyl fluoride, 1 mM benzamidine, 10 µg/ml pepstatin A, 10 µg/ml leupeptin) and then disrupted by nitrogen cavitation (800 pounds/square inch for 20 min at 4° C.). Cell lysates were centrifuged at 600×g for 10 min at 4° C. to remove nuclei and unbroken cells. Post-nuclear supernatants were separated into membrane and cytosol fractions by ultracentrifugation at 400,000×g for 30 min at 4° C. The membrane pellet was solubilized in the lysis buffer by sonication. Immunoprecipitation was then carried out as described above.

MARCKS-Related Peptides—

Both the myristoylated N-terminal sequence (MANS) and the random N-terminal sequence (RNS) peptides were synthesized at Genemed Synthesis, Inc. (San Francisco, Calif.), then purified by high pressure liquid chromatography (>95% pure), and confirmed by mass spectroscopy with each showing one single peak with an appropriate molecular mass. The MANS peptide consisted of sequence identical to the first 24 amino acids of MARCKS, i.e. the myristoylated N-terminal region that mediates MARCKS insertion into membranes, MA-GAQFSKTAAKGEAAAERPGEAAVA (SEQ ID NO: 1 (where MA=N-terminal myristate chain). The corresponding control peptide (RNS) contained the same amino acid composition as the MANS but arranged in random order, MA-GTAPAAEGAGAEVKRASAEAKQAF (SEQ ID NO: 2). The presence of the hydrophobic myristate moiety in these synthetic peptides enhances their permeability to the plasma membranes, enabling the peptides to be taken up readily by cells. To determine the effects of these peptides on mucin secretion, cells were preincubated with the peptides for 15 min prior to addition of secretagogues, and mucin secretion was then measured by ELISA.

Antisense Oligonucleotides—

MARCKS antisense oligonucleotide and its corresponding control oligonucleotide were synthesized at Biognostik GmbH (Gottingen, Germany). NHBE cells were treated with 5 µM antisense or control oligonucleotide apically for 3 days (in the presence of 2 µg/ml lipofectin for the first 24 h). Cells were then incubated with secretagogues, and mucin secretion was measured by ELISA. Total RNA and protein were isolated from treated cells. MARCKS mRNA was assessed by Northern hybridization according to conventional procedures using human MARCKS cDNA as a probe. MARCKS protein level was determined by Western blot using purified anti-MARCKS IgG1 (clone 2F12) as the primary detection antibody.

Transient Transfection—

The phosphorylation site domain (PSD) of MARCKS contains the PKC-dependent phosphorylation sites and the actin filament-binding site. To construct a PSD-deleted MARCKS cDNA, two fragments flanking the PSD sequence (coding for 25 amino acids) were generated by polymerase chain reaction and then ligated through the XhoI site that was attached to the 5'-ends of oligonucleotide primers designed for the polymerase chain reaction. The resultant mutant cDNA and the wild-type MARCKS cDNA were each inserted into a mammalian expression vector pcDNA4/TO (Invitrogen, Carlsbad, Calif.). Isolated recombinant constructs were confirmed by restriction digests and DNA sequencing.

HBE1 is a papilloma virus-transformed human bronchial epithelial cell line capable of mucin secretion when cultured in air/liquid interface. Transfection of HBE1 cells was carried out using the Effectene transfection reagent (Qiagen, Valencia, Calif.) according to the manufacturer's instructions. Briefly, differentiated HBE1 cells grown in air/liquid interface were dissociated by trypsin/EDTA and re-seeded in 12-well culture plates at $1 \times 10^5$ cells/cm². After overnight incubation, cells were transfected with the wild-type MARCKS cDNA, the PSD-truncated MARCKS cDNA, or vector DNA. Cells were cultured for 48 h to allow gene expression and then exposed to secretagogues and mucin secretion measured by ELISA. All transfections were carried out in the presence of pcDNA4/TO/lacZ plasmid (Invitrogen) (DNA ratio 6:1, total 1 µg DNA, ratio of DNA to Effectene reagent=1:25) to monitor variations in transfection efficiency. Results showed no significant difference in .beta.-galactosidase activities in cell lysates isolated from the transfected cells, indicating similar transfection efficiency among different DNA constructs (data not shown).

Protein Phosphatase Activity Assay—

PP1 and PP2A activities were measured using a protein phosphatase assay system (Life Technologies, Inc.) as known in the art with slight modification. Huang et al., Adv. Exp. Med. Biol. 396, 209-215 (1996). Briefly, NHBE cells were treated with 8-Br-cGMP or medium alone for 5 min. Cells were then scraped into a lysis buffer (50 mM Tris-HCl (pH 7.4), 0.1% .beta.-mecaptoethanol, 0.1 mM EDTA, 1 mM benaamidine, 10 µg/ml pepstatin A, 10 µg/ml leupeptin) and disrupted by sonication for 20 s at 4° C. Cell lysates were centrifuged and the supernatants saved for phosphatase activity assay. The assay was performed using $^{32}$P-labeled phosphorylase A as a substrate. Released $^{32}P_i$ was counted by scintillation. The protein concentration of each sample was determined by the Bradford assay. PP2A activity was expressed as the sample total phosphatase activity minus the activity remaining in the presence of 1 nM okadaic acid. PP1 activity was expressed as the difference between the activities remaining in the presence of 1 nM and 1 µM okadaic acid, respectively. Protein phosphatase activities were reported as nmol of $P_i$ released per min/mg total protein.

Cytotoxicity Assay—

All reagents used in treating NHBE cells were examined for cytotoxicity by measuring the total release of lactate dehydrogenase from the cells. The assay was carried out using the Promega Cytotox 96 Kit according to the manufacturer's instructions. All experiments were performed with reagents at non-cytotoxic concentrations.

Statistical Analysis—

Data were analyzed for significance using one-way analysis of variance with Bonferroni post-test corrections. Differences between treatments were considered significant at $p<0.05$.

Isolation of PMNs from Canine Blood—

The steps involved in isolating PMN include collecting 10 ml ACD anticoagulated blood. Then layering 5 ml on 3.5 ml PMN isolation media while ensuring that the PMN isolation media (IM) was at room temperature (RI). Next, the blood was centrifuged at room temperature for 30', 550×g at 1700 RPMs. The low lower white band was transferred into 15 ml conical centrifuge tube (CCFT). Next, 2V HESS with 10% fetal bovine serum (PBS) was added and centrifuged at room temperature for 10', 400×g at 1400 RPMs. The pellet was then resuspended in 5 ml 1-LESS with PBS. The cell suspension was added to 50 ml CCFT containing 20 ml of ice cold 0.88% NH₄Cl and inverted two to three times. The resulting product was centrifuged for 10', 800×g at 2000 RPMs, then aspirated and resuspended in 5 ml HBSS with FBS. The prep was examined by counting and cytospin and preferably for whole blood, the cell number should be between $10^9$-$10^{11}$ cells and for PMNs, cell number should be between 2-4×$10^7$ cells. See generally, Wang et al., J. Immunol., "Neutrophil-induced changes in the biomechanical properties of endothelial cells: roles of ICAM-1 and reactive oxygen species," 6487-94 (2000).

MPO Colorimetric Enzyme Assay—

Samples were assayed for MPO activity in 96 well round bottom microtiter plates using a sandwich ELISA kit (R & D Systems, Minneapolis, Minn.). Briefly, 20 microliters of sample is mixed with 180 microliters of substrate mixture containing 33 mM potassium phosphate, pH 6.0, 0.56% Triton X-100, 0.11 mM hydrogen peroxide, and 0.36 mM O-Dianisidine Dihydrochloride in an individual microtiter well. The final concentrations in the assay mixture are: 30 mM potassium phosphate, pH 6.0, 0.05% Triton X-100, 0.1 mM hydrogen peroxide, and 0.32 mM O-Diannisidine Dihydrochloride. After mixing, the assay mixture was incubated at room temperature for 5 minutes, and MPO enzyme activity determined spectrophotometrically at 550 nanometers. Samples were assayed in duplicate.

Inflammatory Mediator Secretion Studies

Four different leukocyte types or models that secrete specific granule contents in response to phorbol ester induced activation of PKC were used. Neutrophils were isolated from human blood and in vitro release of MPO by these cells was assessed. Release of membrane-bound inflammatory mediators from commercially-available human leukocyte cell lines was also evaluated. The human promyelocytic cell line HL-60 clone 15 was used to assess secretion of EPO (Fischkoff S A. Graded increase in probability of eosinophilic differentiation of HL-60 promyelocytic leukemia cells induced by culture under alkaline conditions. Leuk Res 1988; 12:679-686; Rosenberg H F, Ackerman S J, Tenen D G. Human eosinophil cationic protein: molecular cloning of a cytotoxin and helminthotoxin with ribonuclease activity. J Exp Med 1989; 170:163-176; Tiffany H L, Li F, Rosenberg H F. Hyperglycosylation of eosinophil ribonucleases in a promyelocytic leukemia cell line and in differentiated peripheral blood progenitor cells. J Leukoc Biol 1995; 58:49-54; Badewa A P, Hudson C E, Heiman A S. Regulatory effects of eotaxin, eotaxin-2, and eotaxin-3 on eosinophil degranulation and superoxide anion generation. Exp Biol Med 2002; 227:645-651). The monocytic leukemia cell line U937 was used to assess secretion of lysozyme (Hoff T, Spencker T, Emmendoerffer A., Goppelt-Struebe M. Effects of glucocorticoids on the TPA-induced monocytic differentiation. J Leukoc Biol 1992; 52:173-182; Balboa M A, Saez Y, Balsinde J. Calcium-independent phospholipase A2 is required for lysozyme secretion in U937 promonocytes. J Immunol 2003; 170: 5276-5280; Sundstrom C, Nilsson K. Establishment and characterization of a human histiocytic lymphoma cell line (U-937). Int J Cancer 1976; 17:565-577). The lymphocyte natural killer cell line NK-92 used to assess release of granzyme (Gong J H., Maki G, Klingemann H G. Characterization of a human cell line (NK-92) with phenotypical and functional characteristics of activated natural killer cells. Leukemia 1994; 8:652-658; Maki G, Klingemann H G, Martinson J A, Tam Y K. Factors regulating the cytotoxic activity of the human natural killer cell line, NK-92. J Hemather Stem Cell Res 2001; 10:369-383; Takayama H, Trenn G, Sitkovsky M V. A novel cytotoxic T lymphocyte activation assay. J Immunol Methods 1987; 104:183-190). In all cases, the cells were preincubated with a range of concentrations of a synthetic peptide identical to the 24 amino acid MARCKS N-terminus (MANS-myristoylated N-terminal sequence peptide; MA-GAQFSKTAAKGEAAAERPGEAAVA wherein MA is myristoyl attached to the N-terminal amine of the peptide by an amide bond), or a missense control peptide (RNS: Random N-terminal sequence peptide; MA-GTA-PAAEGAGAEVKRASAEAKQAF,) which consists of the same 24 amino acids but arranged in random order sequence which possesses less than 13% sequence identity to the MANS peptide sequence.

In each of the cell types, MANS, but not RNS, attenuates release of inflammatory mediators in a concentration-dependent manner. A useful time course of observation is 0.5-3.0 hrs. The results are consistent with the N-terminal region of the MARCKS protein being involved in intracellular pathways leading to leukocyte degranulation.

Human Neutrophil Isolation—

These studies were approved by the NCSU human studies Institutional Review Board (IRB). Human neutrophils were isolated as previously described (see Takashi S, Okubo Y, Horie S. Contribution of CD54 to human eosinophil and neutrophil superoxide production. J Appl Physiol 2001; 91:613-622) with slight modifications. Briefly, heparinized venous blood was obtained from normal healthy volunteers, diluted with RPMI-1640 (Cellgro; Mediatech, Inc., Herndon, Va.) at a ratio of 1:1, layered onto a Histopaque (density, 1.077 g/ml; Sigma-Aldrich Co., St. Louis, Mo.) and centrifuged at 400 g for 20 min at 4° C. The supernatant and mononuclear cells at the interface were carefully removed, and erythrocytes in the sediment were lysed in chilled distilled water. Isolated granulocytes were washed twice with Hanks' balanced salts solution (HBSS) and resuspended in HBSS on ice. The neutrophils used for the experiments were of >98% purity with <2% contamination by eosinophils, and the viability was >99% as determined by Trypan blue dye exclusion.

Measurement of Released Neutrophil MPO Activity—

For measurement of MPO release, purified human neutrophils suspended in HBSS were aliquoted at $4 \times 10^6$ cells/ml in 15 ml tubes and preincubated with either 50 or 100 μM of MANS or RNS peptide for 10 min at 37° C. The cells then were stimulated with 100 nM phorbol 12-myristate 13-acetate (PMA) for up to 3 hrs. A control reference (PMA control reference) was established using purified human neutrophils suspended in HBSS aliquoted at $4 \times 10^6$ cells/ml in 15 ml tubes and stimulated with 100 nM phorbol 12-myristate 13-acetate (PMA) in the absence of MANS or RNS peptide for the same time periods. The reaction was terminated by placing the tubes on ice and centrifugation at 400 g for 5 min at 4° C.

MPO activity in the cell supernatant was assayed using tetramethylbenzidine (TMB) based on a previously established technique (Abdel-Latif D, Steward M, Macdonald D L, Francis G A., Dinauer M C, Lacy P. Rac2 is critical for neutrophil primary granule exocytosis. Blood 2004; 104:832-839). Briefly, 100 μl of TMB substrate solution was added to 50 μl of cell supernatants or standard human MPO (EMD Biosciences, Inc., San Diego, Calif.) in a 96-well microplate followed by incubation at room temperature for 15 min. The reaction was terminated by addition of 50 μl of 1M $H_2SO_4$ and absorbance was read at 450 nm in a spectrophotometric microplate reader (VERSA max, Molecular Devices, Sunnyvale, Calif.).

Leukocyte Culture Studies.

Three types of human leukocyte cell lines, specifically the promyelocytic cell line HL-60 clone 15, the monocytic cell line U937, and the lymphocyte natural killer cell line NK-92 were purchased from American Type Culture Collection (ATCC; Rockville, Md.). HL-60 clone 15 cells (ATCC CRL-1964) were maintained in medium consisting of RPMI 1640 with L-glutamine supplemented with 10% heat-inactivated fetal bovine serum (FBS; Gibco; Invitrogen Co., Carlsbad, Calif.), 50 IU/ml penicillin, 50 μg/ml streptomycin, and 25 mM HEPES buffer, pH 7.8, at 37° C. in an atmosphere containing 5% CO2. Final differentiation to an eosinophil-like phenotype was initiated by culturing cells at 5×10$^5$ cells/ml in the above medium containing 0.5 mM butyric acid (Sigma-Aldrich Co.) for 5 days as previously described (Tiffany H L, Li F, Rosenberg H F. Hyperglycosylation of eosinophil ribonucleases in a promyelocytic leukemia cell line and in differentiated peripheral blood progenitor cells. J Leukoc Biol 1995; 58:49-54; Tiffany H L, Alkhatib G, Combadiere C, Berger E A, Murphy P M. CC chemokine receptors 1 and 3 are differentially regulated by IL-5 during maturation of eosinophilic HL-60 cells. J Immunol 1998; 160:1385-1392). U937 cells (ATCC CRL-1593.2) were grown at 37° C. in an atmosphere of 5% $CO_2$ in complete medium consisting of RPMI 1640 with L-glutamine supplemented with 10% FBS, 50 IU/ml penicillin, and 50 µg/ml streptomycin. NK-92 cells (ATCC CRL-2407) were maintained in alpha-MEM medium (Sigma-Aldrich Co.) supplemented with 20% FBS, 100 U/ml of interleukin-2 (IL-2) (Chemicon International, Inc., Temecula, Calif.), 5×10$^{-5}$ M of 2-mercaptoethanol, 50 IU/ml penicillin, and 50 µg/ml streptomycin at 37° C. in an atmosphere containing 5% $CO_2$. Cell morphology was judged by assessment of Wright-Giemsa-stained cells. Viability of cells harvested for experiments was assessed by trypan blue exclusion and populations of cells with viability >95% were used.

Incubation of Cells for Degranulation Assays.

HL-60 clone 15, U937, and NK-92 cells were washed and resuspended at 2.5×10$^6$ cells/ml in phenol red-free RPMI-1640 (Cellgro; Mediatech, Inc.) for all degranulation assays. Aliquots of cells in 15 ml tubes were preincubated with indicated concentrations of MANS or RNS peptide for 10 min at 37° C. The cells then were stimulated with PMA for up to 2 hr. A control reference (PMA control reference) was established for each cell type using HL-60 clone 15, U937, and NK-92 cells, respectively, which were washed and resuspended at 2.5×10$^6$ cells/ml in phenol red-free RPMI-1640 and stimulated with PMA but in the absence of MANS or RNS peptide for the same time periods. The reaction was terminated by placing tubes on ice and centrifuging cells at 400 g for 5 min at 4° C.

For measurements of released MPO from neutrophils and released lysozyme from U937 cells, we were able to quantify secretion by using as standards human MPO and egg white ovalbumin, respectively. For released EPO from HL-60 clone 15 cells and for released granzyme from NK-92 cells, no standards were available to use for quantification. Hence, both released and intracellular (from lysed cells) levels of EPO and granzyme were measured, and the released EPO and granzyme were expressed as a percentage of total (intracellular and released) for each. To measure intracellular EPO in HL-60 clone 15 cells and intracellular granzyme in NK-92 cells, appropriate aliquots of 0.1% triton X-100-lysed cells were taken for quantification of intracellular granule proteins as described below. All treatments were expressed as percentage of control to minimize variability between cultures.

Measurement of HL-60 EPO Release.

EPO activity released by HL-60 clone 15 cells was assayed using TMB according to a previously established technique (Lacy P, Mahmudi-Azer S, Bablitz B, Hagen S C, Velazquez J R, Man S F, Moqbel R. Rapid mobilization of intracellularly stored RANTES in response to interferon-gamma in human eosinophils. Blood 1999; 94:23-32). Thus, 100 µl of TMB substrate solution was added to 50=microliters) of sample in a 96-well microplate and incubated at room temperature for 15 min (min=minutes). The reaction was terminated by addition of 50 µl of 1.0M $H_2SO_4$ and absorbance was read at 450 nm (nm=nanometers) in a spectrophotometric microplate reader. The amount of secreted EPO was expressed as percentage of total content, using the amount obtained in the same number of triton X-100-lysed cells.

Measurement of Monocyte Lysozyme Secretion.

Lysozyme secreted by U937 cells was measured using a spectrophotometric assay as described previously (Balboa M A, Saez Y, Balsinde J. Calcium-independent phospholipase A2 is required for lysozyme secretion in U937 promonocytes. J Immunol 2003; 170:5276-5280) with slight modification. Thus, 100 µl of sample was mixed with 100 µl of a *Micrococcus lysodeikticus* (Sigma-Aldrich Co.) suspension (0.3 mg/ml in 0.1 M sodium phosphate buffer, pH 7.0) in a 96-well microplate. The decrease in absorbance at 450 nm was measured at room temperature. A calibration curve was constructed using chicken egg white lysozyme (EMD Biosciences, Inc.) as a standard.

Measurement of NK Cell Granzyme Secretion.

Granzyme secreted from NK-92 cells was assayed by measuring hydrolysis of Na-benzyloxycarbonyl-L-lysine thiobenzyl ester (BLT) essentially as described previously (Takayama H, Trenn G, Sitkovsky M V. A novel cytotoxic T lymphocyte activation assay. J Immunol Methods 1987; 104: 183-190). 50 µl of supernatant was transferred to a 96-well plate, and 150 µl of BLT solution (0.2 mM BLT; EMD Biosciences, Inc., and 0.22 mM DTNB; Sigma-Aldrich Co.) (mM=millimolar) in phosphate-buffered saline (PBS, pH 7.2) was added to the supernatant. Absorbance at 410 nm was read after incubation for 30 min at room temperature. Results were expressed as percentage of total cellular enzyme content, using the amount obtained in the same number of triton X-100-lysed cells.

Statistical Analysis.

Statistical significance of the differences between various treatment groups was assessed with one-way ANOVA. P values of <0.05 were taken as significant.

Neutrophil MPO Release

It was found that 100 nM PMA (as a stimulator of inflammatory mediator release) increased human neutrophil MPO release by approximately threefold versus control level at 30 min in the PMA control reference, the release of MPO increasing to approximately 5-6 fold after 3 hrs. At 30 minutes, relative to the control MPO activity as 100% absent PMA and absent PMA plus MANS or RNS, MPO activity of the PMA control reference was about 275%, PMA plus 50 µM MANS was about 275%, and 100 µM MANS was about 305%. Thus, the MANS peptide had no detected effect at 30 min. However, by 1 hr the higher concentration of MANS (100 µM) had a significant inhibitory effect (measured at about 260% of control) or about 25% reduction in MPO release versus the PMA control reference level (which was measured at about 340% of control). The 50 µM MANS sample measured about 290% of control or about 15% reduction relative to the PMA control reference. By 2 hrs and persisting at 3 hrs, the MANS peptide significantly attenuated MPO activity in a concentration-dependent manner. At 2 hours, the PMA control reference MPO activity was about 540% of control, the 50 µM MANS (measuring about 375% of control) caused an approximately 30% reduction of MPO release versus the PMA control reference; and 100 µM MANS (measuring about 295% of control) caused an approximately 45% reduction of MPO release versus the PMA control reference. At 3 hours, the PMA control reference MPO activity was about 560% of control, 50 µM MANS (measuring about 375% of control) caused an approximately 33% reduction of MPO release versus the PMA control reference; 100 µM MANS (measuring about 320% of control) caused an approximately 40% reduction of MPO release versus the PMA control reference. The RNS peptide did not affect PMA-induced MPO release at any of the time points or concentrations tested.

HL-60 EPO Release

EPO activity in the supernatant of HL-60 clone 15 cells was significantly enhanced at 1 and 2 hrs after PMA stimulation. At 1 hour, relative to EPO activity of the control as 100%, the PMA control reference measured at about 110%; the sample containing 10 µM MANS measured at about 95% to give about 15% reduction in EPO activity relative to the PMA control reference; the sample containing 50 µM MANS measured at about 78% to give about 30% reduction in EPO activity relative to the PMA control reference; and the sample containing 100 µM MANS measured at about 65% to give about 40% reduction in EPO activity relative to the PMA control reference. At 2 hour, relative to EPO activity of the control as 100%, the PMA control reference measured at about 145%; the sample containing 10 µM MANS measured at about 130% to give about 10% reduction in EPO activity relative to the PMA control reference; the sample containing 50 µM MANS measured at about 70% to give about 50% reduction in EPO activity relative to the PMA control reference; and the sample containing 100 µM MANS measured at about 72% to give about 50% reduction in EPO activity relative to the PMA control reference. Thus, at both 1 and 2 hrs, MANS at 50 or 100 µM significantly attenuated EPO release. The RNS peptide did not affect PMA-enhanced EPO release at any of the time points or concentrations tested.

U937 Lysozyme Release

Lysozyme secretion by U937 cells was increased by PMA stimulation by 1 hr after incubation, and increased even more at 2 hrs. At 1 hour, relative to lysozyme secretion by U937 cells of the control as 100%, the PMA control reference measured at about 210%; the sample containing 10 µM MANS measured at about 170% to give about 20% reduction in lysozyme secretion by U937 cells relative to the PMA control reference; the sample containing 50 µM MANS measured at about 170% to give about 20% reduction in lysozyme secretion by U937 cells relative to the PMA control reference; and the sample containing 100 µM MANS measured at about 115% to give about 45% reduction in lysozyme secretion by U937 cells relative to the PMA control reference. At 2 hour, relative to lysozyme secretion by U937 cells of the control as 100%, the PMA control reference measured at about 240%; the sample containing 10 µM MANS measured at about 195% to give about 20% reduction in lysozyme secretion by U937 cells relative to the PMA control reference; the sample containing 50 µM MANS measured at about 185% to give about 25% reduction in lysozyme secretion by U937 cells relative to the PMA control reference; and the sample containing 100 µM MANS measured at about 140% to give about 40% reduction in lysozyme secretion by U937 cells relative to the PMA control reference. Thus, lysozyme secretion was significantly attenuated at both 1 and 2 hours post-stimulation by 100 µM of MANS but not as much by 50 or 10 µM of MANS. The RNS peptide did not affect PMA-enhanced lysozyme secretion at any of the time points or concentrations tested.

NK Cell Granzyme Release

At 1 hour, relative to granzyme secretion by NK-92 cells of the control as 100%, the PMA control reference measured at about 125%; the sample containing 10 µM MANS measured at about 115% to give about 10% reduction in granzyme secretion by NK-92 cells relative to the PMA control reference; and the sample containing 100 µM MANS measured at about 85% relative to the PMA control reference to give about 30% reduction in granzyme secretion by NK-92 cells relative to the PMA control reference. At 2 hour, relative to granzyme secretion by NK-92 cells of the control as 100%, the PMA control reference measured at about 220%; the sample containing 10 µM MANS measured at about 200% to give about 10% reduction in granzyme secretion by NK-92 cells relative to the PMA control reference; and the sample containing 100 µM MANS measured at about 80% to give about 60% reduction granzyme secretion by NK-92 cells relative to the PMA control reference. Thus, granzyme secretion by NK-92 cells was not significantly increased by PMA at 1 hr, but increased over two-fold at 2 hours. 100 µM of MANS, but not 10 µM of MANS, attenuated granzyme secretion at 1 and 2 hrs after incubation. The RNS peptide did not affect PMA-enhanced granzyme secretion at any of the time points or concentrations tested.

Cytotoxicity

None of the treatments generated a toxic response in the cells, as assessed by LDH retention/release (data not shown) (see also Park J-A, He F, Martin L D, Li Y, Adler K B. Human neutrophil elastase induces hypersecretion of mucin from human bronchial epithelial cells in vitro via a PKCδ-mediated mechanism. Am J Pathol 2005; 167:651-661).

The foregoing examples are illustrative of the present invention and are not to be construed as limiting thereof. The invention is defined by the following claims, with equivalents of the claims to be included therein.

We claim:

1. A method of inhibiting release of an inflammatory mediator associated with a chronic inflammatory disease in a subject comprising contacting an inflammatory cell in the subject suffering from a chronic inflammatory disease, which cell comprises the inflammatory mediator contained within a granule inside the cell, with at least one active myristoylated N-terminal fragment of a MANS peptide (SEQ ID NO:1), wherein said fragment comprises at least six contiguous amino acids of said MANS peptide, in an effective amount to reduce the MARCKS-related release of the inflammatory mediator from the inflammatory cell.

2. The method of claim 1, wherein said inflammatory mediator is selected from the group consisting of myeloperoxidase (MPO), eosinophil peroxidase (EPO), major basic protein (MBP), lysozyme, granzyme, histamine, proteoglycan, protease, a chemotactic factor, cytokine, a metabolite of arachidonic acid, defensin, bactericidal permeability-increasing protein (BPI), elastase, cathepsin G, cathepsin B, cathepsin D, beta-D-glucuronidase, alpha-mannosidase, phospholipase $A_2$, chondroitin-4-sulphate, proteinase 3, lactoferrin, collagenase, complement activator, complement receptor, N-formylmethionyl-leucyl-phenylalanine (FMLP) receptor, laminin receptor, cytochrome $b_{558}$, monocyte-chemotactic factor, histaminase, vitamin B12 binding protein, gelatinase, plasminogen activator, and a combination thereof.

3. The method according to claim 1, wherein said active fragment can be selected from the group consisting of N-myristoyl-GAQFSKTAAKGEAAAERPGEAAV (SEQ ID NO: 20); N-myristoyl-GAQFSKTAAKGEAAAERPGEAA (SEQ ID NO: 3); N-myristoyl-GAQFSKTAAKGEAAAERPGEA (SEQ ID NO: 4); N-myristoyl-GAQFSKTAAKGEAAAERPGE (SEQ ID NO: 5); N-myristoyl-GAQFSKTAAKGEAAAERPG (SEQ ID NO: 6); N-myristoyl-GAQFSKTAAKGEAAAERP (SEQ ID NO: 7); N-myristoyl-GAQFSKTAAKGEAAAER (SEQ ID NO: 8); N-myristoyl-GAQFSKTAAKGEAAAE (SEQ ID NO: 9); N-myristoyl-GAQFSKTAAKGEAAA (SEQ ID NO: 10); N-myristoyl-GAQFSKTAAKGEAA (SEQ ID NO: 11); N-myristoyl-GAQFSKTAAKGEA (SEQ ID NO: 12); N-myristoyl-GAQFSKTAAKGE (SEQ ID NO: 13); N-myristoyl-GAQFSKTAAKG (SEQ ID NO: 14); N-myristoyl-GAQFSKTAAK (SEQ ID NO: 15); N-myristoyl-GAQFSKTAA (SEQ ID NO: 16); N-myristoyl-GAQFSKTA (SEQ ID NO: 17); N-myristoyl-GAQFSKT (SEQ ID NO: 18); and N-myristoyl-GAQFSK (SEQ ID NO: 19).

4. The method according to claim 1, wherein said inflammatory cell is a leukocyte.

5. The method according to claim 1, wherein said inflammatory cell is a granulocyte.

6. The method according to claim 1, wherein said inflammatory cell is selected from the group consisting of a neutrophil, a basophil, an eosinophil and a combination thereof.

7. The method according to claim 1, wherein said inflammatory cell is a monocyte or macrophage.

8. The method according to claim 1, wherein said inflammatory mediator is selected from the group consisting of myeloperoxidase (MPO), eosinophil peroxidase (EPO), lysozyme, granzyme and a combination thereof.

9. The method according to claim 1, wherein said effective amount comprises a degranulation-inhibiting amount of an active fragment of MANS peptide that reduces the amount of an inflammatory mediator released from said inflammatory cell from about 1% to about 99% as compared to the amount released from said inflammatory cell in the absence of said active fragment.

10. The method according to claim 1, wherein said effective amount comprises a degranulation-inhibiting amount of an active fragment of MANS peptide that reduces the amount of an inflammatory mediator released from said inflammatory cell from between about 5-50% to about 99% as compared to the amount released from said inflammatory cell in the absence of said active fragment.

11. The method of claim 1, wherein the chronic inflammatory disease is selected from the group consisting of insulin-dependent diabetes mellitus, multiple sclerosis, Gullian-Barre syndrome, graft versus host disease, and systemic lupus erythematosus.

12. A method of inhibiting release of an inflammatory mediator associated with a chronic inflammatory disease in a subject comprising:
administration to a tissue and/or fluid of said subject suffering from a chronic inflammatory disease, wherein said tissue and/or said fluid comprises at least one inflammatory cell comprising at least one inflammatory mediator contained within a granule inside the cell, a therapeutically effective amount of a pharmaceutical composition comprising at least one active myristoylated N-terminal fragment of a MANS peptide (SEQ ID NO:1), wherein said fragment comprises at least six contiguous amino acids of said MANS peptide, in a therapeutically effective amount to reduce the MARCKS-related release of said at least one inflammatory mediator from said inflammatory cell.

13. The method of claim 12, wherein said inflammatory mediator is selected from the group consisting of myeloperoxidase (MPO), eosinophil peroxidase (EPO), major basic protein (MBP), lysozyme, granzyme, histamine, proteoglycan, protease, a chemotactic factor, cytokine, a metabolite of arachidonic acid, defensin, bactericidal permeability-increasing protein (BPI), elastase, cathepsin G, cathepsin B, cathepsin D, beta-D-glucuronidase, alpha-mannosidase, phospholipase $A_2$, chondroitin-4-sulphate, proteinase 3, lactoferrin, collagenase, complement activator, complement receptor, N-formylmethionyl-leucyl-phenylalanine (FMLP) receptor, laminin receptor, cytochrome $b_{558}$, monocyte-chemotactic factor, histaminase, vitamin B12 binding protein, gelatinase, plasminogen activator, and a combination thereof.

14. The method according to claim 12, wherein said reducing the MARCKS-related release of said inflammatory mediator comprises blocking or inhibiting the mechanism that releases said inflammatory mediator from said inflammatory cell.

15. The method according to claim 12, wherein said active fragment can be selected from the group consisting of N-myristoyl-GAQFSKTAAKGEAAAERPGEAAV (SEQ ID NO: 20); N-myristoyl-GAQFSKTAAKGEAAAERPGEAA (SEQ ID NO: 3); N-myristoyl-GAQFSKTAAKGEAAAERPGEA (SEQ ID NO: 4); N-myristoyl-GAQFSKTAAKGEAAAERPGE (SEQ ID NO: 5); N-myristoyl-GAQFSKTAAKGEAAAERPG (SEQ ID NO: 6); N-myristoyl-GAQFSKTAAKGEAAAERP (SEQ ID NO: 7); N-myristoyl-GAQFSKTAAKGEAAAER (SEQ ID NO: 8); N-myristoyl-GAQFSKTAAKGEAAAE (SEQ ID NO: 9); N-myristoyl-GAQFSKTAAKGEAAA (SEQ ID NO: 10); N-myristoyl-GAQFSKTAAKGEAA (SEQ ID NO: 11); N-myristoyl-GAQFSKTAAKGEA (SEQ ID NO: 12); N-myristoyl-GAQFSKTAAKGE (SEQ ID NO: 13); N-myristoyl-GAQFSKTAAKG (SEQ ID NO: 14); N-myristoyl-GAQFSKTAAK (SEQ ID NO: 15); N-myristoyl-GAQFSKTAA (SEQ ID NO: 16); N-myristoyl-GAQFSKTA (SEQ ID NO: 17); N-myristoyl-GAQFSKT (SEQ ID NO: 18); and N-myristoyl-GAQFSK (SEQ ID NO: 19).

16. The method according to claim 12, wherein said inflammatory cell is a leukocyte.

17. The method according to claim 12, wherein said inflammatory cell is a granulocyte.

18. The method according to claim 12, wherein said inflammatory cell is selected from the group consisting of a neutrophil, a basophil, an eosinophil and a combination thereof.

19. The method according to claim 12, wherein said inflammatory cell is a monocyte or macrophage.

20. The method according to claim 12, wherein said inflammatory mediator is selected from the group consisting of myeloperoxidase (MPO), eosinophil peroxidase (EPO), lysozyme, granzyme and a combination thereof.

21. The method according to claim 12, wherein said effective amount comprises a degranulation-inhibiting amount of an active fragment of MANS peptide that reduces the amount of an inflammatory mediator released from said inflammatory cell from about 1% to about 99% as compared to the amount released from said inflammatory cell in the absence of said active fragment.

22. The method according to claim 12, wherein said effective amount comprises a degranulation-inhibiting amount of an active fragment of MANS peptide that reduces the amount of an inflammatory mediator released from said inflammatory cell from about 5 to 50% to about 99% as compared to the amount released from said inflammatory cell in the absence of said active fragment.

23. The method according to claim 12, wherein said chronic inflammatory disease is selected from the group consisting of insulin-dependent diabetes mellitus, multiple sclerosis, Gullian-Barre syndrome, graft versus host disease, and systemic lupus erythematosus.

24. The method according to claim 12, wherein said subject is a mammal.

25. The method according to claim 12, wherein said mammal is selected from the group consisting of a human, a canine, an equine and a feline.

26. The method according to claim 12, wherein said administration is selected from the group consisting of topical administration, parenteral administration, rectal administration, pulmonary administration, nasal administration, and oral administration.

27. The method according to claim 26, wherein said pulmonary administration is selected from the group of aerosol, dry powder inhaler, metered dose inhaler, and nebulizer.

28. The method according to claim 12, further comprising administration to said subject of a second molecule selected from the group consisting of an antibiotic, an antiviral compound, an antiparasitic compound, an anti-inflammatory compound, and an immunosuppressant.

* * * * *